(12) United States Patent
Wang et al.

(10) Patent No.: US 8,008,542 B2
(45) Date of Patent: Aug. 30, 2011

(54) COMPOSITIONS, CELLS, AND PLANTS THAT INCLUDE BKI1, A NEGATIVE REGULATOR OF BRI1-MEDIATED BR SIGNALING

(75) Inventors: Xuelu Wang, Shanghai (CN); Joanne Chory, Del Mar, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 524 days.

(21) Appl. No.: 12/008,398

(22) Filed: Jan. 9, 2008

(65) Prior Publication Data
US 2009/0013433 A1    Jan. 8, 2009

Related U.S. Application Data

(60) Provisional application No. 60/879,867, filed on Jan. 10, 2007.

(51) Int. Cl.
*A01H 1/00* (2006.01)
*A01H 5/00* (2006.01)

(52) U.S. Cl. ........ 800/278; 800/290; 800/295; 800/298; 435/410; 435/468; 536/23.6

(58) Field of Classification Search .................. None
See application file for complete search history.

(56) References Cited

U.S. PATENT DOCUMENTS
2008/0263727 A1 * 10/2008 DeRocher et al. ............ 800/287

FOREIGN PATENT DOCUMENTS
EP           1586645     * 10/2005

OTHER PUBLICATIONS

Belhkhadir and Chory (2006) "Brassinosteroid Signaling: A Paradigm for Steroid Hormone Signaling from the Cell Surface." *Science*, 314(5804): 1410-1411.
Wang and Chory (2006) Brassionsteroids Regulate Dissociation of BKI1, a Negative Regulator of BRI1 Signaling, from the Plasma Membrane. *Science express*, p. 1-6.
Friedrichsen et al. (2000) "Brassinosteroid-insensitive-1 is a ubiquitously expressed leucine-rich repeat receptor serine/theronine kinase." *Plant Physiology*, 123(4): 1247-1256.
Kinoshita et al. (2005) "Binding of brassinosteroids to the extracellular domain of plant receptor kinase BRI1." *Nature*, 433(7022): 167-171.
Li and Chory (1997) "A putative lucine-rich repeat receptor kinase involved in brassinosteroid signal transduction." *Cell*, 90(5): 929-238.
Li et al. (2002) "BAK1, an *Arabidopsis* LRR receptr-like protein kinase, interacts with BRI1 and modulates brassinosteroid signaling." *Cell*, 110(2): 213-222.
Nam and Li (2002) "BRI1/BAK1, a receptor kinase pair mediating brassinosteroid signaling." *Cell*, 110(2): 203-212.
Vert et al. (2005) "Molecular mechanisms of steroid hormone signaling in plants." *Annu Rev Cell Dev Biol*, 21: 177-201.
Wang and Chory (2006) "Brassinosteroids Regulate Dissociation of BKI1, a Negative Regulatory of BRI1 Signaling, from the Plasma Membrane." *Science*, 313(5790): 1118-1122.
Wang et al. (2001) "BRI1 is a Critical Component of a plasma-membrane receptor for plant steroids." *Nature*, 410(6826): 380-383.
Wang et al. (2005) "Autoregulation and Homodimerization Are Involved in the Activation of the Plant Steroid Receptor BRI1." *Cell*, 8: 855-865.
Wang et al. (2005) "Identification and Functional Analysis of in Vivo Phosphorylation Sites of the Arabidopsis Brassinosteroid-Insensitive1 Receptor Kinase." *The Plant Cell*, 17: 1685-1703.

* cited by examiner

*Primary Examiner* — Eileen B O Hara
(74) *Attorney, Agent, or Firm* — Kilpatrick Townsend & Stockton LLP

(57) ABSTRACT

This invention provides recombinant cells and transgenic plants that display selectively increased or decreased response to brassinosteroids, resulting in increased yield. Methods of modulating brassinosteroid responses, and of modulating plant phenotypes, are provided.

28 Claims, 16 Drawing Sheets

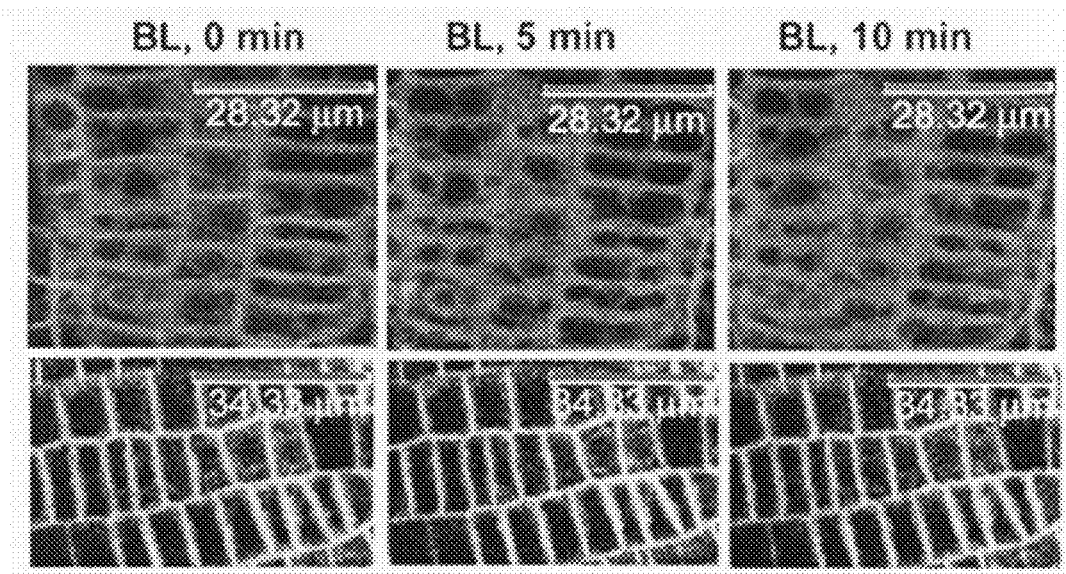
Fig. 4A
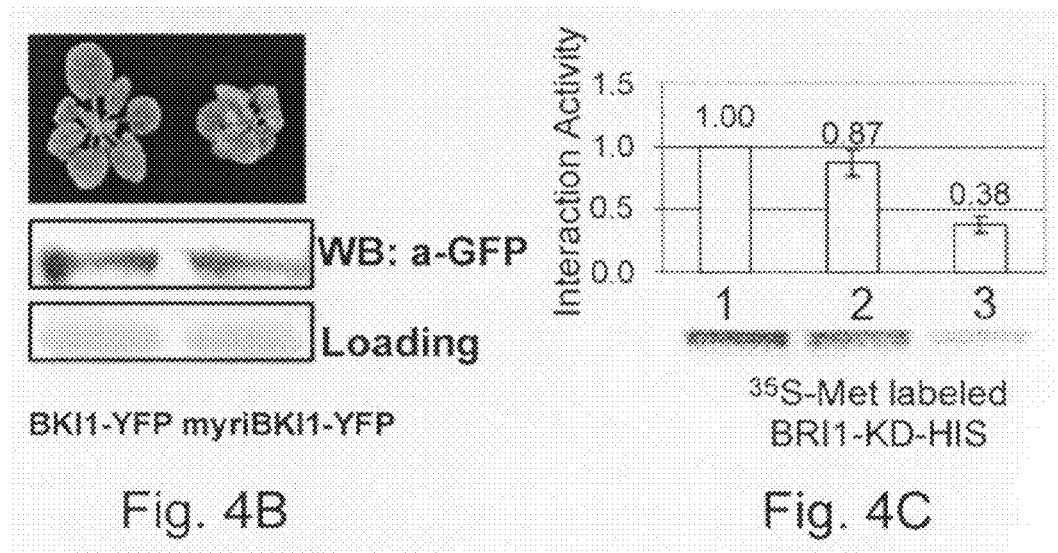
Fig. 4B
Fig. 4C

SEQUENCE LISTING

```
<160> NUMBER OF SEQ ID NOS: 45

<210> SEQ ID NO 1
<211> LENGTH: 337
<212> TYPE: PRT
<213> ORGANISM: Arabidopsis thaliana

<400> SEQUENCE: 1

Met Glu Thr Asn Leu Gln Gln Val Lys Asn Ser Ser Gln Thr Phe Ser
1               5                   10                  15

Glu Lys Gln Asn Pro Lys Gln Glu Ala Ser Pro Ser Pro Ile Ser Ser
            20                  25                  30

Thr Cys Ser Ser Pro Ser His Asp Phe Ser Phe Thr Ile Ser Leu Gln
        35                  40                  45

Pro Leu Ser Ser Ser Ser Lys His Ile Ser Pro Thr Leu Arg Ser Pro
    50                  55                  60

Ser Lys Thr Thr Ser Ser Tyr Gln Gln Thr Asp Pro Phe Ala Val Asp
65                  70                  75                  80

Leu Ser Pro Ala Asp Glu Ile Phe Phe His Gly His Leu Leu Pro Leu
                85                  90                  95

His Leu Leu Ser His Leu Pro Val Ser Pro Arg Thr Ser Thr Gly Ser
            100                 105                 110

Tyr Asn Asp Gly Phe Thr Leu Pro Val Lys Asp Ile Leu Pro Asp Gln
        115                 120                 125

Pro Thr Asn Asn Asn Asn Asn Thr Glu Asn Ala Ile Thr Asn Ile Ser
    130                 135                 140

Thr Glu Ala Lys Asp Asp Asn Thr Glu Asp Lys Ala Glu Gly Glu Ile
145                 150                 155                 160

Arg Val Lys Thr Lys Pro Ile Lys Ser Phe Ser Leu Phe Gly Leu Ser
                165                 170                 175

Lys Trp Arg Lys Gly Phe Glu Ser Asn Glu Arg Glu Gln Glu Gln Gln
            180                 185                 190

Gln Gln Lys Ile Lys Lys Pro Met Ser Leu Asp Leu Ser His Ala Val
        195                 200                 205

Lys Lys Tyr Ile Arg Met Leu Phe Gln Lys Arg Gly Asn Gly Thr Gln
    210                 215                 220

Phe Trp Asn Arg Arg Gln Thr Ser Ser Tyr Ser Phe Ser Ser Ser Leu
225                 230                 235                 240

Met Gly Pro Asn Gly Asn Ser Lys Thr Met Ile Asn Gly Ser Tyr Asn
                245                 250                 255

Lys Arg Asp Leu Ile Arg Gly Arg Gly Glu Leu Phe Ser Ala Pro
            260                 265                 270

Ala Ser Met Arg Thr Ser Pro Thr Asn Ser Gly His Leu Arg Val Ser
        275                 280                 285

Thr Ala Gly Leu Ser Ser Ser Gly Ser Thr Ser Ser Ser Ser
    290                 295                 300
```

Asp Ser Thr Met Glu Glu Leu Gln Ala Ala Ile Gln Ala Ala Ile Ala
305                 310                 315                 320

His Cys Lys Asn Ser Ser Ala Val Asp Arg Asp Asp Lys Val Lys Asp
            325                 330                 335

Ser

<210> SEQ ID NO 2
<211> LENGTH: 262
<212> TYPE: PRT
<213> ORGANISM: Oryza sativa

<400> SEQUENCE: 2

Met Asn Thr Pro Arg Pro Arg Ser Gln Pro Pro Pro His Pro Pro
1               5                   10                  15

Leu Phe Lys Pro Thr Thr Pro Pro Pro Leu Leu Ser Thr Ser
                20                  25                  30

Thr Ser Thr Ser Pro Pro His Asp Phe Ser Phe Ala His Tyr Leu Ser
            35                  40                  45

Ser Pro Pro Pro Ser Val Gln Arg Arg Gly Arg Ala Asp Met Ser Arg
50                  55                  60

Thr Pro Pro Leu Gly Arg Val Gly Ser Asp Leu Ser His Asn Asn Tyr
65              70                  75                  80

Ser Ser Lys Ala Asn Gln His Arg Gln Thr Gly Ser Ser Ser Ser
                85                  90                  95

Lys Glu Lys Asp Arg Glu Tyr Lys Ala Lys Ser Lys Ala Ser Ser Pro
                100                 105                 110

Phe Phe Ser Gly Leu Gly Gly Ser Trp Arg Ser Gly Leu Ser Arg Asp
            115                 120                 125

Glu Glu Val Lys Arg Lys Ala Lys Ala Lys Thr Arg Gly Leu Asp Val
            130                 135                 140

Gly Gln Trp Val Lys Lys Tyr Met Ala Ser Met Val Glu His Leu Leu
145                 150                 155                 160

Ala Ser Phe Ser Arg His Gly Gly Gly Glu Arg Glu Lys Arg Glu Gln
                165                 170                 175

Gln Arg Arg Arg Pro His Ser Phe Ser Ala His Gly Pro Ser Ala Leu
            180                 185                 190

Arg Glu Gln Arg Glu Arg Trp Arg Arg Arg Gly Gln Leu Ser Ser
            195                 200                 205

Ala Pro Ala Ser Leu Arg Ala Ser Pro Val Asn Ser Gly His Leu Ser
210                 215                 220

Val Gly Gly Ser Val Lys Val Ser Thr Ser Ser Glu Glu Ser Thr Met
225                 230                 235                 240

Glu Glu Leu Gln Ser Ala Ile Glu Ala Ala Ile Ala His Cys Lys Asn
                245                 250                 255

Ser Ile Thr Val Ala Lys
            260

<210> SEQ ID NO 3
<211> LENGTH: 297
<212> TYPE: PRT
<213> ORGANISM: Medicago truncatula

<400> SEQUENCE: 3

Met Glu Lys Gln Ile Glu Val Glu Asn Gln Gln Gln Lys Pro Ser Gln
1               5                   10                  15

Pro Cys Ser His Gln Asn Ser Gln Ser Ser Ser Pro Thr His Asp Phe

```
                    20                  25                  30
Ser Phe Thr Ile Ser His Asn Ser Phe Asn Thr Thr Phe Pro Asn Asn
                35                  40                  45

His Asn Lys Ser Lys Leu Ser Ser His Asn Ser Phe Thr Ala Leu Asp
    50                  55                  60

Leu Ser Pro Ala Asp Asp Ile Phe Phe His Gly His Leu Leu Pro Leu
65                  70                  75                  80

Gln Ile Leu Ser His Phe Pro Ser Ser Ile Ser Pro Arg Ser Ser Thr
                85                  90                  95

Asn Ser Met Asp Ser Phe Thr Leu Pro Ile Arg Glu Leu Phe Ser Glu
            100                 105                 110

Asp Asp Asp Glu Asn Leu Pro Thr Lys Asp Ile Ser Ser Asn Asn
            115                 120                 125

Ser Ser Lys Ser Glu Asn Ser Ser Lys Asn Ile Glu Ser Ser Lys Lys
        130                 135                 140

Val Glu Gly Lys Ser Lys Phe Ser Phe Leu Ser Phe Ser Ser Asn Lys
145                 150                 155                 160

Ala Pro Lys Gly Cys Leu Lys Glu Lys Glu Asp Lys Val Lys Asn Lys
                165                 170                 175

Lys Lys Leu Arg Phe Asp Phe Asp Val Leu His Ala Val Lys Lys Tyr
            180                 185                 190

Leu Arg Lys Val Lys Pro Leu Phe Lys Arg Glu Lys Ile Arg Glu Gln
        195                 200                 205

Lys Lys Ser Tyr Ser Tyr Ser Gly Lys Asn Val Thr Pro Arg Thr Arg
    210                 215                 220

Asn Lys Gln Glu Leu Met Lys Gly Trp Ser Met Lys Leu Gly Gln Tyr
225                 230                 235                 240

Tyr Ser Ala Pro Ala Ser Met Arg Thr Ser Pro Thr Asn Ser Gly Val
                245                 250                 255

Leu Phe Ala Thr Thr Pro Leu Pro Pro Ser Asp Ser Ser Met Glu
            260                 265                 270

Glu Leu Gln Ala Ala Ile Gln Ser Ala Ile Ala His Cys Lys Asn Ser
        275                 280                 285

Tyr Ser Lys Glu Glu Lys Leu Asn Cys
    290                 295

<210> SEQ ID NO 4
<211> LENGTH: 315
<212> TYPE: PRT
<213> ORGANISM: Gossypium raimondii

<400> SEQUENCE: 4

Met Asn Gly Tyr Gln Gln Gln Lys Thr Thr Glu Gln Val Val Asp Arg
1               5                   10                  15

Lys His Gly Glu Gly Lys Leu Lys Gln Glu Pro Lys Glu Gly Ser Ala
            20                  25                  30

Asp Lys Gln Ser Pro Pro Ala Ser Pro Ser Ala Ala Ser Ser Pro
        35                  40                  45

Ser His Glu Phe Ser Phe Thr Val Val Ser Leu His Ser Ser Asn
    50                  55                  60

Ser Val Pro Gly Lys Thr Lys Thr Pro Ser Met Ala Ile Asp Leu
65                  70                  75                  80

Ser Pro Ala Asp Asp Ile Phe Phe His Gly His Leu Leu Pro Leu His
                85                  90                  95

Leu Leu Ser His Leu Pro Val Ser Pro Arg Cys Ser Thr Asn Ser Leu
```

-continued

```
                100                 105                 110
Asp Gly Phe Asn Gly Pro Ile Thr Asp Glu Pro Lys Pro Asp Lys Pro
            115                 120                 125
Asn Thr Gly Cys Lys Ser Lys Ser Asp Ser Asn Ile Lys Ser Ser Asn
        130                 135                 140
Lys Asn His Gly Lys Val Gly Asn Arg Pro Gln Ser Tyr Asn Ile Glu
145                 150                 155                 160
Ala Asn Gly Arg Pro Lys Ser Lys Phe Phe Thr Leu Phe Arg Leu Thr
                165                 170                 175
Arg Trp His His Lys Gly Arg Gly Val Trp Glu Thr Glu Lys Glu
            180                 185                 190
Lys Pro Lys Thr Lys Met Arg Phe Asp Leu Arg His Val Leu Lys Arg
        195                 200                 205
Tyr Val Arg Met Val Arg Pro Leu Leu Phe Phe Arg Gly Arg Arg Asp
210                 215                 220
Asn Trp His Leu Gln Arg Gln Phe His Ser Phe Ser Gly Asn Leu Ser
225                 230                 235                 240
Trp Lys Asn Lys Glu Lys Glu Leu Arg Ala Arg Lys Gly Arg Gly Glu
                245                 250                 255
Tyr Tyr Ser Ala Pro Ala Ser Met Arg Thr Ser Pro Thr Asn Ser Gly
            260                 265                 270
Phe Phe Val Ala Thr Pro Gly Phe Pro Phe Ser Thr Ser Asp Ser Pro
        275                 280                 285
Met Glu Glu Leu Gln Ala Ala Ile Gln Ala Ala Ile Ala His Cys Lys
    290                 295                 300
Asn Ser Leu Gln Gly Glu Asp Lys Phe Lys Cys
305                 310                 315

<210> SEQ ID NO 5
<211> LENGTH: 271
<212> TYPE: PRT
<213> ORGANISM: Euphorbia esula

<400> SEQUENCE: 5

Met Asp Thr Lys Gln His Ile Asn Ile Glu Gly Ala Glu Ala Lys Val
1               5                   10                  15
Pro Ser Ser Ser Ser Pro Ser His Glu Phe Ser Phe Thr Ile Ser
            20                  25                  30
Leu His Ser Ser Thr Pro Glu Thr Asn Asn Lys Ser Pro Lys
        35                  40                  45
Ser Leu Arg Leu Pro Pro Pro Pro Phe Ala Ile Asp Leu Thr Pro
50                  55                  60
Ala Asp Asp Ile Phe Phe His Gly His Leu Leu Pro Leu His Leu Leu
65                  70                  75                  80
Ser His Leu Pro Val Ser Pro Arg Ser Ser Thr Asn Ser Ile Asp Ser
                85                  90                  95
Phe Thr Leu Pro Ile Arg Asp Phe Leu Asp His Gln Ile Pro Asn
            100                 105                 110
Pro Ile Thr Thr Ser Glu Asn Ser Ile Asn Gly Glu Asn His Thr Thr
        115                 120                 125
Arg Ser Lys Pro Lys Ser Phe Ser Phe Arg Trp Arg Asn Arg Asp
    130                 135                 140
Arg Glu Asp Lys Asp Lys Gln Lys Lys Leu Arg Phe Glu Val Ser
145                 150                 155                 160
Arg Val Leu Lys Arg Tyr Leu Arg Met Val Arg Pro Leu Leu Phe Phe
```

```
                    165                 170                 175
Lys Gly Arg Arg Ser Glu Asn Val Gln Phe His Arg Gly Gln Pro Phe
            180                 185                 190

Asn Ser Phe Ser Gly Asn Leu Ser Trp Arg Asn Lys Gln Asp Leu Arg
        195                 200                 205

Gly Arg Arg Gly Glu Phe Ser Ala Pro Ala Ser Met Arg Thr Ser Pro
    210                 215                 220

Thr Asn Ser Gly Leu Leu Val Ala Lys Ala Thr Met Gly Cys Ser Gly
225                 230                 235                 240

Ser Asp Ser Thr Met Glu Glu Leu Gln Ala Ala Ile Gln Ala Ile
                245                 250                 255

Ala His Cys Lys Asn Ser Ile Ala Ala Glu Asp Lys Ile Thr Cys
            260                 265                 270

<210> SEQ ID NO 6
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 6
caccgacatc gtcttatcaa caaaccgat                                   29

<210> SEQ ID NO 7
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 7
acacacgaag atggccacta tt                                          22

<210> SEQ ID NO 8
<211> LENGTH: 11
<212> TYPE: PRT
<213> ORGANISM: Artificial
<220> FEATURE:
<223> OTHER INFORMATION: FLAG epitope tag

<400> SEQUENCE: 8

Asp Tyr Lys Asp Asp Asp Asp Lys Val Lys Leu
1               5                   10

<210> SEQ ID NO 9
<211> LENGTH: 7
<212> TYPE: PRT
<213> ORGANISM: Artificial
<220> FEATURE:
<223> OTHER INFORMATION: myristoylation site

<400> SEQUENCE: 9

Met Gly Ile Cys Met Ser Arg
1               5

<210> SEQ ID NO 10
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 10
```
ttaccgcaaa gccatccaa                                                      19

<210> SEQ ID NO 11
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 11
tcatcaccac caccgtcaac                                                     20

<210> SEQ ID NO 12
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 12
gttggccatt tcttggtgaa a                                                   21

<210> SEQ ID NO 13
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 13
tggcggtgta cggtttaaga t                                                   21

<210> SEQ ID NO 14
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 14
ttgggtgcta agcaaattat tcg                                                 23

<210> SEQ ID NO 15
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 15
tctcctacat agaccgccat ga                                                  22

<210> SEQ ID NO 16
<211> LENGTH: 16
<212> TYPE: DNA
<213> ORGANISM: Artificial
<220> FEATURE:
<223> OTHER INFORMATION: synthetic oligonucleotide primer

<400> SEQUENCE: 16
gctccggcgt cgatga                                                         16

<210> SEQ ID NO 17
<211> LENGTH: 20
<212> TYPE: DNA
<213> ORGANISM: Artificial
<220> FEATURE:

<223> OTHER INFORMATION: synthetic oligonucleotide primer

<400> SEQUENCE: 17
gacgatagtc cggccgtaga                                               20

<210> SEQ ID NO 18
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 18
tgcgctgcca gataatacac tatt                                          24

<210> SEQ ID NO 19
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 19
tgctgcccaa catcaggtt                                                19

<210> SEQ ID NO 20
<211> LENGTH: 740
<212> TYPE: DNA
<213> ORGANISM: Antirrhinum majus

<400> SEQUENCE: 20
gtgtaaaggg caaagaaaca cttataacag accaattttt ggccttccaa tcatcagagc    60
taatcatgga gacaaagcaa caaatggtaa gagaaaataa agaagagaag ctgaagaatg   120
aaggcaagag agatggacca caatcctcac caccttcatc ttcatcctct ccttctcatg   180
aattctcctt caccatatct ctccaccccct cgaaaattcc ggagaaaaac gctaagtcca   240
ctccttcgtt tgctatcgac cttacaccgg ccgacgagat tttcttccat ggacacttgc   300
tgccactcca cctcctctcc cacctccccg tctccccgcg cactaccact aattcattgg   360
atggtttcac tcttccgata aaagaattat tacacgacga caacaacgac aacaacaaca   420
acacagatga atgcaaaaac acaaacgaac acgataacat tcaagaaagc aatgttttgc   480
aaggtaaagg gagaggaaag tcgaaatctt tctcactttt cgggatgcaa aaacggagaa   540
aagatcatca agaaaagaa cataagcaaa gaaagaactt tggtgatttt gttagaaggt   600
acatgaagct ggtgaagcca tttctttctt tcaagagtaa caacagagga aactatcacg   660
atcatcgtcg tgttgacttc gaacgacagc cttattcgtt ttcgggcaat ttacttgtga   720
aaggcaagag agcattgaga                                              740

<210> SEQ ID NO 21
<211> LENGTH: 732
<212> TYPE: DNA
<213> ORGANISM: Antirrhinum majus

<400> SEQUENCE: 21
cattagcaac caaagaaaaa cagcacaaag acaagtgtaa agggcaaaga aacacttata    60
acagaccaat ttttggcctt ccaatcatca gagctaatca tggagacaaa gcaacaaatg   120
gtaagagaaa ataagaaga gaagctgaag aatgaaggca agagagatgg accacaatcc   180
tcaccacctt catcttcatc ctctccttct catgaattct ccttcaccat atctctccac   240

```
ccctcgaaaa ttccggagaa aaacgctaag tccactcctt cgtttgctat cgaccttaca    300
ccggccgacg agattttctt ccatggacac ttgccgacac tccacctcct ctcccacctc    360
cccgtctccc cgcgcacttc cactaattca ttggatagtt tcactcttcc gataaagaa     420 ttattcacg acgacaacaa cgacaacaac aacaacacag atgaatgcaa aaacacaaac     480
gaacacgata acattcaaga aagcaatgtt ttgcaaggta agggagagg aaagtcgaaa     540 tcttctcac ttttcgggat gcaaaaacgg agaaagatc atcaagagaa agaacataag      600
caaagaaaga actttggtga ttttgttaga aggtacatga agttggtgaa gccatttctt    660
tctttcaaga gtaacaacag aggaaactat cacgatcatc gtcgtggtga cttcgaacga    720
cagccttatt cg                                                        732

<210> SEQ ID NO 22
<211> LENGTH: 784
<212> TYPE: DNA
<213> ORGANISM: Citrus sinensis

<400> SEQUENCE: 22 tttttcgta atattgtctt tttcatatat atgtatatac catatgttgt aaacaagaaa      60
ataaatatgc aaatggtaat aacaaaaaga ataatactaa aagctgaaat agaataagtc    120
ttagcatttg atcttctctt caacagcaat ggaattcttg caatgagcga tagcagcttg    180
aattgcagct tgcaactctt ccatggtact atcacttgtc gatgaagaaa tatttgttgt    240
tgctacaagc aacccgctgt tgtgggaga cgttctgatt gatgcagggg ctgaaaattc     300
acctcttctt cctctaataa actgatcttg cttgctccta aagcttaaat tacctgaaaa    360
cgaatacgct tgccgttgga aatgatggcc attttctctc cttcctctga aaagcagcaa    420
tggcctaatc attctcacat accgtctaat tacatgactt acgtcgaacc tcagcttcct    480
cttttgctta ttctgatctt tgttgctatt gtcttcacat tctctaactt cataacccct    540
ccgccatctt gtgaacccga ataatgagaa tgacttggac ttgggtcttc tctttgattg    600
atcaagatga agatcattgc ttcgcagatg atggttgcag gatttgatgc tgctgctgct    660
gttattgcta ttaatgttgc tagtgctgca gttgctaaat ttcttttcag gaatctgatt    720
gtctcttaag tcattgatgg ggaggggtga agctgtccaa tgagttggtg gaggagcgag    780
ggga                                                                 784

<210> SEQ ID NO 23
<211> LENGTH: 685
<212> TYPE: DNA
<213> ORGANISM: Curcuma longa

<400> SEQUENCE: 23
gcaccggcgc cgccatcttc ggccaccgcc tcccctctc acgacttctc cttcaccatc      60
tccttccaaa ctctcagctc gccggccacc ctcaagggca ctgccaccaa gccgccctct    120
gcctcctctg ccgctttcga cttggccccc gccgatgata tcttcctcca tggccacctc    180
ctgcctctcc acctcctctc ccagcccggc agccccccgc gcgcctccga catctcgttg    240
gacaacttca cctatcccct cggccacacc gacagcgacc gccacgtcga ctacttcaac    300
ccgagcaagc ccgccaagga ggagagtaga gccgcgaagc cgacgtcggc gttcgcgtcc    360
ttcttcggcc tcgcgaggct gaggaagcgg aacgaaaaag aggcggcgga ggaggtgccg    420
acggcgacga cgaagaggaa aaggaagggg ctcgacgtga gcaggctgct gcggaagtac    480
gcgagcctga tggagctcct gttcttcttc aggacagggg agagggagcg ccgccgccgc    540
```

```
gacgatgacc tgcgacggcg accgtgctcc ttctcggggc actcgaatcg gaacaataag    600
gcggcggcgg cggcggcagc gactcatgga gagtggtggc ggcggaggaa ggggcagatg    660
tcggcgccgg cgtcgatgag gacgt                                          685
```

<210> SEQ ID NO 24
<211> LENGTH: 538
<212> TYPE: DNA
<213> ORGANISM: Glycine max

<400> SEQUENCE: 24

```
aaagaaaacg atgtgcaaaa gaaaactgaa gaaggagtag tagcaaagcc accttcacca     60
tcctcttccc cttctcacga attctccttc acaatctctc tccactctac ttctaacacc    120
acaatccaag acaaatccaa accccacct tctcttgcag ttgatctatc tccagcagat    180
gacattttct tccatggtca cttgcttcct ctacacctct tatctcactt ctcttcttca    240
cctcgctttt ccaccaactc cgtggacagt ttcacactcc ccatcagaga gttcttagaa    300
gatgaaaaac gcaacagcag caacaggagc aacatcacca tagatagcat taccagctgc    360
aacaacaaag atgactacta caacaataga gtcacaaagg aagaaagtaa gtccaagcct    420
agtttctcat tgtttggttt atcaaagggg cgtaaagggt gtcaagttag agataacaaa    480
gaagataaag aggataacat taagcacaag aagaaactag ggtatgatgt gatgcatg     538
```

<210> SEQ ID NO 25
<211> LENGTH: 495
<212> TYPE: DNA
<213> ORGANISM: Glycine max

<400> SEQUENCE: 25

```
acaacctcaa ctgtaataat ggaaacacat catcaacccc aaaagaacaa agaaaacgat     60
gtgcaaaaga aaactgaaga aggagtagta gcaaagccac cttccatcc ctcttcccct    120 tctcacgaat tctccttcac aatctctctc cactctactt ctaacaccac aatccaagac    180
aaatccaaaa ccccaccttc tcttgcagtt gatctatctc cagcagatga cattttcttc    240
catggtcact tgcttcctct acacctctta tctcacttct cttcttcacc tcgcttttcc    300
accaactccg tggacagttt cacactcccc atcagagagt tcttagaaga tgaaaaacgc    360
aacagcagca acaggagcaa catcaccata gatagcatta ccagctgcaa caacaaagat    420
gactactaca acaatagagt cacaaaggaa gaaagtaagt ccaagcctag tttctcattg    480
tttggtttat caaag                                                    495
```

<210> SEQ ID NO 26
<211> LENGTH: 495
<212> TYPE: DNA
<213> ORGANISM: Glycine max

<400> SEQUENCE: 26

```
acaaactaaa ctgtaataat ggaaacacat catcaacccc aaaagaacaa agaaaacgat     60
gtgcaaaaga aaactgaaga aggagtagta gcaaagccac cttccatcc ctcttcccct    120 tctcacgaat tctccttcac aatctctctc cactctactt ctaacaccac aatccaagac    180
aaatccaaaa ccccaccttc tcttgcaggt gatctatctc cagcagatga cattttcttc    240
catggtcact tgcttcctct acacctctta tctcacttct cttcttcacc tcgcttttcc    300
accaactccg tggacagttt cacactcccc atcagagagt tcttagaaga tgaaaaacgc    360
aacagcagca acaggagcaa catcaccata gatagcatta ccagctgcaa caacaaagat    420
```

```
gactactaca acaatagagt cacaaaggaa gaaagtaagt ccaagcctag tttctcattg    480
tttggtttat caaag                                                    495

<210> SEQ ID NO 27
<211> LENGTH: 469
<212> TYPE: DNA
<213> ORGANISM: Glycine max

<400> SEQUENCE: 27
aacacaacac ctcttatctc acttctcttc atcacctcgc ttttccacca actccgtgga    60
cagcttcaca ctccccatca gagagttctt agaagacgaa aaacgcaaca gctgcaatag   120
ctgcaacagc agcaacatca ccatagatag cattaccaac agcaacaaca tagaagacca   180
caacaataga gtcacaaagg aaggaagtaa gtccaagcct agtttctcat tgtttggttt   240
atcaaagggg cgtaaagggt gtcaagttag agacaaagaa gataaagagg ataacatcaa   300
gcacaagaag aaactcgggt atgatgtgat gcatgcactt aagaagtact tgagaatggt   360
gcagccacta gtgcttttcg gagggagaag agaaaaaggt cggttccatg acaagctta    420 ttctcattcg gggaatttga tccggaaaaa caagcctgaa ttgagagga               469

<210> SEQ ID NO 28
<211> LENGTH: 845
<212> TYPE: DNA
<213> ORGANISM: Helianthus petiolaris
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (190)..(191)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t

<400> SEQUENCE: 28
tcatctctct ctcttgtcta catagtgcat gcgatcatct ctcgtgacga gaggtgtacg    60
cttgcacgtt gtagacatga gagatcgtaa actacagaat gagcctgaac ttacgtgaag   120
aagctagaag ctacgaccct ccgcgaaact gtccgaaatc catctcccac acaaagcggc   180
gcttatangn naccatcggc atcgcaatct cctacccatg agttctcttt caccatttct   240
ctcaacccta atccaccaca aaaatctaca caagatggtc acaagtacaa cacttatatt   300
gataatgaca aggacaacca caaccacaac caccaccacc gtagcttcac accaccaccc   360
gaaccattga ccgccattga cttatctccg gctgatgaca tcttcttcca tggtcacctc   420
ctccctctcc accttctctc tcatctcccc atatcccctc gctcttcaac aaactcaatg   480
gacagtttta ccctccccat gaaagatatt ttaaaagatc aaaacaaccc tattggaaac   540
actagttttc attaccacca ccggaacacc ttctctgaat tcaatctacc caacaacaat   600
gtcactcaaa caagaccaaa gtcgaaatct ttctcaatct ttagccgacc caagtggaaa   660
aaaggatcac ttgatgaaag agaagtagac cttgaaaacc aagatcaaga aagacacaac   720
aactccnaga aaaagctcaa actagaagtg gctcaactca tcaaaaggta catgaaaatg   780
gtgagacctt ttatgtcatt tacaaaggcg aagaggccga ataccgagtt tacccggcag   840
ccgca                                                                845

<210> SEQ ID NO 29
```

<211> LENGTH: 531
<212> TYPE: DNA
<213> ORGANISM: Ipomoea nil

<400> SEQUENCE: 29

| | | | | | |
|---|---|---|---|---|---|
| aggagatcag | agacgacaaa | gatgaagaga | agcaagggcg | caacagagta | aaggaggaag | 60 |
| aggcggcgga | agagcaaaca | tcgagtagtg | gcaatgccgc | cgccgcgtca | ccgccgtcag | 120 |
| cgtcgtcatc | tccgtcgcat | gaattttcct | tcaccatttc | gctccatcaa | ccgtctgcaa | 180 |
| aagccccaga | cagaacgaaa | tctccgccgc | agccgtcgtc | gttcgccgtc | gacttaactc | 240 |
| cggccgatga | aatattcttc | cacggccact | tgctcccccct | ccacctcctc | tcccacctcc | 300 |
| ccgtctcccc | tcgctcctcc | accaactcgc | tggaaagttt | cacccttccc | ataaaagaat | 360 |
| tgctggaaaa | ccaaagctca | tcacaacaaa | accccggcag | ccaaccagac | aaccatgatc | 420 |
| atcagaaaaa | cattaataac | gatcaaagaa | ccgaggggaa | accgaaatcc | agcaggtcgt | 480 |
| tctccttgtt | ctggctaccg | aaatggagaa | aagggtacga | ggtaagagac | a | 531 |

<210> SEQ ID NO 30
<211> LENGTH: 713
<212> TYPE: DNA
<213> ORGANISM: Ipomoea nil
<220> FEATURE:
<221> NAME/KEY: misc_feature
<222> LOCATION: (701)..(701)
<223> OTHER INFORMATION: n is a, c, g, or t

<400> SEQUENCE: 30

| | | | | | |
|---|---|---|---|---|---|
| tatggtctga | tttacttgac | taatggctgc | ggatttcccc | ggcaccaaaa | aaatagtaat | 60 |
| atggtaattt | aaaaaaaaag | ggagaaaatt | aaattaaaaa | gaagtttggg | atatgctcat | 120 |
| gtgcaggcct | aatcttgaca | tttgagttta | tcttccactt | gaatggattt | cttgcagtga | 180 |
| gcaatggcag | cttgaatggc | ggcctgtaac | tcttccatgg | tgctgtcgct | tgaagaagta | 240 |
| ggggaagttg | ccggtggtac | gaggatgcca | ctgtttgtcg | gagatgttct | catcgatgcc | 300 |
| ggcgcggaat | actcccctct | tttgcctcta | atatctttct | tgcgccgcag | gtttaagtgg | 360 |
| ccggaatatg | aataagcttg | ccggtcgaac | tgcagattcc | ctgatcttct | gctgggccgg | 420 |
| aaggataaga | gtggtctcac | cattctcatg | tacctcttca | caacctgagt | tatgtcaaat | 480 |
| tttagcttcc | tccaatgttt | ttccttctct | tccttgtctc | ttacctcgta | ccctttctc | 540 |
| catttcggta | gccagaacaa | ggagaacgac | ctgctggatt | tcggtttccc | ctcggttctt | 600 |
| tgatcgttat | taatgttttt | ctgatgatca | tggttgtctg | gttggctgcc | ggggttttgt | 660 |
| tgtgatgagc | tttggttttc | cagcaattct | tttatgggaa | nggtgaaact | ttc | 713 |

<210> SEQ ID NO 31
<211> LENGTH: 890
<212> TYPE: DNA
<213> ORGANISM: Lettuce sativa

<400> SEQUENCE: 31

| | | | | | |
|---|---|---|---|---|---|
| gtagcctgcc | cctaactcta | gttgttctca | ttctctatct | ctctcttctt | ctgagctcca | 60 |
| taacttttttg | ttatccaatt | ttctgttact | ggttgtcagg | aattgggtaa | gaatagaagt | 120 |
| cgtctgtatg | atggataacg | ccgatgatga | gcaaacttac | tttaataaac | aagaatcaat | 180 |
| gctactacac | caaactagcc | aaaatccatg | ttcaccaccg | tcttcaccac | caccagccac | 240 |
| cgcatcacct | tcctcagtct | cttcatctcc | tactcatgaa | ttctccttta | ccgtttctct | 300 |
| ccacccaaac | ccaccaccaa | tattcactca | acgtcataat | tctgatactt | atgatagcga | 360 |

```
taacaaccat aaaaccgaca ctactagttc tcttctacca tatccaccat tgacagctat    420
tgacttatct ccagcggatg gtatcttctt ccacggccat ctccttcctc ttcacctcct    480
atctcctctc cctgtctccc ctcgctcctc cacaaactca atggacagtt ataccctccc    540
cagcagcctc ttatatgacc aaaccaaccc tatcggaaac accagcttcc actgccacca    600
ccaaaccgcc ttctccgatt tcgaagagcc tgaggtcgcc attagcaatc aaaaccgacc    660
aaagtccaaa tcttttttcac tctttagcat acccaaatgg aaaaaaagga gtgatgatga    720
gagagaaaga ggtgaagatc aaaataccaa gaagctgaag ttagatttag gtcagctcat    780
caagaggtac atgaaaatgg taaggccttt gttgtcattt ccaaagtcga ggaggtcaaa    840
tacgactttt aaccatcagt catattcatt ttctggaaac tcactgagtt               890

<210> SEQ ID NO 32
<211> LENGTH: 690
<212> TYPE: DNA
<213> ORGANISM: Lettuce sativa

<400> SEQUENCE: 32
ggggttcggc cattatggcc gctcccgggg gatgagagat aaagtataaa atgaacaaag     60
ttacatgaag aagcaagaag caatactaca agaaagcatc cagacttcat ctccaccacc    120
aacggccacc tcatctccac catcagcatc ggcatctcca acccatgaat tctccttcac    180
catctccctc catccgcatc aacacaaaa atcgcaacaa gatggttata actccggcaa     240
ctatgatgat aataaccacc gtaaacatgg taacaccaca acaccaccat cggaaccatt    300
gactgctatt gacctttctc cggcggatga tatcttcttc catggccacc tccttcctct    360
ccatctcctg tctcatcttc ccatatcccc tcgtacatcg acaacttcaa tggatagttt    420
taccctccca acgaaggaca tcctaaagga ccaacataac cccattggaa acactagttt    480
ccattatcac caccggaaca ccttctcaga gttcaacttg accagcaaca atgtcaatca    540
aatcagacca aagtccaaat cttttctcgtt gtttggccgt aacaaaggaa aaaaaggatg    600
cgctgatgaa agagaaagag atcacgaaga tcaagataaa gaaagaaaca acagtaattc    660
ccaggaagaa gctgaaatta gaggtggctc                                     690

<210> SEQ ID NO 33
<211> LENGTH: 769
<212> TYPE: DNA
<213> ORGANISM: Mesembryanthemum crystallinum

<400> SEQUENCE: 33
ttatggaaac tcagcaacag gagagacaac aagaaacagc aaacccatca gcttcttcct     60
ctccatccca tgaattctcc ttcacacttt ctttacattc atcagaaaca cacccacaa     120 caacaacagc atcttcaaag accaaaaccg cgccgttggc tattgattta tccctgcag    180 atgacatctt cttccatggc caccttcttc ccctccactt cctgtctcat ctccaagccg    240
cgtcatcccc tcgctcttca atcaattccg tagacggcag cttcagcctc cccatgaagg    300
aactattgca agatcaggag aaaaaccag tcccctcctg tacttatcaa gtggctgcag    360
aggatcagac caataatgaa tatcaggtaa ctcataccgg aaactgtaac aagtcgaagc    420 ccccctttc tctcttcagt ctagcgaaat ggcggaaaca acaatccagc gaaatatcca    480
atgacagcga aaattacaat catcatcagc agcagcagca acagcagagg aggaagaaat    540
tgaagttcga tgtgagtcag tttctgaaga ggtatataaa catggttaag ccccttttgc    600
atctatacag gaaaagagag agagagagaa attagagtca ggggcagcct actccttctc    660
```

| | |
|---|---|
| gggggataac tcgccgcctg cgacgagagt tatcagaggc gcgcagaggg tgactctctg | 720 |
| cccagttcat gagacttccc cacaatacgg ctctatcgta ctgtggatc | 769 |

<210> SEQ ID NO 34
<211> LENGTH: 915
<212> TYPE: DNA
<213> ORGANISM: Nicotiana benthamiana

<400> SEQUENCE: 34

| | |
|---|---|
| cccctcaatc aaacaaaaac aagaaaactt gaaagaaaaa atatccaata ttagatctta | 60 |
| gtactaaatt tattacccct tttttaaaac atttttatag tcatggacaa gatgagagtc | 120 |
| aaagaagaat tgaagcaaaa caatcaagaa agccaaaagg caaagcaaat acaacagcaa | 180 |
| caaccaccac cctccgccgc tgccgccgcc accaccaccg ccggcggtcc agctccagct | 240 |
| tcaccacctt cagcttcatc atctccatca catgaatttt ctttcacaat tcctttaat | 300 |
| caaaatattt ccacaaaaac ccctgaaaat aataaaacaa agcaaaatac cccaccatct | 360 |
| tcttttgcta tagatttaac tccagctgat gatatatttt tccacggcca tttacttcct | 420 |
| cttcatcttc tttcacacct accagtttct cctcgctctt caacaaattc cgttgatagt | 480 |
| tcacttccca taaagatttt attagaagaa aaaaaaatcc aaaattccaa aaccaaaaa | 540 |
| gaattagaac atgatgatga taactcttat tatgatctaa accatagttt tcatcatcct | 600 |
| cgtcaaacaa attcttttac tacatcaaaa gatcaaaaac caaatccaa atcttttct | 660 |
| ttatttggat taccaaaaaa gaaaaagag gaaaagaag acaaggaaaa acaaggaag | 720 |
| ctaaaatttg atgtgagtca agtgttgaaa aggtatatga gaatggtgag accttttta | 780 |
| tcatttagaa gtagaaaaaa tatgcaattt aatagacaaa gttattctta ttctggtaat | 840 |
| ttaagtttta gaagtgggaa aaataaggaa attagaggaa taaaaagagg tgcatattca | 900 |
| gctccagtat ctatg | 915 |

<210> SEQ ID NO 35
<211> LENGTH: 809
<212> TYPE: DNA
<213> ORGANISM: Nicotiana tabacum

<400> SEQUENCE: 35

| | |
|---|---|
| taccttagca ccatttatac gagtatcgaa taccaagata agaaacaaaa aaaaaattca | 60 |
| aatgtgtcca ttcacgataa ttgccacata acacgcttat cataaaacat tttagttaca | 120 |
| aacaagtaac ctccccgtct tctcaccaaa ggaaagaccc atttttctca tatcccttat | 180 |
| cttttttgt tcttattttt gttgtccctt caaacaaaga gttgaagtag agaagtttga | 240 |
| gaaacaccac atcttaatta gatcttccta gcaatcttgt tacccctataa cattaacata | 300 |
| tatccatatg gacagccaat tacaccaaaa catgaaccac aaagaagaga aacagagaaa | 360 |
| tcaagaaagt gatcctcaca atggcagtag cagtactgca acctcaccac cacccttcatc | 420 |
| ttcatcatct ccttcacatg aattctcatt cactatttcc tttcaacaaa catctaattc | 480 |
| cacaatatca cctgcagata ataaaacaaa acaaatccaa acaccttctt catttgccat | 540 |
| agatttatct ccagctgatg atattttctt ccatggccac ttacttcccc ttcaccttct | 600 |
| ttcccatctc cccatttccc ctcgcacttc taccaattca atggatagtt ttactcttcc | 660 |
| aataaaagac catttttttg aagatcaaaa ggtccaaact tccaagaatc aaagagtatt | 720 |
| agatcatgag gacacttgtg atactactta tacatctaag ggaaaaccaa agggcaagtc | 780 |
| tttttccttg tttgggctac caaaaggga | 809 |

```
<210> SEQ ID NO 36
<211> LENGTH: 979
<212> TYPE: DNA
<213> ORGANISM: Phaseolus vulgaris
<220> FEATURE:
<221> NAME/KEY: misc_feature
<222> LOCATION: (501)..(501)
<223> OTHER INFORMATION: n is a, c, g, or t

<400> SEQUENCE: 36
aaccaattcc atggacagct tcaccctccc catcagagac ttattacaag atgaaaggca    60
ccccattaag gatagtggca gcaacagcac cacctcagac agcaacagca gcagcaaaag   120
agaccaacac aacaacagca acaacatagg aaaaaaggta caaggtaagt ccaaatttaa   180
cttttcattg tttggattag ccaagggggca aaaagggtgc caagatagta aggaggataa   240
agtgaagcac aagaagaagg caaggtttga tgtgatccat gcaatgaaaa agtacttgaa   300
aatggttcat cctaagatgc ttttcaaagg acaaagagag aagattagaa gtggacagtg   360
ttattcttat tcaggaaatg tcactccgag aaattacaaa cagggttgga gaggacaata   420
ttcagcacca gcatcaatga ggacttctcc aacaaatagt ggcctcttga ttgcaaccac   480
acctcttcct tcttctgcta nggacagtac catggaagag ttgcaagcag ccattcaagc   540
tgcaattgct cactgcaaaa attcaattgc aaaaaaagaa gaactcaaat gctgaatttt   600
tgtggtgtct tgttcaaaca caaatctgtt ccagacatgt tagaacacag aaactttctt   660
tcaacatgaa ctcgtaatct atgtaatacg aacactgaga tgaaaattga tactggtaca   720
agttgaattg agaattttgg tttcttaaga atgtatttcc taaatttgag gggaaattga   780
taatgatgct ttaaaatatg tcccttaaaa aacccggaat aattcgatta agtctagaat   840
cttgacaact gttttttta taaaaaaaa aaaggaggg cggctataat atctctgggg   900
cggccatatc ccccacctt ttttgaaaag ggccctttgg agggttttaa acacggcccg   960
gcgcggttaa aaaacgaag                                               979

<210> SEQ ID NO 37
<211> LENGTH: 665
<212> TYPE: DNA
<213> ORGANISM: Populus deltoides

<400> SEQUENCE: 37
ggcacgaggg catcctcctc tccttctcat gagttttcct tcacaatctc tctccactcc    60
gcctcagcac cagtccctga caaggtcaaa acccctccta attcatttgc tattgatttg   120
tctccagcag atgacatttt cttccatggg cacttgctcc ctctccatct cctctcacac   180
cttcctgtat ctcctcgctc gtccacaaat tcctttgaca gcttcaccct ccctatcaag   240
gaattattag atgatcaaag acccaacaaa agtagcaata actgcagcac cagcaatgga   300
aatagcataa gcagtagcag caacatcaac aacaacaata actgcagtcg ccatcgaagc   360
aaaaactata gtgagacaaa gggaagaagc aagcccaagt cttctctctt attcggttgg   420
cgaaaagggt gtgaagttaa agaaaaggag gaggacaagg gtgagcacaa gaaaagctg    480
aggttcgacg caagtcaggt actgaagagg tacgccagaa tggttaggcc actaatgttc   540
ttcaaaggaa ggagagaaaa tctccaatcc cacaggcaac cttattcatt ttcaggtaat   600
ttaagttggg gaaataaaca ggagttgcga gggacgagag gagaatgctc agcacctgca   660
tcgat                                                              665

<210> SEQ ID NO 38
```

-continued

```
<211> LENGTH: 685
<212> TYPE: DNA
<213> ORGANISM: Populus deltoides
<220> FEATURE:
<221> NAME/KEY: misc_feature
<222> LOCATION: (591)..(591)
<223> OTHER INFORMATION: n is a, c, g, or t

<400> SEQUENCE: 38
ggcacgaggt gacgactctc tctctctctc tctctctctc tctcccctc tctccactgc      60
tttctgatac ccttatcccc catcctcaaa ggtttggcaa tatttctcct ttattggtcc    120
aaaaataaga agtgttaga gctccacata ctggatcaga tcttattagt ctttcagtgt     180
aattctgtga attatggaca cccaaccgca agaaactcc agagaaaaag ttgtggacaa     240
gcctcgagaa gggaagttaa acaagaggg aaaagaaggc ctacaggcac agcaacaggc     300
actgccaaca tcccctgcct cgccaccttc agcttcctcc tctccttctc atgaattctc    360
cttcacaatc tctctccact cttcctccgc accagtacct gataaggcca aaacccctcc    420
taattctttt gctattgatt tgtctccggc ggatgacatt ttttccatg gccacctgct     480
tcctcttcat ctcctctcac accttcctgt atcccctcgc tcgtccataa attcctttga    540
cagctttacc ctccctatca aggatttatt agatgatcaa agacccaaca naagtggcaa    600
caactattgc agcaccagca acggaaatag cagtagcagt agcggtagcg gtagcagtag    660
caaccacgtc aaacacagca taact                                          685

<210> SEQ ID NO 39
<211> LENGTH: 664
<212> TYPE: DNA
<213> ORGANISM: Populus deltoides

<400> SEQUENCE: 39
agtggatcaa agaatcggca cgggaaaggt ttggcaatat ttctccttta ttggtccaaa     60
aataagaaag tgttagagct ccacatactg gatcagatct tattagtctt tcagtgtaat   120
tctgtgaatt atggacaccc aaccgcaaag aaactccaga gaaaagttg tggacaagcc    180
tcgagaaggg aagttaaaac aagagggaaa agaaggccta caggcacagc aacaggcact   240
gccaacatcc cctgcctcgc caccttcagc ttcctctct ccttctcatg aattctcctt    300
cacaatctct ctccactctt cctccgcacc agtacctgat aaggcaaaa ccctcctaa     360
ttcttttgct attgatttgt ctccggcgga tgacattttt ttccatggcc acctgcttcc   420
tcttcatctc ctctcacacc ttcctgtatc ccctcgctcg tccataaatt cctttgacag   480
ctttacccctc cctatcaagg atttattaga tgatcaaaga cccaacaaaa gtggcaacaa   540
ctattgcagc accagcaacg gaaatagcag tagcagtagc ggtagcggta gcagtagcaa   600
ccacgtcaac aacagcaata actgcaatca ccatcaaagc aataactata gcgatacaaa   660
ggga                                                                664

<210> SEQ ID NO 40
<211> LENGTH: 855
<212> TYPE: DNA
<213> ORGANISM: Populus trichocarpa
<220> FEATURE:
<221> NAME/KEY: misc_feature
<222> LOCATION: (729)..(729)
<223> OTHER INFORMATION: n is a, c, g, or t

<400> SEQUENCE: 40
cactctgcct cagcaccagt ccctgacaag gccaaaaccc ctcctaattc atttgctatt     60
```

-continued

```
gatttgtctc cagcagatga catttcttc catgggcact tgctccctct ccatctcctc    120
tcacaccttc ctgtatctcc tcgctcgtcc acaaattcct tgacagctt caccctccct    180 atcaaggaat tattagatga tcaaagaccc aacaaagta gcaataactg cagcaccagc    240
aatggaaata gcattagcag tagcaacaac atcaacaaca acaattactg tagtcgccat    300
cgaagcaaaa actatagtga gacgaaggga agaagcaagc ccaagtcttt ctctttattc    360
ggttggcgaa aagggtgtga agttaaagaa aggaggagg acaagggtga gcacaagaaa     420
aagctgaggt tcgacgcaag tcaggtactg aagaggtacg ccagaatggt taggccacta    480
atgttcttca aaggaaggag agaaaatctc caatcccaca ggaaaccta ttcattttca     540 ggtaatttaa gttggggaaa taaacaggag ttgcgaggga cgagaggaga atgctcagca    600
ccggcatcga tgaggacatc tccaacaaat agtggccttc ttcttgcaac tgcaactctt    660
cctacttcta ctagtgatag tacaatggaa gagtttcatg ctgctattca agcagcaatt    720
gctcattgnc agaactccat tgctgcagaa gaaaagatga aatgctaaat gttagactgg    780
acttccgatt ttctcctgtt gaatttctat ttcttatacc tgtgcataaa ttaaagtact    840
atatatatat atata                                                    855

<210> SEQ ID NO 41
<211> LENGTH: 925
<212> TYPE: DNA
<213> ORGANISM: Populus trichocarpa

<400> SEQUENCE: 41 ttttttttt ttttttttgg acaagtaagc atgaaacttt attcttaaat gctgtaatct     60
tttgatacca tcttgagatt gtcaaactcg tttcataact ctctctctca aactcgtttc    120
ataactctct ctctctctct ctcatatata tatatatata tatatatata tatagtactt    180 taattatgc acaggtataa gaaatagaaa ttcaacagga gaaatcgga agtccagtct      240 aacatttagc atttcatctt ttcttctgca gcaatggagt tcttgcaatg agcaattgct    300
gcttgaatag cagcatgaaa ctcttccatt gtactatcac tagtagaagt aggaagagtt    360
gcagttgcaa gaagaaggcc actatttgtt ggagatgtcc tcatcgatgc cggtgctgag    420
cattctcctc tcgtccctcg caactcctgt ttatttcccc aacttaaatt acctgaaaat    480
gaataaggtt tcctgtggga ttggagattt tctctccttc ctttgaagaa cattagtggc    540
ctaaccattc tggcgtacct cttcagtacc tgacttgcgt cgaacctcag cttttttcttg   600 tgctcaccct tgtcctcctc cttttcttta acttcacacc cttttcgcca accgaataaa    660
gagaaagact tgggcttgct tcttcccttc gtctcactat agtttttgct tcgatggcga    720
ctacagtaat tgttgttgtt gatgttgttg ctactgctaa tgctatttcc attgctggtg    780
ctgcagttat tgctacttt gttgggtctt tgatcatcta ataattcctt gatagggagg    840
gtgaagctgt caaggaatt tgtggacgag cgaggagata caggaaggtg tgagaggaga    900
tggagaggga gcaagtgccc atgga                                         925

<210> SEQ ID NO 42
<211> LENGTH: 585
<212> TYPE: DNA
<213> ORGANISM: Prunus persica

<400> SEQUENCE: 42
caaagactta tcagatgatg atcagagacc aaccaaagaa agcaacaaca atgctaacaa     60
ctgcagcacc agcattggca ggaacaagaa tatcatcaac aacaagaaca acagctgccg    120
```

```
cagcataaac cagataagcc cacatcacag caacaaaagt gaggcaaggg gaagaacaaa    180
gtccaagtct ttctcattat tcgggttacc aaaatggcga aaagattgtg aagacagaga    240 aaagaagac aaggagatga agcacaagag gaagatgagg tttgatgtga gccatatact     300
aaagaggtat gtgagaatgg tcaggccact attgttattc agaggaagaa aagagaaggg    360
ccaattccgg aggcaacctt attcgttttc gggcaatcta agcttgagaa ataagcatga    420
gctgagagga aggagaggag agctttcagc cccagcatca atgagaacat ctccaacaaa    480
tagtggcctt cttgttgcaa catcagcaac taatcttcct tcttccacca ttgacagcac    540
catggaagag ttgcaggcag caattcaagc tgcaattgct cattg                   585

<210> SEQ ID NO 43
<211> LENGTH: 835
<212> TYPE: DNA
<213> ORGANISM: Solanum tuberosum

<400> SEQUENCE: 43
gaacatcaaa tcttgaagaa aaataaaaac acccaatatt agatcttagt ataaatttta     60
ttttattacg ttcttttaac attttttttta aagtcatgga taatatgaga gttggagaac    120
aagaattgaa gcagagcaat aaagaaaacc agaaaacaga gccaccacag tccggcggtg    180
gtgctgcggt gtcaccaccg tcagcttcat catctccggc gcatgagttc tccttcacaa    240
tttcacttca cccaacaaat tccacaaaag cccttgaaag taaaaccaaa caaaatctga    300
atccgaactt gaacccgaac ccgaacccga atcagaaccc atccgccatt gatttaactc    360
cagctgatga atttttcttc catggccatt tacttcctct tcatcttctt tcccatcttc    420
ctgtttcgcc tcgctcttca acaaattcca ttgacagttc aatccccatt agtaaatcag    480
aacaaaaaat ccaaaaatcc attaatcagt tagatgatga tgatgatgat aattcttatt    540
atgatttaaa ccatagtttt catcatcatc ccgaaacaac aaattcattt aacatacca     600 aagatcaaaa acccaaatcc aaatcttttt ccatatttgg attacccaaa cgaaaaaag     660 gcgaaaagga tgagaaagaa aaacagagga agctgaaatt cgatgtaagt caagttttga    720
aaaggtatat gagaatggtg agaccatttt tatcatttgg aagcagaaaa aatatgcaat    780
ttcatagaca aagttattca tattctgcga aattgagttt tcgaggaaag aatac         835

<210> SEQ ID NO 44
<211> LENGTH: 687
<212> TYPE: DNA
<213> ORGANISM: Thellungiella salsuginea

<400> SEQUENCE: 44
atcatggaaa cccatctaca gcaggtgaag aacagttctc aaacttttc tgaaaagcaa       60 aaccctaaac aagaagcttc accaatatca tccacttctt cttcacctc tcatgacttc      120 tccttcacca tctctctcca acctctatct tcttcctcca aaatcattag ccctacactc     180
agaaacccaa ccaaaacgac accgtcttac caacaaaccg atccattcgc tgtcgatctg     240
tctcctgccg atgagatctt cttctacggc catcttctcc ctctccatct tctctctcac     300
ctccctgtct ctcccgaac ttccaccggt tcgtataatg acggatttgc cctccctgtc     360
aaagatatat tacctgacca gcccaccact ctccccacca caaacgacga caacaacaac    420
aacaacagta tggagctgaa gaatagcaat accgacgata agtcccagag attcgacagt     480
gagaatcgag ttaaaaccaa acccataaag tcatttttctc tctttggttt atcgaaatgg    540
agaaaagggt atgaaggcaa cgaccgagga caagagcagc aacaacaaaa ccagcagcag    600
```

```
aagaagaaac ttagtttaga cctaagtcac gcagtcaaga agtacataag gatgttgttt      660
cagagaagag gaaacggcat gcagttc                                          687

<210> SEQ ID NO 45
<211> LENGTH: 582
<212> TYPE: DNA
<213> ORGANISM: Trifolium pratense

<400> SEQUENCE: 45
ctccattcta attccaaacc atcaccttct tcttctcttg cacttgattt atcaccagct       60
gatgacattt tctttcatgg tcatttatta ccacttcatc tcctctctca ctttccttcc      120
tcgccgcgct tttcaactaa ttcaaatgat agtttcaccc ttcctatcag agacttagaa      180
aatgaaaaga ttagaagaga cgccggaagt tgcaacacta gcaacaggga aaacatctac      240
aataacaata gtagaggaat tattacaaag gaagaaaata ggtcgaattc gcatggcgca      300
aaagctagta gtttctcatt gtttggattg acaaaaggaa atcataataa agagaattcg      360
aagccgcaga ataagaagaa agttgttgga tatgatgtta tacaagcatt aaaaaagtac      420
ttttttagag gtaaaagaga aaagaatcaa tttcatggag aagcttattc acgttcaggt      480
aatttaatga gaaaaaataa gccagaatta agaggaagta gaggagaata ttcagcacca      540
gcttcaatga gaacttctcc aacaaatagt ggattattgc tt                         582
```

COMPOSITIONS, CELLS, AND PLANTS THAT INCLUDE BKI1, A NEGATIVE REGULATOR OF BRI1-MEDIATED BR SIGNALING

CROSS REFERENCE TO RELATED APPLICATIONS

This application claims priority to and benefit of U.S. Ser. No. 60/879,867, filed Jan. 10, 2007, which is incorporated herein by reference in its entirety.

STATEMENT OF GOVERNMENT RIGHTS

This work was supported by a grant from the National Research Initiative of the USDA, grant number 2002-35301-12010. The government may have certain rights in the invention.

FIELD OF THE INVENTION

The field of the invention relates to brassinosteroid regulation in plants. The activity of a negative brassinosteroid regulator, BKI1, is described. It is shown that dissociation of BKI1 from the plasma membrane involves both brassinosteroids and activity of the major brassinosteroid receptor (BRI1).

BACKGROUND

Brassinosteroids comprise a class of more than 40 plant polyhydroxylated sterol derivatives that regulate, e.g., the size and architecture of plants. The brassinosteroids regulate cell elongation, vascular development, stress tolerance, seed size, leaf erectness, fertility, flowering time, senescence, yield, and many other traits of interest. Brassinosteroid regulation pathways are complex, and include, e.g., negative regulation of brassinosteroid synthesis genes in the presence of brassinosteroids, as well as a variety of positive and negative responses to brassinosteroids in a wide variety of steroid responsive genes. Brassinosteroid levels are an attractive target for manipulation, to control agricultural yield and other agriculturally significant traits. In fact, exogenous application of brassinosteroids has been used in some applications to increase yield or to influence other quantitative traits of interest.

Relatively recently, several of the molecular components of the brassinosteroid synthesis and signaling pathways have been identified. For example, BRI1, the major brassinosteroid receptor of *Arabidopsis* (2-4), has been studied using loss-of-function mutants, over-expression, and biochemical analyses to identify the activation and specificity of receptor-like-kinases (5). Brassinosteroids control physiological and developmental processes such as stem elongation, vascular differentiation, seed size, fertility, flowering time, senescence, and resistance to biotic and abiotic stresses (2, 6, 7). Direct binding of brassinolide, the most active brassinosteroid, to the extracellular domain of BRI1 activates a preformed homo-oligomer. Auto- or trans-phosphorylation of the C terminus of BRI1 then enhances kinase activity and the affinity of BRI1 for BAK1, its proposed co-receptor (8-11). A version of BRI1 lacking the 41 C-terminal amino acids is a more active receptor but cannot be fully activated, suggesting that other factors are also required to regulate BRI1 activity.

Downstream from BRI1 and BAK1, BIN2, a glycogen synthase kinase-3 family member (12), negatively regulates brassinosteroid signaling by phosphorylating members of a plant-specific family of transcriptional regulators, defined by the BES1 and BZR1 genes (13-16). In the presence of brassinosteroids, BIN2 is inhibited, leading to the dephosphorylation of BES1 and BZR1. Dephosphorylated BES1 and BZR1 then homo-dimerize or cooperate with other transcription factors, which allows DNA binding and regulation of hundreds of brassinosteroid-responsive genes (15-17).

Accordingly, the ability to regulate the brassinosteroid pathway, to influence many different agricultural traits of interest, is of considerable value to commercial agriculture. The present invention provides new mechanisms for regulating the brassinosteroid pathway. These and other features are discussed in detail below.

SUMMARY OF THE INVENTION

BKI1 (BRI1 kinase inhibitor 1) is a plasma membrane-associated phosphoprotein that interacts directly with the kinase domain of BRI1. When present in the plasma membrane, BKI1 interferes with an interaction of BRI1 with its signaling partner, a second plasma membrane-localized leucine rich repeat receptor kinase called BAK1 (BRI1-associated receptor kinase 1, also known as SERK3 (somatic embryogenesis receptor kinase 3). Control of BK1 expression and/or activity provides a mechanism for regulating the brassinosteroid pathway.

Accordingly, the invention includes transgenic plants that express a recombinant BKI1-type polypeptide. A variety of example polypeptides are available, including BKI1 type polypeptides/coding nucleic acids that include a sequence found in GeneBank at accession number: AJ796385.1 (SEQ ID NO:20), AJ796560.1 (SEQ ID NO:21), CX674446.1 (SEQ ID NO:22), DY389957.1 (SEQ ID NO:23), BU579318.1 (SEQ ID NO:24), BE609508.1 (SEQ ID NO:25), BE609498.1 (SEQ ID NO:26), AW620804.1 (SEQ ID NO:27), DY946533.1 (SEQ ID NO:28), BJ557111.1 (SEQ ID NO:29), BJ575601.1 (SEQ ID NO:30), DY971277.1 (SEQ ID NO:31), BQ867285.1 (SEQ ID NO:32), BE130683.1 (SEQ ID NO:33), CK287132.1 (SEQ ID NO:34), EB435640.1 (SEQ ID NO:35), BQ481779.1 (SEQ ID NO:36), CX170112.1 (SEQ ID NO:37), CX175441.1 (SEQ ID NO:38), CX175253.1 (SEQ ID NO:39), DT481968.1 (SEQ ID NO:40), DT487361.1 (SEQ ID NO:41), DY636517.1 (SEQ ID NO:42), CX162638.1 (SEQ ID NO:43), DN773886.1 (SEQ ID NO:44), or BB923413.1 (SEQ ID NO:45). The polypeptide can be a full-length protein, or a fragment thereof, and can be coupled to one or more heterologous sequences.

Typically, recombinant BKI1-type polypeptide binds to a kinase domain of a BRI1-type protein, repressing brassinosteroid signaling in the transgenic plant. The transgenic plant optionally additionally expresses one or more recombinant modulators that modulate expression of the recombinant BKI1-type polypeptide, or of an endogenous bki1-type gene in the plant, or both. The modulator and/or the recombinant BKI1-type polypeptide can display constitutive or tissue-specific expression and/or can be developmentally controlled. Controlling which tissues express recombinant BKI1-type polypeptides or modulators can provide for selective control of brassinosteroid response in selected tissues and/or developmental stages of the transgenic plant.

Optionally, the modulator and recombinant BKI1-type polypeptide can display non-identical patterns of tissue-specific expression in the plant, e.g., where inhibition of brassinosteroid response is desired in one tissue, while potentiation of the response is desired in another.

Accordingly, in a related aspect, the invention includes a transgenic plant that comprises a recombinant modulator that modulates expression of a bki1-type gene. Example modulators include RNAi or antisense molecules that inhibit translation of an mRNA that encodes a BKI1-type polypeptide. The modulator optionally reduces expression of a BKI1-type polypeptide encoded by the gene by about 50% or more in the plant. Typically, the modulator inhibits expression of a BKI1-type polypeptide in the transgenic plant, thereby derepressing brassinosteroid signaling in the transgenic plant.

As noted, recombinant BKI1 polypeptide or modulators thereof can display tissue specific expression. For example, the tissue-specific expression of the polypeptide or modulator can include or result in a higher level of expression of the recombinant BKI1-type polypeptide in leaves of the plant than in seeds of the plant. As a result, for example, the plant optionally displays a decreased response to brassinolide in at least one tissue of the plant.

For example, the decreased response can include reduced expression of one or more genes in the tissue that are expressed in response to brassinolide; increased expression of brassinosteroid synthetic genes in the tissue that are repressed by brassinolide, or the like. typically, the transgenic plant displays increased or reduced expression of at least one brassinosteroid responsive gene as compared to a control plant, in at least one plant tissue.

Expression of the BKI1-type polypeptide or modulator optionally induces a phenotype in the transgenic plant selected from the group consisting of: decreased sensitivity to brassinosteroids, increased sensitivity to brassinosteroids, improved yield under dense planting conditions, increased leaf erectness, stress tolerance, increased tolerance to biotic or abiotic stress, decreased tolerance to biotic or abiotic stress, enhanced dwarfism, increased stature, decreased stature, increased stem length, decreased stem length, altered vascular differentiation, increased seed size, decreased seed size, increased fertility, decreased fertility, increased time to senescence, decreased time to senescence, increased hypocotyl length, decreased hypocotyl length, accelerated flowering, delayed flowering, increased petiole length, decreased petiole length, increased cell elongation, decreased cell elongation, rounded leaves, and combinations thereof.

Most typically, the plant is an angiosperm. For example, the plant can be a monocot or a dicot. For example, the plant can be a member of a plant family selected from: the Orchidaceae, the Asteraceae or Compositae, the Fabaceae or Leguminosae, the Poaceae or Gramineae, the Rubiaceae, the Euphorbiaceae, the Malvaceae, the Cyperaceae or Araceae. For example, the plant can be a member of a species found in the *Agrostis, Allium, Antirrhinum, Apium, Arabidopsis, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setria, Sinapis, Soanum, Sorghum, Stenotaphrum, Theobroma, Trifolium, Trigonella, Triticum, Vicia, Vigna, Vitis, Zea,* the Olyreae, and/or the Pharoideae. For example, the plant can be a member of a species such as: *Antirrhinum majus, Citrus sinensis, Curcuma longa, Glycine max, Helianthus petiolaris, Ipomoea nil, Lettuce sativa, Mesembryanthemum crystallinum, Nicotiana benthamiana, Nicotiana tabacum, Phaseolus vulgaris, Populus deltoids, Populus trichocarpa, Prunus persica, Solanum tuberosum, Thellungiella salsuginea,* and *Trifolium pratense*. In one preferred class of embodiments, the plant is a barrelclover, a turfgrass, a forage plant, a cotton, a *Glycine max,* a *Zea mays,* a Sunflower, a *Sorghum,* a Wheat, a Rice, a barley, a tomato, a oil rape, or a Canola plant.

In a related aspect, the invention includes a recombinant cell that includes an expression vector that encodes a BKI1 type polypeptide, a modulator of a bki1-type gene, or both. The cell is typically a recombinant plant cell, e.g., where the cell is a cell of a recombinant plant. All of the features noted above with respect to particular polypeptides, plant types, etc., are equally applicable to this class of embodiments.

In another aspect, the invention includes a recombinant BKI1-type polypeptide that includes an exogenous polypeptide domain, or an non-polypeptide domain. For example, the exogenous polypeptide domain can include a purification, labeling or other functional domain from one or more heterologous source. Examples include a membrane anchoring domain, a FLAG tag, a fluorescent polypeptide domain, a polyhistidine tag, a HIS-6 tag, a His-10 tag, a biotin, an avidin sequence, a GST sequence, a glutathione, a BiTag, an S tag, an antibody, an antibody domain, an antibody fragment, an antigen, a receptor, a receptor domain, a receptor fragment, a ligand, a dye, an acceptor, and a quencher. Typically, the recombinant polypeptide binds to a BRI1-type polypeptide. The exogenous domain can increase or decrease repression of a brassinosteroid response as compared to a corresponding BKI1-type polypeptide that lacks the domain. In a related aspect, the invention include a complex comprising a BKI1 type polypeptide, a BRI1 type polypeptide and an exogenous label or purification tag. All of the features noted above with respect to appropriate BKI1 type polypeptides, etc., are applicable to these classes of embodiments as well.

Also provided are recombinant nucleic acids comprising a bki1-type promoter operably linked to an exogenous nucleic acid sequence. The exogenous nucleic acid sequence can encode, e.g., a reporter, useful, e.g., for monitoring bki1 promoter activity in one or more tissues of interest. An example reporter includes β-glucuronidase (GUS). Cells and plants, e.g., as discussed above, that include the nucleic acid are also a feature of the invention.

In addition to cells, plants, nucleic acids and polypeptides, the present invention includes a variety of methods. In general, the features of the cells, plants, nucleic acids, polypeptides and other compositions already discussed can be incorporated in the methods herein.

In one example, the invention includes methods of modulating a brassinosteroid response in a cell. The methods include, e.g., modulating expression or activity of a BKI1-type polypeptide or gene in the cell. Expression or activity of the BKI1-type polypeptide or gene modulates brassinosteroid response in the cell, thereby modulating the brassinosteroid response in the cell. The brassinosteroid response can include activation or repression of one or more brassinosteroid responsive genes in the cell, modulated, e.g., by overexpressing a nucleic acid that encodes a BKI1-type polypeptide or modulator in the cell.

Overexpressing the bki-1 type gene optionally includes recombinantly expressing the gene in the cell. Alternately or in addition, modulating expression can include inhibiting expression of the BKI1 type polypeptide or gene by co-expressing an RNAi or antisense molecule that inhibits translation of an mRNA that encodes the BKI1 type polypeptide.

In a related class of embodiments, methods of modulating a plant phenotype are provided. These include expressing a recombinant BKI1-type polypeptide in the plant, thereby modulating the phenotype of the plant. The BKI1-type polypeptide optionally binds to a kinase domain of a BRI1-type protein, thereby repressing brassinosteroid signaling in the transgenic plant.

In another related class of embodiments, additional methods of modulating a plant phenotype are provided. These methods include, e.g., expressing or applying a modulator to the plant. The modulator modulates expression or activity of a bki1-type nucleic acid or a BKI1-type polypeptide, thereby modulating the phenotype of the plant. The modulator is a modulator other than a brassinosteroid, e.g., an RNAi or antisense molecule that inhibits expression of a bki1-type nucleic acid. Optionally, the method includes recombinantly expressing the modulator in the plant.

Optionally, the methods above can additionally include detecting reduced expression of one or more genes in the plant that are expressed in response to brassinolide; detecting increased expression of brassinosteroid synthetic genes in the plant that are repressed by brassinosteroid-mediated signaling, or other related aspects. The methods can also include detecting increased or reduced expression of at least one brassinosteroid responsive gene as compared to a control plant that does not comprise the modulator or BKI1-type polypeptide.

In the methods, expressing the recombinant BKI1-type polypeptide or modulator can optionally include introducing a nucleic acid encoding the BKI1-type polypeptide or modulator into a plant cell or protoplast, and culturing the cell or protoplast to form a recombinant plant. The methods can also, optionally, include selecting a plant expressing the polypeptide or modulator for at least one phenotype of interest. Example phenotypes for selection include: decreased sensitivity to brassinosteroids, increased sensitivity to brassinosteroids, improved yield under dense planting conditions, increased leaf erectness, stress tolerance, enhanced dwarfism, increased stature, decreased stature, increased hypocotyl length, decreased hypocotyl length, accelerated flowering, delayed flowering, increased petiole length, decreased petiole length, increased cell elongation, decreased cell elongation and rounded leaves. Any nucleic acid that encodes a modulator or BKI1 type polypeptide can be introgressed into an elite crop line or cultivar. Any of the methods can optionally further include administering a brassinosteroid to the plant, e.g., to achieve a desired phenotype.

BRIEF DESCRIPTION OF THE FIGURES

FIG. 2 includes panels A-J. FIG. 2 C-E are photographs showing phenotype of plants overexpressing BKI1-FLAG, with Col-0 (left) and a BKI1-FLAG line (right).

FIG. 3A-R are photomicrographs. In FIG. 3A, BKI1-YFP is localized to the plasma membrane and cytosol on MS medium. In FIG. 3B, BRZ220 enhances the association of BKI1-YFP to the plasma membrane. Seedlings were grown on MS medium containing 1 μM BRZ220. In FIG. 3C, BL enhances BKI1-YFP dissociation from the plasma membrane. Seedlings were grown on MS medium containing 1 μM BL. As shown in FIG. 3D-F, DMSO (0.001% (v/v)) does not alter the plasma membrane localization of BKI1-YFP. FIG. 3 G-I show BL-induced dissociation of BKI1-YFP from the plasma membrane. Seedlings were grown on MS medium containing 1 μM of BRZ220 and treated with 1 μM BL. FIG. 3 J-L show that BKI1-YFP is associated with the plasma membrane in bri1-116. Seedlings were grown on MS medium containing 1 μM of BRZ220. bri1-116 is a null allele of BRI1 (19). As shown in FIG. 3 M-O, BL does not cause dissociation of BKI1-YFP from the plasma membrane in bri1-116. Seedlings were grown on MS medium containing 1 μM BL. FIG. 3 P-R show that an active kinase is required for BL-induced dissociation of BKI1 from the plasma membrane. bri1-104 is a loss-of-function mutation in the kinase domain of BRI1 (19). Seedlings were grown on MS medium containing 1 μM BRZ220.

3D, G, J, M, and P are untreated; E, H, K, N, and Q are treated with BL for 5 min, and F, I, L, O, and R are treated with BL for 10 min.

Figure 4D:
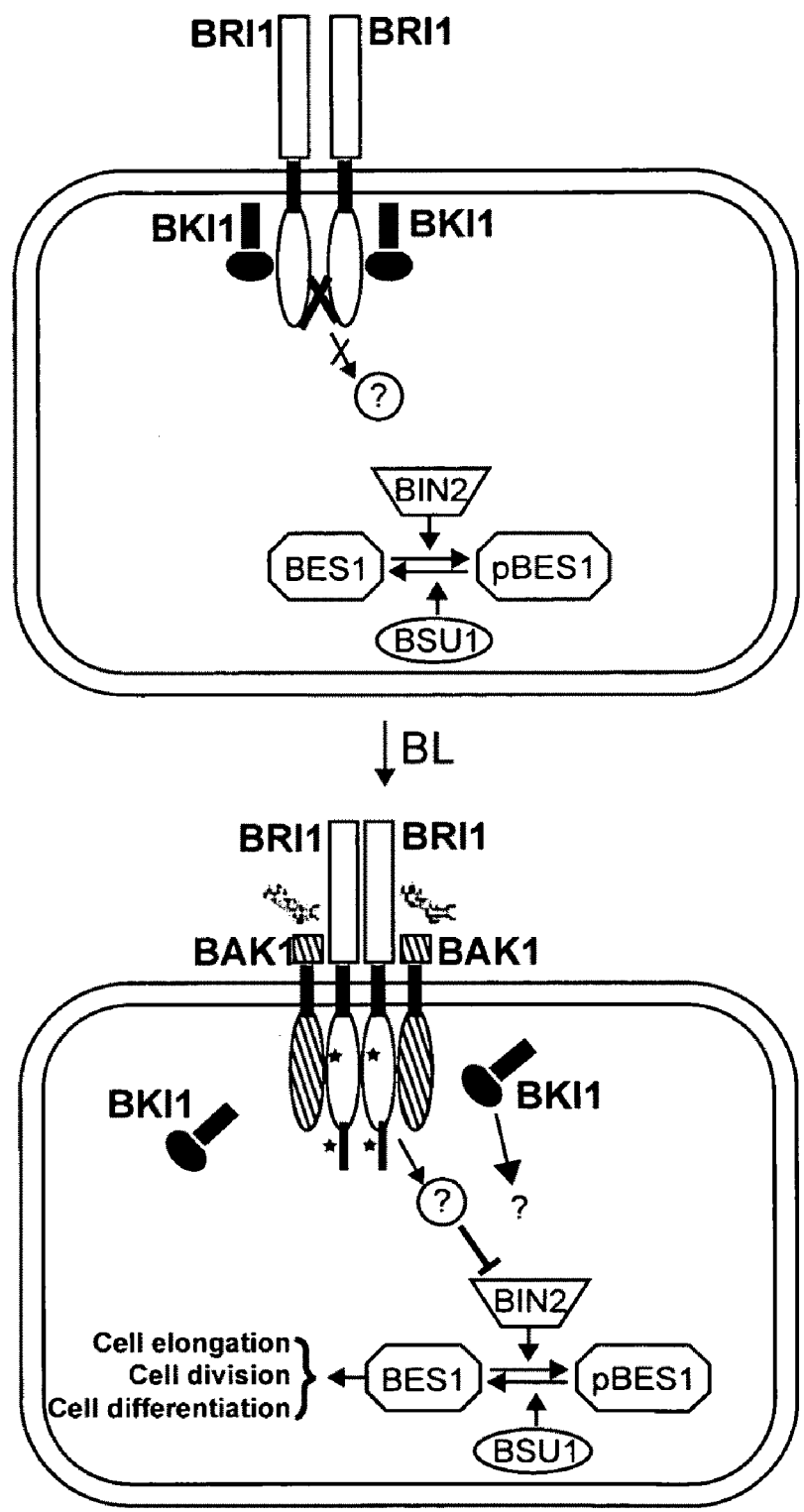

FIG. 4 includes panels A-D. FIG. 4A includes a set of photomicrographs showing that a myristoylated BKI1-YFP is constitutively associated with the plasma membrane following BL treatment. Seedlings were grown on MS medium containing 1 μM of BRZ220. The time of BL treatment is indicated. Top panels: BKI1-YFP; Lower panels: myriBKI1-YFP. FIG. 4B includes a photograph and an immunoblot showing that over-expression of a myristoylated BKI1-YFP (myriBKI1-YFP) leads to an enhanced dwarf phenotype. Immunoblots with anti-GFP show levels of myriBKI1-YFP and BKI1-YFP. Bottom band: loading control. FIG. 4C includes a histogram showing that BKI1 inhibits the interaction between the kinase domains of BRI1 and BAK1 in vitro. The total $^{35}$S-Met labeled BRI1-KD-HIS co-precipitated by GST-BAK1-KD was defined as "1". Five replicates were conducted. Error bars indicate standard error. 1, GST-BAK1-KD+35S-BRI1-KD-HIS; 2, GST-BAK1-KD+35S-BRI1-KD-HIS+10 μM of MBP; 3, GST-BAK1-KD+35S-BRI1-KD-HIS+10 μM of MBP-BKI1. The bottom panel shows a representative gel by autoradiography, indicating the pull-down $^{35}$S-Met labeled BRI1-KD-HIS. FIG. 4D shows a schematic model to illustrate the role of BKI1 in BRI1 signaling. As shown, without BL, BRI1 kinase is kept in a basal state by both its own carboxyl terminal domain and by an interaction with BKI1. Brassinosteroid binding to the extracellular domain of BRI1 induces a conformational change of the kinase domain, leading to the phosphorylation of the C-terminal domain of BRI1 and BKI1, the dissociation of BKI1 from the plasma membrane, and the release of autoinhibition of BRI1. These events lead to the full activation of BRI1 and its association with BAK1 or other substrates. Plasma membrane-dissociated BKI1 may also regulate other unknown components in the brassinosteroid signaling cascade. BSU1 is a nuclear serine/threonine phosphatase involved in the dephosphorylation of BES1.

Figure 5:
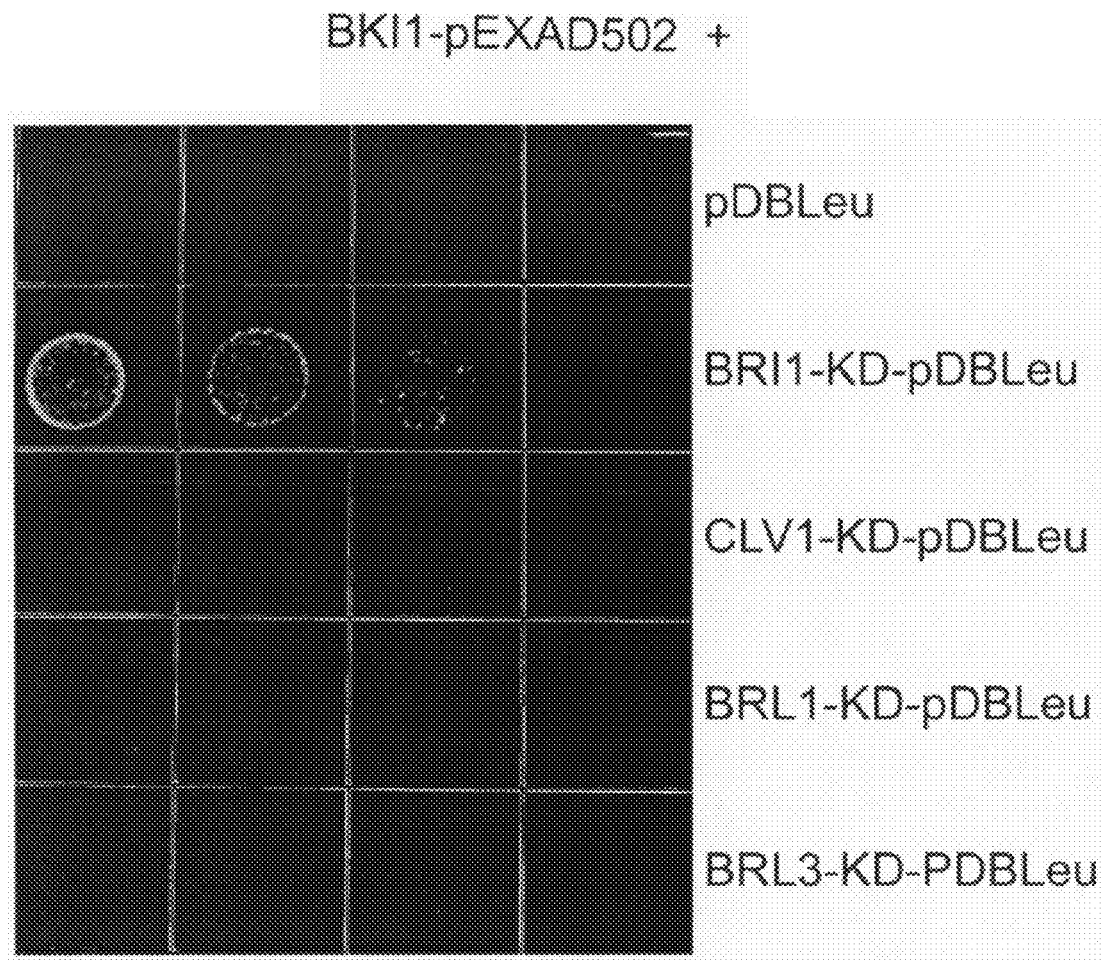

FIG. 5 is a photograph showing that BKI1 does not interact with the kinase domains of CLV1, BRL1, or BRL3. BKI1 fused with GAL4-AD (BKI1-pEXAD502) interacts with the intracellular domain of BRI1 (BRI1-KD), but not CLV1 (CLV1-KD), BRL1 (BRL1-KD), and BRL3 (BRL3-KD), fused with GAL4-DB (in pDBLeu) in yeast. pDBLeu was used as a negative control. Each spot from left to right contains 10 μl yeast cell culture with $OD_{600}$=0.2, 0.04, 0.008, and 0.0016.

Figure 6:
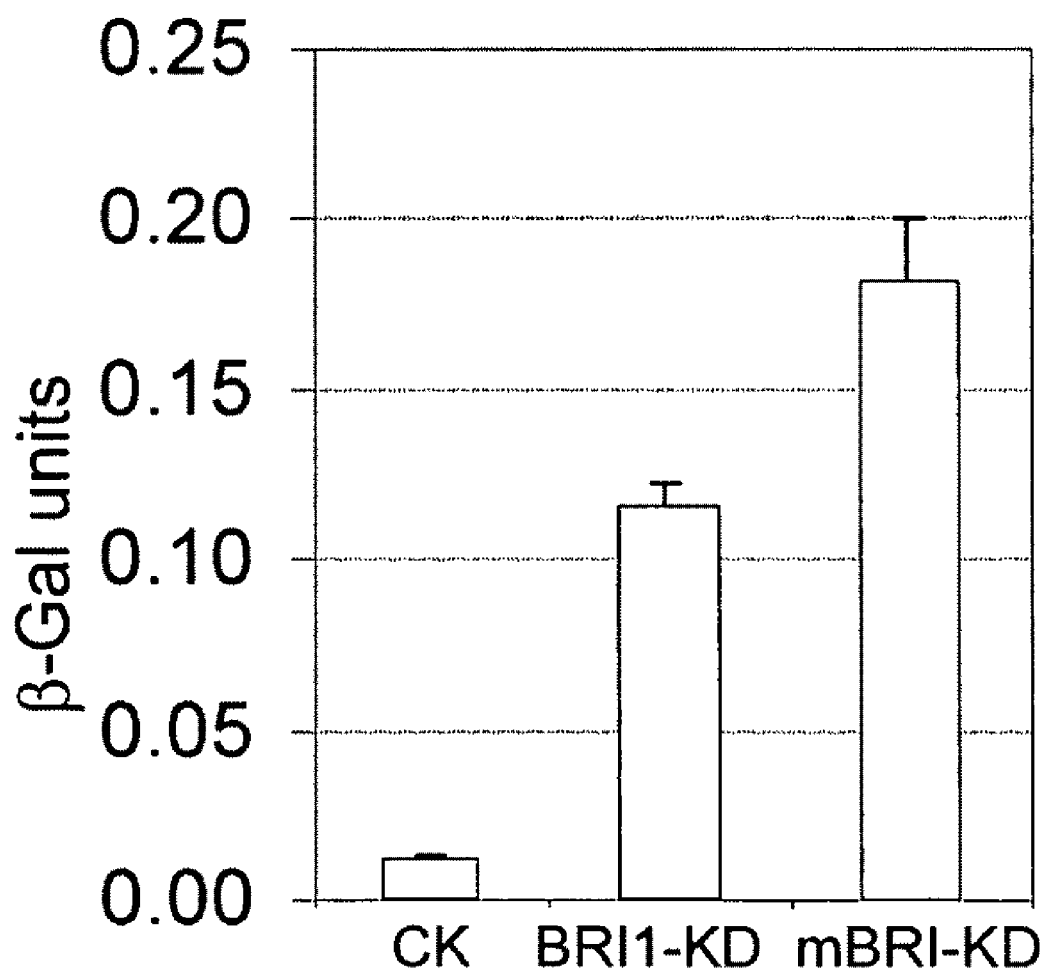

FIG. 6 is a histogram showing the interaction of BKI1 with pDBLeu (CK), the intracellular domain of wild type BRI1 (BRI1-KD), and kinase-inactive BRI1 (mBRI1-KD) measured with a liquid culture assay using o-Nitrophenyl-β-D-Galactopyranoside (ONPG) as a substrate.

Figure 7A:
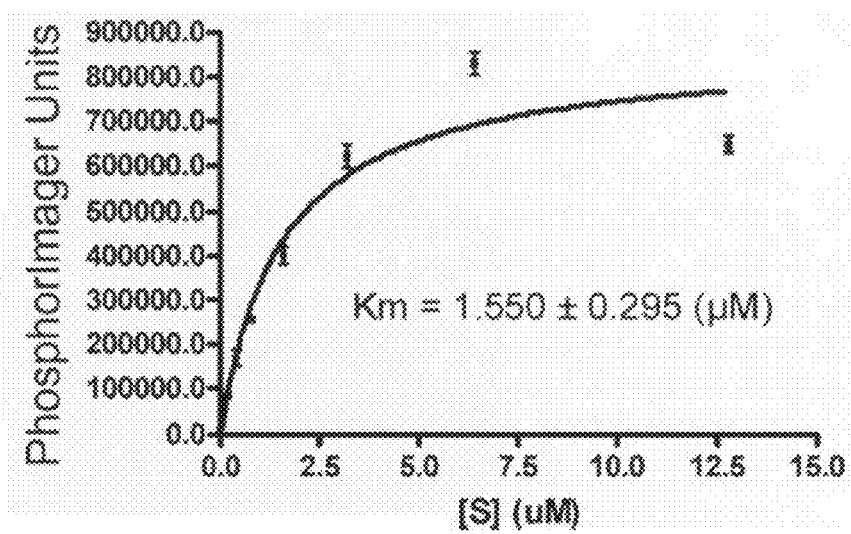
Figure 7B:

FIG. 7A is a graph showing that MBP-BKI1 can be highly phosphorylated by BRI1 kinase in vitro. FIG. 7B is an autoradiogram showing that BKI1-FLAG is a phosphoprotein in planta.

DETAILED DESCRIPTION OF THE INVENTION

Brassinosteroids (BRs) are polyhydroxylated steroid plant hormones involved in regulatory pathways that influence a variety of significant plant traits, including yield, stress response, plant size and plant architecture. For a current introduction to the topic, see, for example, Belkhadir and Chory (2006) "Brassinosteroid Signaling: A Paradigm for Steroid Hormone Signaling from the Cell Surface" *Science* 314 (5804): 1410-1411; Wang and Li (2006) "Genes controlling plant architecture" *Current Opinion in Biotechnology* 17:1-7; Karlova and de Vries (2006) "Advances in Understanding Brassinosteroid Signaling" *Sci. STKE,* 2006(354): pe36; Li J (2005) "Brassinosteroid signaling: from receptor kinases to transcription factors" *Curr Opin Plant Biol* 8:526-531; Wang and He (2004) "Brassinosteroid signal transduction—choices of signals and receptors" *Trends Plant Sci* 9:91-96; Fujioka and Yokota (2003) "Biosynthesis And Metabolism Of Brassinosteroids" *Annu. Rev. Plant Biol.* 54:137-164; Lindsey et al. (2003) "Importance of plant sterols in pattern formation and hormone signaling" *Trends Plant Sci* 8:521-525; and Schaller (2003) "The role of sterols in plant growth and development" *Prog Lipid Res* 42:163-175.

BRI1 is the major brassinosteroid steroid receptor in *Arabidopsis*. In the absence of BRs, the activity of BRI1 is inhibited by both cis and trans mechanisms. It is discovered herein that BKI1 (BRI1 kinase inhibitor 1) is a plasma membrane-associated phosphoprotein that interacts directly with the kinase domain of BRI1. Without being limited to any particular theory of operation, it is believed that binding of BRs to preformed BRI1 homooligomers triggers the rapid dissociation of BKI1 from the plasma membrane. When present in the plasma membrane, BKI1 interferes with an interaction of BRI1 with its signaling partner, a second plasma membrane-localized leucine rich repeat receptor kinase called BAK1 (BRI1-associated receptor kinase 1, also known as SERK3 (somatic embryogenesis receptor kinase 3) (Belkhadir and Chory (2006) "Brassinosteroid Signaling: A Paradigm for Steroid Hormone Signaling from the Cell Surface" *Science* 314 (5804): 1410-1411; Wang and Chory (2006) "Brassinosteroids Regulate Dissociation of BKI1, a Negative Regulator of BRI1 Signaling, from the Plasma Membrane" *Science* 313:1118). Dissociation of BKI1 from BRI1 and resulting activation of BRI1/BAK1 activates a signaling cascade, ultimately resulting in gene expression modulation in a variety of BR responsive genes. Overexpression of BKI1 is shown herein to inhibit BR activation of BRI1, with resulting inhibition of BR-mediated gene modulation; resulting phenotypic effects are also shown in whole plants. Conversely, inhibition of BKI1 expression (e.g., via RNAi transcript suppression) is shown herein to potentiate BR-mediated gene modulation, with resulting phenotypic effects in whole plants.

The features of the brassinosteroid pathway are broadly conserved in plants. Accordingly, details described for BRI1, BKI1, BAK1 and the like are applicable in other plants and many examples of plant species specific BRI1 and BKI1 polypeptides and nucleic acids are described herein. Thus, unless indicated to the contrary, reference to BKI1 herein is understood to be generally applicable to BKI1-type polypeptides; similarly, bki1 genes and nucleic acids are understood to refer generally to bki1-type nucleic acids and genes, unless otherwise indicated. Similar considerations apply to BRI1 and other components of the BR signaling pathway.

Figures 1A, 1B:
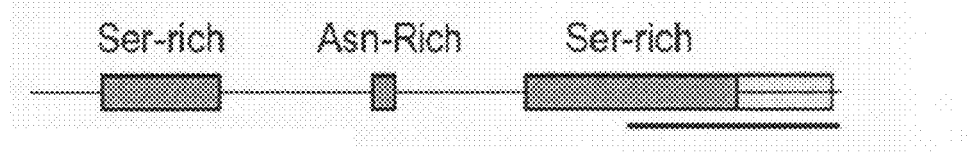
FIG. 1A provides a schematic drawing of a predicted domain structure for AtBKI1.
FIG. 1B provides an alignment of the deduced amino acid sequence of AtBKI1 (SEQ ID NO:1) with BKI1-like proteins from *Oryza sativa* (OsBKI1; AP005891.3; SEQ ID NO:2), *Medicago truncatula*, (MtBKI1; AC157645_3.1 identified in the database of the Institute for Genome Research; SEQ ID NO:3), *Gossypium raimondii* (GrBKI1, a putative full length gene assembled from ESTs: CO071302.1, CO081346.1, CO074191.1, and CO081345.1-; SEQ ID NO:4), and *Euphorbia esula* (EeBKI1, a putative full length gene assembled from ESTs: DV136456.1, DV156616.1, DV139943.1, DV131013.1, and DV131013.1; SEQ ID NO:5).
Figure 1C:
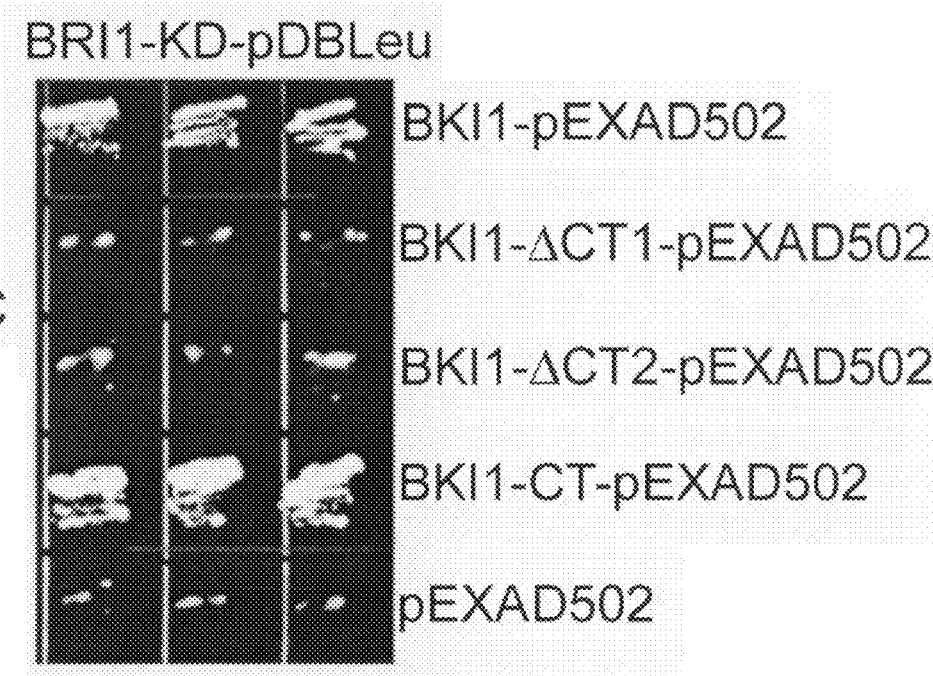
FIG. 1C is a photograph showing that the carboxyl domain of BKI1 is necessary and sufficient to interact with BRI1's kinase domain in yeast. Residues of BKI1 present in the constructs were 1-252 (BKI1-ΔCT1), 1-299 (BKI1-ΔCT2), and 253-337 (BKI1-CT).
Figure 1D:
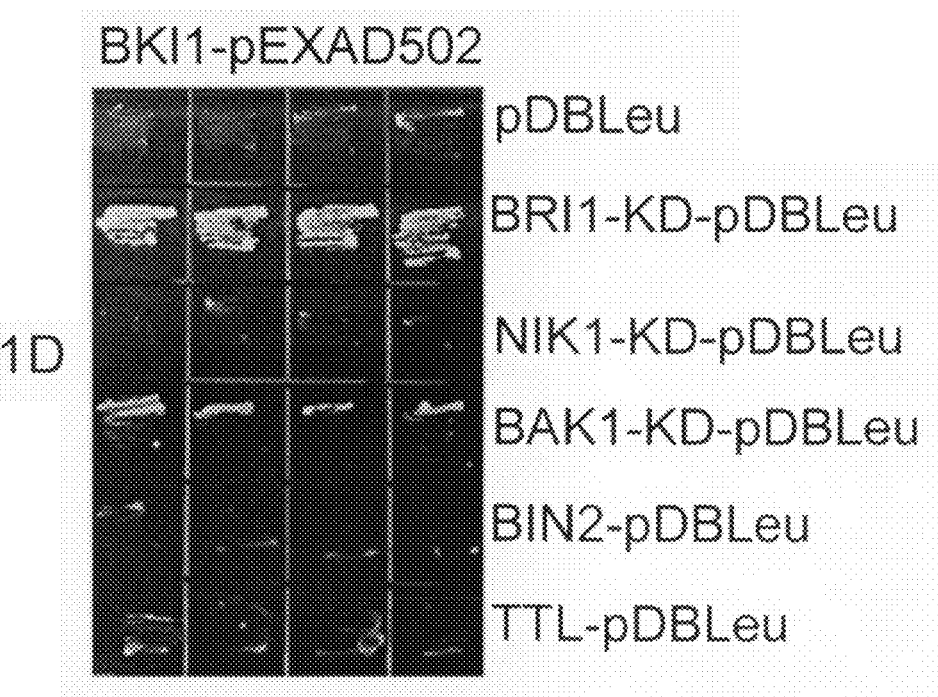
FIG. 1D is a photograph showing that BKI1 specifically interacts with BRI1. BKI1 fused with GAL4-AD (BKI1-pEXAD502) specifically interacts with the intracellular domain of BRI1 (BRI1-KD) fused with GAL4-DB in yeast.
Figure 1E:
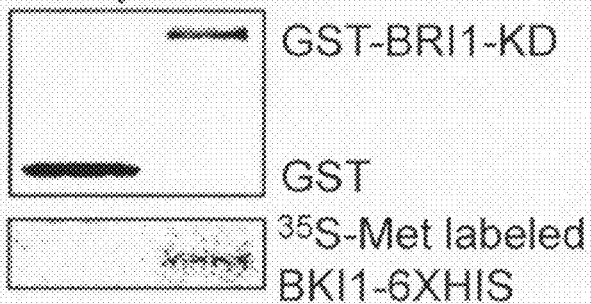
FIG. 1E is an autoradiogram showing that BKI1-6XHIS interacts with GST-BRI1-KD in vitro. In the pull-down product, the GST (Left) or GST-BRI1-KD (Right) was detected by anti-GST, and the S-35 Met labeled BKI1-6XHIS was detected by autoradiography.
Figure 1F:
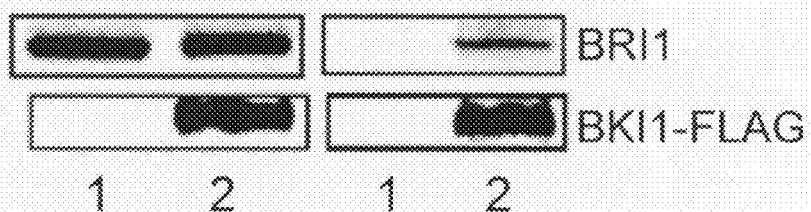
FIG. 1F is an autoradiogram showing that BKI1-FLAG interacts with endogenous BRI1 in planta. 1, Col-0; and 2, BKI1-FLAG over-expression line. BRI1 and BKI1-FLAG were detected by immunoblot with anti-BRI1 and anti-FLAG, respectively.
Figure 1G:
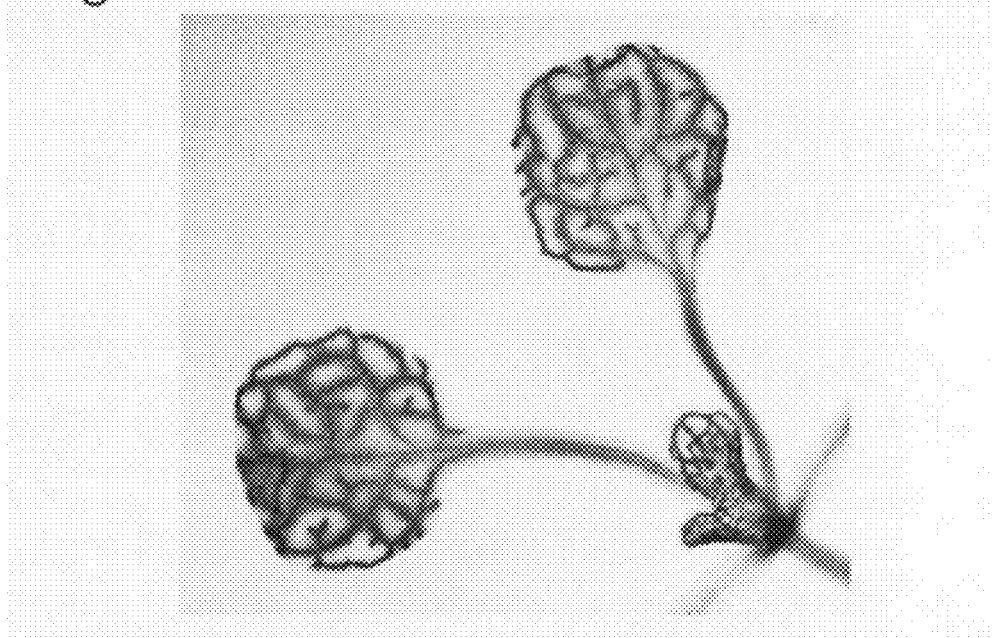
FIG. 1 G-J are photographs showing that pBKI1::GUS is ubiquitously expressed. GUS reporter gene expression was monitored in two-week-old seedlings leaves and shoot apices (G), hypocotyls (H), and roots (I), and flowers of adult plants (J).
FIG. 1K is a schematic illustration of a model for BR mediated signaling.
Figure 1H:
Figure 1I:
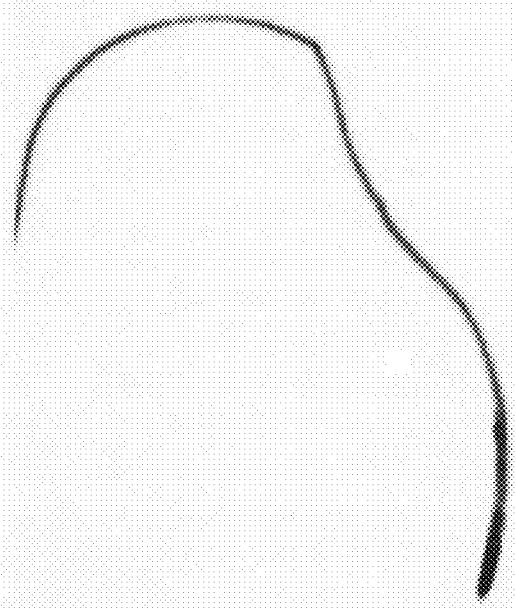
Figure 1J:
Figure 1K:
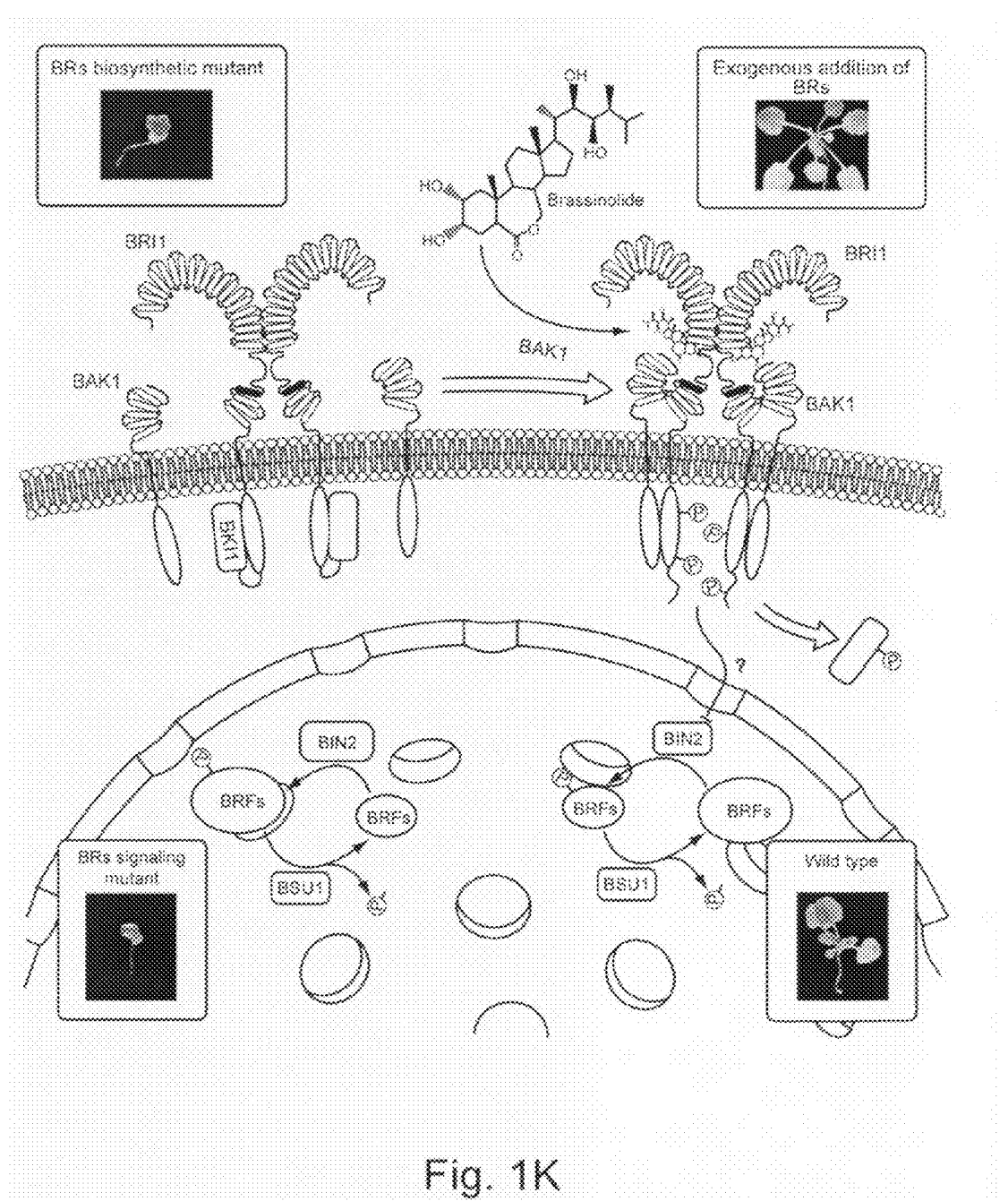

An example model for BR signaling that controls, e.g., *Arabidopsis* plant size, and that is consistent with available evidence, is found in FIG. 1K. As shown, *Arabidopsis* biosynthetic mutants that do not produce brassinolide (BL) are dwarf (upper left photo) but can be rescued to full stature by exogenous application of BL (upper right photo). BR signaling mutants (lower left photo) cannot be rescued by exogenous BL. In the absence of BRs, the kinase domains of the BRI1 homodimer are inhibited by both their own C-terminal domain and by an interaction with BKI1. This allows the GSK3 homolog, BIN2, to phosphorylate and inactivate the brassinosteroid response transcription factors (BRFs), including BES1 and BZR1. Direct binding of BL to BRI1 homodimers results in conformational changes of the kinase domain, leading to the phosphorylation of the C-terminal domain of BRI1 and phosphorylation of BKI1, which causes displacement of BKI1 from the plasma membrane and the release of autoinhibition of BRI1. These events lead to BRI1's association with BAK1 and consequent activation of the receptor. The active signaling receptor complex inhibits the activity of BIN2, allowing dephosphorylation of the BRFs by BSU1 and activation or repression of their target genes and optimal plant growth (lower right photo). The horseshoe-shaped representations of BRI1 and BAK1 LRR domains, as well as the putative LRR (red domains) interactions, are inferred from structural models of LRR-containing proteins. The atypical LRR21 is represented by a yellow domain. The BL docking into the binding site is speculative. Phosphorylation events are indicated by a circled P. See also, Belkhadir and Chory (2006) "Brassinosteroid Signaling: A Paradigm for Steroid Hormone Signaling from the Cell Surface" *Science* 314 (5804): 1410-1411.

Accordingly, this invention includes several features, relating to the description of BKI1-type polypeptides as control polypeptides in the brassinosteroid signaling pathway. For example, transgenic cells and plants that express either a recombinant BKI1-type polypeptide, or a regulator thereof (or both) are a feature of the invention. BKI1-type polypeptides that include exogenous features such as affinity tags, exogenous membrane binding domains, linkers, purification tags and labels are also a feature of the invention. Nucleic acids such as expression vectors encoding recombinant BKI1-type polypeptides, or modulators thereof, in conjunction with a promoter of interest (e.g., to achieve tissue-specific expression), are also a feature of the invention. Methods of regulating brassinosteroid response in a cell by modulating BKI1-type polypeptide levels and/or subcellular, cellular or tissue distribution are also a feature of the invention. Plant phenotypes are similarly regulated, e.g., by tissue-specific expression of BKI1-type polypeptides or modulators. Details regarding these and other features are found below.

DEFINITIONS

Before describing the present invention in more detail, it is to be understood that this invention is not limited to particular plants, cells, methods, or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the context dictates otherwise. Thus, for example, reference to "a cell" can include cells in culture, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

a "BKI1-type polypeptide" is a polypeptide that is the same as or homologous to BKI1 from *Arabadopsis thalinia*. Such polypeptides characteristically interact with BRI1 (or a homologue thereof relevant to a species in which the BKI1-type polypeptide is expressed) to repress BRI1 signaling. Thus, BKI1-type polypeptides are typically negative regulators of brassinosteroid signaling. For example, cells, tissues, or plants that overexpress a BKI-1 type polypeptide show reduced response to brassinolide as compared to control cells, tissues or plants that do not overexpress a BKI-1 polypeptide. BKI1-type polypeptides characteristically bind to the kinase domain of major brassinosteroid receptor BRI1-type proteins. A bki1 nucleic acid encodes a BKI1 polypeptide. A bki1 gene encodes a BKI1 polypeptide and is expressible in one or more cell.

A BRI1-type polypeptide is a polypeptide that is the same as or homologous to the *Arabidopsis thalinia* BRI1. The BRI1-type polypeptide is characteristically activated by brassinosteroids, resulting in activation of the brassinosteroid response pathway.

An "expression vector" is a vector comprising operably linked polynucleotide sequences that facilitate expression of a coding sequence in a particular host organism (e.g., a bacterial expression vector or a plant expression vector). Polynucleotide sequences that facilitate expression in prokaryotes can include, e.g., a promoter, an enhancer, an operator, and a ribosome binding site, often along with other sequences. Eukaryotic cells can use promoters, enhancers, termination and polyadenylation signals and other sequences that are generally different from those used by prokaryotes.

A "gene" refers is a heritable sequence of nucleic acid (typically DNA), i.e., a genomic sequence, with functional significance. Genes typically include an expressible nucleic acid sequence.

A "heterologous" component of a cell is a component that is derived from a source other than the cell, or that appears in the cell in a non-natural (artificial) context.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring BKI1 type polypeptide can be modified by any available mutagenesis method to produce a mutant BKI1 type polypeptide. Homology is generally inferred from sequence identity or similarity between two or more nucleic acids or proteins (or sequences thereof). The precise percentage of identity or similarity between sequences that is useful in establishing homology varies with the nucleic acid and protein at issue, but as little as 25% sequence similarity between proteins (and less between nucleic acids, due to the degeneracy of the genetic code) is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, whether part of the plant, or taken from a plant, or derived through culture from a cell taken from a plant. Thus, the term "plant" includes whole plants, plant cells, plant protoplast, plant or tissue culture from which plants can be regenerated, plant calli, plant clumps and plant cells that are intact in plants or parts of plants, such as seeds, pods, flowers, cotyledons, leaves, stems, buds, roots, root tips and the like.

A "recombinant cell" is a cell that is made by artificial recombination methods. The cell comprises one or more transgenes, e.g., a heterologous bki1 gene or modulator, introduced into the cell, or an ancestor thereof, by artificial recombinant methods.

A "transgenic plant" is a plant that comprises within its cells a heterologous polynucleotide. In many embodiments, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

A "modulator" is a compound that modulates an activity of a given nucleic acid, polypeptide, or polypeptide complex. The term "modulate" with respect to a BKI1 polypeptide refers to a change in BKI1 polypeptide production (e.g., where the modulator is a transcription factor, an antisense or an RNAi), or to a change in an activity or property of the polypeptide. For example, modulation can cause an increase or a decrease in a protein production (e.g., suppression of bki1 transcription or translation), activity (e.g., BRI1 signal repression), a binding characteristic (e.g., binding to BRI1), membrane stability (e.g., increased stability can result in decreased BRI1 mediated BR signaling, as shown herein), or any other biological, functional, or immunological property of such proteins. Changes in activity can arise from, for example, an increase or decrease in expression of one or more genes that encode the polypeptide, the stability of an mRNA that encodes the polypeptide, translation efficiency, or from a change in an activity of the protein itself.

bki1-Type Nucelic Acids and BKI1-Type Polypeptides

In *Arabadopsis thalinia*, BKI1 interacts with the kinase domain of BRI1, the major BR receptor in *Arabadopsis thalinia*. See also, FIG. 1K. This interaction is likely to be well conserved across many different plant species, for several reasons. First, BRI1-type genes and proteins have been identified in many diverse species, and have been shown to be involved in BR signaling in these different species (as well as having other roles in at least some plants, such as in peptide hormone signaling). This indicates that the BR signaling pathway that is mediated by BRI1, BKI1 and, e.g., BAK1 is likely to be conserved across a wide variety of species. Second, BKI1 is broadly conserved across the angiosperms, indicating that the role for BKI1 is likely conserved in concert with BRI1 in at least the angiosperms. Accordingly, proteins that share homology to (and, preferably, that display similar function with) BRI1 from *Arabadopsis thalinia* are referred to herein as "BRI1-like" polypeptides. Similarly, polypeptides that share homology to BKI1 from *Arabadopsis thalinia* (and preferably that are functionally similar to the *Arabadopsis thalinia* BKI1) are referred to as "BKI1-type" polypeptides.

Accordingly, multiple examples of BKI1-type and BRI1-type polypeptides can be identified in light of the present invention. For example, BRI1 is well studied. This protein was found in a genetic screen for BR insensitivity in *Arabidopsis*. bri1 mutants show dwarfed height, male sterility and de-etiolation in the dark, among other phenotypes. BRI1 was later identified as a "leucine rich repeat receptor like kinase (an "LRRxRLK" in the literature; see Morillo and Tax (2006) *Current Opinion in Plant Biology* 9:460-469) and confirmed as a transmembrane BR receptor by direct binding of BL to BRI1. BRI1 has structurally and functionally related homologues found in many different plant species. These homologues share a variety of structural features, including that they are leucine rich repeat receptor kinases with an extracellular domain with an N-terminal signal peptide followed by several imperfect leucine rich repeats (24 in the case of *Arabidopsis* thalinia), a single transmembrane domain and an intracellular serine-threonine kinase domain followed by a short C-terminal tail. Known homologues include the *Arabidopsis thalinia* BRI1, where the bri1 gene and its encoded protein were first described, as well as PsBRI1 (BRI1 homologue in pea, also known as Ika; see Nomura et al (2003) *The Plant Journal* 36(3) 291); HvBRI1 (BRI1 homologue in barley, see Chono et al. (2003) "A Semidwarf Phenotype of Barley uzu Results from a Nucleotide Substitution in the Gene Encoding a Putative Brassinosteroid Receptor" *Plant Physiology* 133:1209-1219), tBRI1 (tomato BRI1, see Montoya et al. (2002) "Cloning the Tomato Curl3 Gene Highlights the Putative Dual Role of the Leucine-Rich Repeat Receptor Kinase tBRI1/SR160 in Plant Steroid Hormone and Peptide Hormone Signaling" *The Plant Cell,* 14: 3163-3176; rice BRI1 (id) and others. For other examples, see, Morillo and Tax (2006) *Current Opinion in Plant Biology* 9:460-469.

BKI1 (BRI1 kinase inhibitor I) from *Arabidopsis thalinia* is described herein as a regulatory protein in the BR signaling system. This polypeptide functionally interacts with the kinase domain of BRI1, blocking signaling until BRI1 is activated by BR. The BKI1 protein and the gene that encodes it are well conserved across the angiosperms, with specific examples of BKI1-type genes and polypeptides being found in, e.g.: *Antirrhinum majus, Citrus sinensis, Curcuma longa, Glycine max, Helianthus petiolaris, Ipomoea nil, Lettuce sativa, Mesembryanthemum crystallinum, Nicotiana benthamiana, Nicotiana tabacum, Phaseolus vulgaris, Populus deltoids, Populus trichocarpa, Prunus persica, Solanum tuberosum, Thellungiella salsuginea,* and *Trifolium pretense.* Examples of BKI1-type polypeptide and corresponding bki1 nucleic acids being found e.g., in GeneBank, e.g., at accession numbers: AJ796385.1 (SEQ ID NO:20), AJ796560.1 (SEQ ID NO:21), CX674446.1 (SEQ ID NO:22), DY389957.1 (SEQ ID NO:23), BU579318.1 (SEQ ID NO:24), BE609508.1 (SEQ ID NO:25), BE609498.1 (SEQ ID NO:26), AW620804.1 (SEQ ID NO:27), DY946533.1 (SEQ ID NO:28), BJ557111.1 (SEQ ID NO:29), BJ575601.1 (SEQ ID NO:30), DY971277.1 (SEQ ID NO:31), BQ867285.1 (SEQ ID NO:32), BE130683.1 (SEQ ID NO:33), CK287132.1 (SEQ ID NO:34), EB435640.1 (SEQ ID NO:35), BQ481779.1 (SEQ ID NO:36), CX170112.1 (SEQ ID NO:37), CX175441.1 (SEQ ID NO:38), CX175253.1 (SEQ ID NO:39), DT481968.1 (SEQ ID NO:40), DT487361.1 (SEQ ID NO:41), DY636517.1 (SEQ ID NO:42), CX162638.1 (SEQ ID NO:43), DN773886.1 (SEQ ID NO:44) and BB923413.1 (SEQ ID NO:45).

The present invention is not limited to any particular BKI1 polypeptides or coding nucleic acids, as one of skill is fully able to identify BKI1 type polypeptides/nucleic acids in a variety of species, as well as to identify and make a variety of natural or artificial BKI1 polypeptides and genes. These include any of a wide variety of naturally occurring homologues, including those noted above, as well as artificial polypeptides derived from such natural forms through mutation and/or selection.

In general, BKI1-type polypeptide are those polypeptides that share detectable homology to Arabadopsis thalinia BKI1, or to a homologue found in Genebank at AJ796385.1 (SEQ ID NO:20), AJ796560.1 (SEQ ID NO:21), CX674446.1 (SEQ ID NO:22), DY389957.1 (SEQ ID NO:23), BU579318.1 (SEQ ID NO:24), BE609508.1 (SEQ ID NO:25), BE609498.1 (SEQ ID NO:26), AW620804.1 (SEQ ID NO:27), DY946533.1 (SEQ ID NO:28), BJ557111.1 (SEQ ID NO:29), BJ575601.1 (SEQ ID NO:30), DY971277.1 (SEQ ID NO:31), BQ867285.1 (SEQ ID NO:32), BE130683.1 (SEQ ID NO:33), CK287132.1 (SEQ ID NO:34), EB435640.1 (SEQ ID NO:35), BQ481779.1 (SEQ ID NO:36), CX170112.1 (SEQ ID NO:37), CX175441.1 (SEQ ID NO:38), CX175253.1 (SEQ ID NO:39), DT481968.1 (SEQ ID NO:40), DT487361.1 (SEQ ID NO:41), DY636517.1 (SEQ ID NO:42), CX162638.1 (SEQ ID NO:43), DN773886.1 (SEQ ID NO:44) or BB923413.1 (SEQ ID NO:45). BKI1-type polypeptides are typically BR signal regulator polypeptides that interact with a corresponding BRI1-type polypeptide to control downstream BRI1 mediated BR signaling.

BKI1-type nucleic acids and encoded proteins are homologous when they derive from a common ancestral nucleic acid, e.g., through natural evolution, or through artificial methods (mutation, gene synthesis, recombination, etc.). Homology between two or more proteins or nucleic acids is usually inferred by consideration of sequence similarity of the proteins. Typically, protein sequences with as little as 25% identity, when aligned for maximum correspondence, are identified as being homologous. In addition, many amino acid substitutions are "conservative" having little effect on protein function. Thus, sequence alignment algorithms typically account for whether differences in sequence are conservative or non-conservative.

Thus, homology can be inferred by performing a sequence alignment, e.g., using BLASTN (for coding nucleic acids) or BLASTP (for polypeptides), e.g., with the programs set to default parameters. For example, in one embodiment, the BKI1-type polypeptide is at least about 25%, at least about 50%, at least about 75%, at least about 80%, at least about 90% or at least about 95% identical to Arabadopsis thalinia BKI1, or to a BKI1 homologue found in Genebank at AJ796385.1 (SEQ ID NO:20), AJ796560.1 (SEQ ID NO:21), CX674446.1 (SEQ ID NO:22), DY389957.1 (SEQ ID NO:23), BU579318.1 (SEQ ID NO:24), BE609508.1 (SEQ ID NO:25), BE609498.1 (SEQ ID NO:26), AW620804.1 (SEQ ID NO:27), DY946533.1 (SEQ ID NO:28), BJ557111.1 (SEQ ID NO:29), BJ575601.1 (SEQ ID NO:30), DY971277.1 (SEQ ID NO:31), BQ867285.1 (SEQ ID NO:32), BE130683.1 (SEQ ID NO:33), CK287132.1 (SEQ ID NO:34), EB435640.1 (SEQ ID NO:35), BQ481779.1 (SEQ ID NO:36), CX170112.1 (SEQ ID NO:37), CX175441.1 (SEQ ID NO:38), CX175253.1 (SEQ ID NO:39), DT481968.1 (SEQ ID NO:40), DT487361.1 (SEQ ID NO:41), DY636517.1 (SEQ ID NO:42), CX162638.1 (SEQ ID NO:43), DN773886.1 (SEQ ID NO:44) or BB923413.1 (SEQ ID NO:45). Details regarding sequence alignment, identity, similarity and related concepts as applied to BKI1-type polypeptides and coding nucleic acids are found below. Details regarding mutation of available BKI1 proteins and coding nucleic acids to provide additional BKI1-type polypeptides and coding nucleic acids are also found below.

Because of the degeneracy of the genetic code, the percentage of identity or similarity at which homology can be detected in bki1-type nucleic acids can be substantially lower than for encoded BKI1-type polypeptides. Additional details regarding silent and conservative substitutions of BKI1 polypeptides and coding nucleic acids are found below.

Modulators of bki1-Type Nucelic Acids and BKI1-Type Polypeptides

The ability to modulate expression of bki1 genes and other nucleic acids, and expression of BKI1-type polypeptides is a valuable application of the present invention. Depending on the specific application at issue, it can be desirable to block BKI1-type polypeptide production or activity in certain tissues, while providing for high levels of BKI1-type polypeptide expression in other tissues. For example, to increase yield under dense planting conditions, it can be desirable to achieve high levels of expression of BKI1-type polypeptides in certain tissues, such as leaf or stalk tissues (e.g., to promote an erect leaf phenotype). At the same time, overexpression of BKI1 in other tissues can lead to phenotypes that are undesirable in some applications, e.g., small seed size. That is, increasing leaf erectness may result in superior vegetative growth under dense planting conditions, but small seed size can decrease crop yield, if, for example, the seed is the harvested plant product (e.g., as rice and other in grain crops, sunflower and other Asteraceae, beans, peas and other Leguminosae or Fabaceae, rapeseed and other Brassicaceae, flax seed and other Linaceae, and many others). In some cases, a dwarf or oversized phenotype is desired and constitutive or inducible expression of BKI1 or modulators thereof are desirable. Thus, the ability to control overall or cell/tissue-specific expression of BKI1 polypeptides, whether endogenous or recombinant to the cell/tissue at issue, is a preferred feature of the invention.

Promoters for Constiutive, Inducible or Tissue-Preferred/Specific Expression

Constitutive, inducible or tissue-preferred/specific expression can be achieved in any of a variety of ways, by controlling the level of BKI1 polypeptides that are expressed, e.g., in selected cell or tissue types. Expression of BKI1 polypeptides in plants, cells or plant tissues can be controllably modulated in any of a variety of ways. These include modulation of bki1 gene promoters to regulate endogenous bki1 gene activity; modulation of heterologous promoters coupled to nucleic acids that encode BKI1 to regulate recombinant BKI1 protein production; expression of antisense or RNAi nucleic acids that block translation of mRNA that encodes BKI1 polypeptides; increasing BKI1 activity by increasing membrane stability of the polypeptide, inhibition of BKI1 function by binding the polypeptide with an antibody, etc.

In general, a variety of plant promoters that can be used to direct expression of BKI1-type polypeptides or modulators thereof are known and available. One example database of plant promoters is PlantProm DB, an annotated collection of promoter sequences for RNA polymerase II from various plant species. See, e.g., Shahmuradov et al. (2003) "Plant-Prom: a database of plant promoter sequences" *Nucleic Acids Research* 31(1):114-117. The database was developed by Softberry in collaboration with Department of Computer Science at Royal Holloway, University of London (www(dot)softberry(dot)com/berry(dot) phtml?topic=plantprom&group=data&subgroup=plant prom). One relatively recent release of PlantProm DB contains 305 entries, including 71, 220 and 14 promoters from monocot, dicot and other plants, respectively. Another example database of suitable promoters is provided by the University of Georgia's plant genome mapping project. See, www(dot)plantgenome(dot)uga(dot)edu/links(dot)htm. Montgomery et al. (2006) "ORegAnno: an open access database and curation system for literature-derived promoters, transcription factor binding sites and regulatory variation" *Bioinformatics* 22(5): 637-640 describe an open access database for promoter identification from the literature. Mohanty et al. (2005) "Detection and Preliminary Analysis of Motifs in Promoters of Anaerobically Induced Genes of Different Plant Species" *Ann. Bot.* 96(4): 669-681 describe a variety of promoters from different plant species. Xie et al. (2005) "Expression of *Arabidopsis* MIRNA Genes" *Plant Physiology* 138 (4): 2145-2154 describe promoters for *Arabidopsis* MIRNA Genes. Florquin et al. (2005) "Large-scale structural analysis of the core promoter in mammalian and plant genomes" *Nucleic Acids Res.* 33(13): 4255-4264 describe core promoters in mammalian and plant genomes. Shahmuradov et al. (2005) "Plant promoter prediction with confidence estimation" *Nucleic Acids Res.* 33(3): 1069-1076 provide plant promoter prediction methods for evaluating plant genomic data. Steffens et al (2004) "AthaMap: an online resource for in silico transcription factor binding sites in the *Arabidopsis thaliana* genome" *Nucleic Acids Res.* 32(90001): D368-372 describe predicted promoters in *Arabidopsis thaliana*. These and many other promoters and other genomic features (enhancers, etc.) are widely available to skilled practitioners.

Accordingly, constitutive and inducible promoters that function in plants are well known, e.g., in the references discussed above and can be used where expression of BKI1 polypeptides or modulators in multiple tissues and developmental stages is desired. This can be useful, e.g., for making dwarf varieties (e.g., by overexpressing BKI1) or oversized varieties (e.g., by expressing a BKI1 modulator such as an RNAi). Common examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1 8 promoter, Pol III promoters, and other transcription initiation regions from various plant genes known to those of skill. Examples of inducible promoters include the Adh1 promoter (inducible by hypoxia or cold stress), Hsp70 promoters (inducible by heat stress), and the PPDK promoter which is inducible by light. The references discussed above include extensive additional examples of constitutive and inducible plant promoters that can be used in the present invention.

Similarly, cell and tissue-specific/preferred plant promoters are also known and available, e.g., as described in the references above. These promoters are applicable in many applications of the present invention. For example, tissue-specific/preferred promoters derived from tissues where expression of BKI1 is desired (or where expression of a translation blocking modulator such as an RNAi that blocks BKI1 transcription is desired) can be used and are readily available. For example, seed preferred/specific promoters include promoters derived from phaseolin or napin genes, beta-amylase gene promoters, hordein gene promoters, β-conglycinin gene promoters, maize Ovule Development Protein 2 (ODP2) gene promoters, and many others. Similarly, tomato pz7 and pz130 gene promoters (or appropriate homologous gene promoters) can be used for ovary-preferred/specific expression. The banana TRX promoter and melon actin promoters can be used to drive expression in fruit. The tobacco RD2 gene promoter, or appropriate homologous gene promoters can be used for root gene expression. The Patatin protein gene (the major storage protein in potato) can be used (Kim (1994) *Plant Mol. Biol.* 26:603 615; Martin (1997) *Plant J.* 11:53 62). Similarly, the ORF13 promoter from *Agrobacterium rhizogenes* exhibits high activity in roots (Hansen (1997) *Mol. Gen. Genet.* 254:337 343). Other useful vegetative tissue-preferred/specific promoters include: the tarin promoter of the gene encoding a globulin from a major taro (*Colocasia esculenta* L. Schott) corm protein family, tarin (Bezerra (1995) Plant Mol. Biol. 28:137 144); the curculin promoter active during taro corm development (de Castro (1992) Plant Cell 4:1549 1559) and the promoters for the tobacco root-specific gene TobRB7, whose expression is localized to root meristem and immature central cylinder regions (Yamamoto (1991) Plant Cell 3:371 382). Leaf-specific promoters, such as the ribulose biphosphate carboxylase (RBCS) promoters can be used (Meier (1997) FEBS Lett. 415:91 95). A ribulose bisphosphate carboxylase promoter that is expressed preferentially in mesophyll cells in leaf blades and leaf sheaths at high levels is described by Matsuoka (1994) Plant J. 6:311 319. Another leaf-preferred/specific promoter is the chlorophyll a/b binding protein gene promoter (Shiina (1997) *Plant Physiol.* 115:477 483; Casal (1998) Plant Physiol. 116:1533 1538). The *Arabidopsis thaliana* myb-related gene promoter (Atmyb5) is leaf-specific (Li (1996) *FEBS Lett.* 379:117 121). The Atmyb5 promoter is expressed in developing leaf trichomes, stipules, and epidermal cells on the margins of young rosette and cauline leaves, and in immature seeds. Leaf promoters identified in maize can also be used (Busk (1997) *Plant J.* 11:1285 1295). Vegetative tissue-specific promoters including meristematic (root tip and shoot apex) promoters are known and available. For example, the "shootmeristemless" and "scarecrow" promoters, active in developing shoot or root apical meristems, are known (Di Laurenzio (1996) *Cell* 86:423 433; Long (1996) *Nature* 379:66 69); can be used. Another useful promoter for floral and meristematic expression controls the expression of 3-hydroxy-3-methylglutaryl coenzyme A reductase HMG2 gene (Enjuto (1995) *Plant Cell*. 7:517 527). Similarly, the knl-related genes from maize and other species show meristem-specific expression (Granger (1996) *Plant Mol. Biol.* 31:373 378; Kerstetter (1994) *Plant Cell* 6:1877 1887; Hake (1995) *Philos. Trans. R. Soc. Lond. B. Biol. Sci.* 350:45 51). The *Arabidopsis thaliana* KNAT1 or KNAT2 promoters direct expression primarily in the shoot apical meristem; expression of KNAT1 in the shoot meristem decreases during floral transition and is restricted to the inflorescence stem (Lincoln (1994) *Plant Cell* 6:1859 1876). A variety of tissue specific and tissue preferred promoters are further described in the references above.

BKI1/bki1 Modulators

Modulators of native or recombinant BKI1 proteins and coding nucleic acids can be engineered into a cell or plant of interest to control transcription or translation of coding nucleic acids. For example, recombinantly encoded modulators can be coupled to promoters as noted above for expression in whole plants, plant tissues or plant cells. These modulators can increase BKI1 expression, e.g., where the modulator is a transcription factor, or can decrease transcription or translation of BKI1, e.g., where the modulator is an antisense or RNAi molecule. This type of modulation can be used to fine-tune expression patterns for BKI1 in various tissues to achieve desired phenotypes such as leaf erectness combined with normal or large seeds, or can be used, e.g., to create large plants in whole plant expression applications (e.g., by effectively reducing BKI1 expression in the plant).

Many modulators of protein expression are known generally and can be used in the subject invention to control BKI1 expression or activity, including antibodies that bind to BKI1, transcription factors that trans-activate expression of bki1 genes, anti-sense expression that blocks BKI1/bki1 transcription or translation, and various Si-RNA types of BKI1 translation inhibitors.

For example, use of antisense nucleic acids is well known in the art. An antisense nucleic acid has a region of complementarity to a target nucleic acid, e.g., a target BKI1 protein transcript (e.g., mRNA) or coding DNA. Typically, a nucleic acid comprising a nucleotide sequence in a complementary, antisense orientation with respect to a coding (sense) sequence of an endogenous gene is introduced into a cell. The antisense nucleic acid can be RNA, DNA, a PNA or any other appropriate molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, e.g., for any gene whose coding sequence is known or can be determined by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, e.g., in U.S. Pat. No. 6,242,258 to Haselton and Alexander (Jun. 5, 2001) entitled "Methods for the selective regulation of DNA and RNA transcription and translation by photoactivation"; U.S. Pat. No. 6,500,615; U.S. Pat. No. 6,498,035; U.S. Pat. No. 6,395,544; U.S. Pat. No. 5,563,050; E. Schuch et al (1991) *Symp Soc. Exp Biol* 45:117-127; de Lange et al., (1995) *Curr Top Microbiol Immunol* 197:57-75; Hamilton et al. (1995) *Curr Top Microbiol Immunol* 197:77-89; Finnegan et al., (1996) *Proc Natl Acad Sci USA* 93:8449-8454; Uhlmann and A. Pepan (1990), *Chem. Rev.* 90:543; P. D. Cook (1991), *Anti-Cancer Drug Design* 6:585; J. Goodchild, Bioconjugate Chem. 1 (1990) 165; and, S. L. Beaucage and R. P. Iyer (1993), *Tetrahedron* 49:6123; and F. Eckstein, Ed. (1991), *Oligonucleotides and Analogues—A Practical Approach*, IRL Press.

Gene expression can also be inhibited by RNA silencing or interference. "RNA silencing" refers to any mechanism through which the presence of a single-stranded, or, more typically, a double-stranded RNA in a cell results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g., histone acetylation and heterochromatin formation leading to inhibition of transcription of the target mRNA).

The term "RNA interference" ("RNAi," sometimes called RNA-mediated interference, post-transcriptional gene silencing, or quelling) refers to a phenomenon in which the presence of RNA, typically double-stranded RNA, in a cell results in inhibition of expression of a gene comprising a sequence identical, or nearly identical, to that of the double-stranded RNA. The double-stranded RNA responsible for inducing RNAi is called an "interfering RNA." Expression of the gene is inhibited by the mechanism of RNAi as described below, in which the presence of the interfering RNA results in degradation of mRNA transcribed from the gene and thus in decreased levels of the mRNA and any encoded protein.

The mechanism of RNAi has been and is being extensively investigated in a number of eukaryotic organisms and cell types. See, for example, the following reviews: McManus and Sharp (2002) "Gene silencing in mammals by small interfering RNAs" Nature Reviews Genetics 3:737-747; Hutvagner and Zamore (2002) "RNAi: Nature abhors a double strand" Curr Opin Genet & Dev 200:225-232; Hannon (2002) "RNA interference" Nature 418:244-251; Agami (2002) "RNAi and related mechanisms and their potential use for therapy" Curr Opin Chem Biol 6:829-834; Tuschl and Borkhardt (2002) "Small interfering RNAs: A revolutionary tool for the analysis of gene function and gene therapy" Molecular Interventions 2:158-167; Nishikura (2001) "A short primer on RNAi: RNA-directed RNA polymerase acts as a key catalyst" Cell 107:415-418; and Zamore (2001) "RNA interference: Listening to the sound of silence" Nature Structural Biology 8:746-750. RNAi is also described in the patent literature; see, e.g., CA 2359180 by Kreutzer and Limmer entitled "Method and medicament for inhibiting the expression of a given gene"; WO 01/68836 by Beach et al. entitled "Methods and compositions for RNA interference"; WO 01/70949 by Graham et al. entitled "Genetic silencing"; and WO 01/75164 by Tuschl et al. entitled "RNA sequence-specific mediators of RNA interference."

In brief, double-stranded RNA introduced into a cell (e.g., into the cytoplasm) is processed, for example by an RNAse III-like enzyme called Dicer, into shorter double-stranded fragments called small interfering RNAs (siRNAs, also called short interfering RNAs). The length and nature of the siRNAs produced is dependent on the species of the cell, although typically siRNAs are 21-25 nucleotides long (e.g., an siRNA may have a 19 base pair duplex portion with two nucleotide 3' overhangs at each end). Similar siRNAs can be produced in vitro (e.g., by chemical synthesis or in vitro transcription) and introduced into the cell to induce RNAi. The siRNA becomes associated with an RNA-induced silencing complex (RISC). Separation of the sense and antisense strands of the siRNA, and interaction of the siRNA antisense strand with its target mRNA through complementary base-pairing interactions, optionally occurs. Finally, the mRNA is cleaved and degraded.

Expression of a target gene in a cell can thus be specifically inhibited by introducing an appropriately chosen double-stranded RNA into the cell. Guidelines for design of suitable interfering RNAs are known to those of skill in the art. For example, interfering RNAs are typically designed against exon sequences, rather than introns or untranslated regions. Characteristics of high efficiency interfering RNAs may vary by cell type. For example, although siRNAs may require 3' overhangs and 5' phosphates for most efficient induction of RNAi in *Drosophila* cells, in mammalian cells blunt ended siRNAs and/or RNAs lacking 5' phosphates can induce RNAi as effectively as siRNAs with 3' overhangs and/or 5' phosphates (see, e.g., Czauderna et al. (2003) "Structural variations and stabilizing modifications of synthetic siRNAs in mammalian cells" Nucl Acids Res 31:2705-2716). As another example, since double-stranded RNAs greater than 30-80 base pairs long activate the antiviral interferon response in mammalian cells and result in non-specific silencing, interfering RNAs for use in mammalian cells are typically less than 30 base pairs (for example, Caplen et al. (2001) "Specific inhibition of gene expression by small double-stranded RNAs in invertebrate and vertebrate systems" Proc. Natl. Acad. Sci. USA 98:9742-9747, Elbashir et al. (2001) "Duplexes of 21-nucleotide RNAs mediate RNA interference in cultured mammalian cells" Nature 411:494-498 and Elbashir et al. (2002) "Analysis of gene function in somatic mammalian cells using small interfering RNAs" Methods 26:199-213 describe the use of 21 nucleotide siR- NAs to specifically inhibit gene expression in mammalian cell lines, and Kim et al. (2005) "Synthetic dsRNA Dicer substrates enhance RNAi potency and efficacy" Nature Biotechnology 23:222-226 describes use of 25-30 nucleotide duplexes). The sense and antisense strands of a siRNA are typically, but not necessarily, completely complementary to each other over the double-stranded region of the siRNA (excluding any overhangs). The antisense strand is typically completely complementary to the target mRNA over the same region, although some nucleotide substitutions can be tolerated (e.g., a one or two nucleotide mismatch between the antisense strand and the mRNA can still result in RNAi, although at reduced efficiency). The ends of the double-stranded region are typically more tolerant to substitution than the middle; for example, as little as 15 bp (base pairs) of complementarity between the antisense strand and the target mRNA in the context of a 21 mer with a 19 bp double-stranded region has been shown to result in a functional siRNA (see, e.g., Czauderna et al. (2003) "Structural variations and stabilizing modifications of synthetic siRNAs in mammalian cells" Nucl Acids Res 31:2705-2716). Any overhangs can but need not be complementary to the target mRNA; for example, TT (two 2'-deoxythymidines) overhangs are frequently used to reduce synthesis costs.

Although double-stranded RNAs (e.g., double-stranded siRNAs) were initially thought to be required to initiate RNAi, several recent reports indicate that the antisense strand of such siRNAs is sufficient to initiate RNAi. Single-stranded antisense siRNAs can initiate RNAi through the same pathway as double-stranded siRNAs (as evidenced, for example, by the appearance of specific mRNA endonucleolytic cleavage fragments). As for double-stranded interfering RNAs, characteristics of high-efficiency single-stranded siRNAs may vary by cell type (e.g., a 5' phosphate may be required on the antisense strand for efficient induction of RNAi in some cell types, while a free 5' hydroxyl is sufficient in other cell types capable of phosphorylating the hydroxyl). See, e.g., Martinez et al. (2002) "Single-stranded antisense siRNAs guide target RNA cleavage in RNAi" Cell 110:563-574; Amarzguioui et al. (2003) "Tolerance for mutations and chemical modifications in a siRNA" Nucl. Acids Res. 31:589-595; Holen et al. (2003) "Similar behavior of single-strand and double-strand siRNAs suggests that they act through a common RNAi pathway" Nucl. Acids Res. 31:2401-2407; and Schwarz et al. (2002) Mol. Cell. 10:537-548.

Due to currently unexplained differences in efficiency between siRNAs corresponding to different regions of a given target mRNA, several siRNAs are typically designed and tested against the target mRNA to determine which siRNA is most effective. Interfering RNAs can also be produced as small hairpin RNAs (shRNAs, also called short hairpin RNAs), which are processed in the cell into siRNA-like molecules that initiate RNAi (see, e.g., Siolas et al. (2005) "Synthetic shRNAs as potent RNAi triggers" Nature Biotechnology 23:227-231).

The presence of RNA, particularly double-stranded RNA, in a cell can result in inhibition of expression of a gene comprising a sequence identical or nearly identical to that of the RNA through mechanisms other than RNAi. For example, double-stranded RNAs that are partially complementary to a target mRNA can repress translation of the mRNA without affecting its stability. As another example, double-stranded RNAs can induce histone methylation and heterochromatin formation, leading to transcriptional silencing of a gene comprising a sequence identical or nearly identical to that of the RNA (see, e.g., Schramke and Allshire (2003) "Hairpin RNAs and retrotransposon LTRs effect RNAi and chromatin-based gene silencing" Science 301:1069-1074; Kawasaki and Taira (2004) "Induction of DNA methylation and gene silencing by short interfering RNAs in human cells" Nature 431: 211-217; and Morris et al. (2004) "Small interfering RNA-induced transcriptional gene silencing in human cells" Science 305:1289-1292).

Short RNAs called microRNAs (miRNAs) have been identified in a variety of species. Typically, these endogenous RNAs are each transcribed as a long RNA and then processed to a pre-miRNA of approximately 60-75 nucleotides that forms an imperfect hairpin (stem-loop) structure. The pre-miRNA is typically then cleaved, e.g., by Dicer, to form the mature miRNA. Mature miRNAs are typically approximately 21-25 nucleotides in length, but can vary, e.g., from about 14 to about 25 or more nucleotides. Some, though not all, miRNAs have been shown to inhibit translation of mRNAs bearing partially complementary sequences. Such miRNAs contain one or more internal mismatches to the corresponding mRNA that are predicted to result in a bulge in the center of the duplex formed by the binding of the miRNA antisense strand to the mRNA. The miRNA typically forms approximately 14-17 Watson-Crick base pairs with the mRNA; additional wobble base pairs can also be formed. In addition, short synthetic double-stranded RNAs (e.g., similar to siRNAs) containing central mismatches to the corresponding mRNA have been shown to repress translation (but not initiate degradation) of the mRNA. See, for example, Zeng et al. (2003) "MicroRNAs and small interfering RNAs can inhibit mRNA expression by similar mechanisms" Proc. Natl. Acad. Sci. USA 100:9779-9784; Doench et al. (2003) "siRNAs can function as miRNAs" Genes & Dev. 17:438-442; Bartel and Bartel (2003) "MicroRNAs: At the root of plant development?" Plant Physiology 132:709-717; Schwarz and Zamore (2002) "Why do miRNAs live in the miRNP?" Genes & Dev. 16:1025-1031; Tang et al. (2003) "A biochemical framework for RNA silencing in plants" Genes & Dev. 17:49-63; Meister et al. (2004) "Sequence-specific inhibition of microRNA- and siRNA-induced RNA silencing" RNA 10:544-550; Nelson et al. (2003) "The microRNA world: Small is mighty" Trends Biochem. Sci. 28:534-540; Scacheri et al. (2004) "Short interfering RNAs can induce unexpected and divergent changes in the levels of untargeted proteins in mammalian cells" Proc. Natl. Acad. Sci. USA 101:1892-1897; Sempere et al. (2004) "Expression profiling of mammalian microRNAs uncovers a subset of brain-expressed microRNAs with possible roles in murine and human neuronal differentiation" Genome Biology 5:R13; Dykxhoorn et al. (2003) "Killing the messenger: Short RNAs that silence gene expression" Nature Reviews Molec. and Cell Biol. 4:457-467; McManus (2003) "MicroRNAs and cancer" Semin Cancer Biol. 13:253-288; and Stark et al. (2003) "Identification of *Drosophila* microRNA targets" PLoS Biol. 1:E60.

The cellular machinery involved in translational repression of mRNAs by partially complementary RNAs (e.g., certain miRNAs) appears to partially overlap that involved in RNAi, although, as noted, translation of the mRNAs, not their stability, is affected and the mRNAs are typically not degraded.

The location and/or size of the bulge(s) formed when the antisense strand of the RNA binds the mRNA can affect the ability of the RNA to repress translation of the mRNA. Similarly, location and/or size of any bulges within the RNA itself can also affect efficiency of translational repression. See, e.g., the references above. Typically, translational repression is most effective when the antisense strand of the RNA is complementary to the 3' untranslated region (3' UTR) of the mRNA. Multiple repeats, e.g., tandem repeats, of the sequence complementary to the antisense strand of the RNA can also provide more effective translational repression; for example, some mRNAs that are translationally repressed by endogenous miRNAs contain 7-8 repeats of the miRNA binding sequence at their 3' UTRs. It is worth noting that translational repression appears to be more dependent on concentration of the RNA than RNA interference does; translational repression is thought to involve binding of a single mRNA by each repressing RNA, while RNAi is thought to involve cleavage of multiple copies of the mRNA by a single siRNA-RISC complex.

Guidance for design of a suitable RNA to repress translation of a given target mRNA can be found in the literature (e.g., the references above and Doench and Sharp (2004) "Specificity of microRNA target selection in translational repression" Genes & Dev. 18:504-511; Rehmsmeier et al. (2004) "Fast and effective prediction of microRNA/target duplexes" RNA 10:1507-1517; Robins et al. (2005) "Incorporating structure to predict microRNA targets" Proc Natl Acad Sci 102:4006-4009; and Mattick and Makunin (2005) "Small regulatory RNAs in mammals" Hum. Mol. Genet. 14:R121-R132, among many others) and herein. However, due to differences in efficiency of translational repression between RNAs of different structure (e.g., bulge size, sequence, and/or location) and RNAs corresponding to different regions of the target mRNA, several RNAs are optionally designed and tested against the target mRNA to determine which is most effective at repressing translation of the target mRNA.

Generation of Expression Vectors, Transgenic Cells and Transgenic Plants

The present invention includes host cells and organisms (especially transgenic plants) that comprise recombinant nucleic acids that encode BKI1-type polypeptides and/or modulators thereof. The invention provides for the production of recombinant nucleic acids (e.g., RNAi or antisense molecules) and polypeptides (e.g., BKI1-type polypeptides) that regulate brassinosteroid signaling pathways in such (plant) organisms.

General texts that describe molecular biological techniques for the cloning and manipulation of bki1 nucleic acids and production of encoded BKI1 polypeptides include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through the current date) ("Ausubel")). These texts describe mutagenesis, the use of expression vectors, promoters and many other relevant topics related to, e.g., the generation of clones that comprise nucleic acids of interest, e.g., BKI1 polypeptides, modulators, and coding nucleic acids.

Host cells are genetically engineered (e.g., transduced, transfected, transformed, etc.) with the vectors of this invention (e.g., vectors, such as expression vectors which comprise an ORF derived from or related to a BKI1-type polypeptide or coding nucleic acid) which can be, for example, a cloning vector, a shuttle vector or an expression vector. Such vectors are, for example, in the form of a plasmid, a phagemid, an agrobacterium, a virus, a naked polynucleotide (linear or circular), or a conjugated polynucleotide. Vectors can be introduced into bacteria, especially for the purpose of propagation, expansion and BKI1-type polypeptide or modulator production (e.g., for external application of the polypeptides or modulators as brassinosteroid signal regulators, for isolating BKI1-type polypeptides for use in screening applications to identify specific BKI1 modulators, for making protein crystals, etc.). The vectors are also optionally introduced into plant tissues, cultured plant cells or plant protoplasts by any of a variety of standard methods known in the art, including but not limited to electroporation (From et al. (1985) *Proc. Natl. Acad. Sci. USA* 82; 5824), infection by viral vectors such as cauliflower mosaic virus (CaMV) (Hohn et al. (1982) *Molecular Biology of Plant Tumors* (Academic Press, New York, pp. 549-560; Howell U.S. Pat. No. 4,407,956), high velocity ballistic penetration by small particles with the nucleic acid either within the matrix of small beads or particles, or on the surface (Klein et al. (1987) *Nature* 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233; 496; Fraley et al. (1983) *Proc. Natl. Acad. Sci. USA* 80; 4803). Additional details regarding nucleic acid introduction methods are found in Sambrook, Berger and Ausubel. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, plant regeneration from cultured protoplasts is described in Evans et al. (1983) "Protoplast Isolation and Culture," *Handbook of Plant Cell Cultures* 1, 124-176 (MacMillan Publishing Co., New York; Davey (1983) "Recent Developments in the Culture and Regeneration of Plant Protoplasts," *Protoplasts*, pp. 12-29, (Birkhauser, Basel); Dale (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton, Fla.). Additional details regarding plant cell culture and regeneration are found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture; Fundamental Methods* Springer Lab Manual, Springer-Verlag (Berlin Heidelberg New York); Plant Molecular Biology (1993) R. R. D. Croy, Ed. Bios Scientific Publishers, Oxford, U.K. ISBN 0 12 198370 6 and *Plant Cell Culture Protocols* second edition (Methods in Molecular Biology) (2005) Loyola-Vargas (Editor), Vazquez-Flota (Editor) Humana Press, ISBN-10: 1588295478. Cell culture media in general are also set forth in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., *the Plant Culture Catalogue* and supplement (e.g., 1997 or later) also from Sigma-Aldrich, Inc (St Louis, Mo.) ("Sigma-PCCS").

The present invention also relates to the production of transgenic organisms, which may be, e.g., bacteria, yeast, fungi, animals or plants, transduced with the nucleic acids of the invention (e.g., nucleic acids encoding BKI1-type polypeptides or modulators, as noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith (1979) *Gene* 8:81; Roberts et al. (1987) *Nature* 328:731; Schneider et al. (1995) *Protein Expr. Purif.* 6435:10; Ausubel, Sambrook, Berger (all infra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Introducing Nucleic Acids into Plants.

Embodiments of the present invention include the production of transgenic plants comprising cloned nucleic acids, e.g., BKI1-type polypeptide coding nucleic acids and/or modulators. Techniques for transforming plant cells with nucleic acids are widely available and can readily be adapted to the invention. Useful general references for plant cell cloning, culture and regeneration include Loyola-Vargas (Editor), Vazquez-Flota (Editor) (2005) *Plant Cell Culture Protocols second edition* (Methods in Molecular Biology) Humana Press, ISBN-10: 1588295478; Lea and Leegood (1999) *Plant Biochemistry and Molecular Biology, 2nd Edition*, ISBN-10: 0471976830; Jones (ed) (1995) *Plant Gene Transfer and Expression Protocols—Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). Additional details regarding plant cell culture are found in Croy, (ed.) (1993) *Plant Molecular Biology*, Bios Scientific Publishers, Oxford, U.K. Additional useful details regarding plant biochemistry can be found in Hans-Walter Heldt (2004) *Plant Biochemistry, Third Edition* ISBN-10: 0120883910.

The nucleic acid constructs of the invention, e.g., plasmids, cosmids, artificial chromosomes, which can include DNA or RNA, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acid constructs of the present invention can be introduced into plants according to any of a variety of techniques known in the art. In addition to transformation of cells followed by regeneration, techniques for transforming a wide variety of higher plant species are also well known and described in widely available technical, scientific, and patent literature. See, for example, Loyola-Vargas (Editor), Vazquez-Flota (Editor) (2005) *Plant Cell Culture Protocols second edition* (Methods in Molecular Biology) Humana Press, ISBN-10: 1588295478; Lea and Leegood (1999) *Plant Biochemistry and Molecular Biology 2nd Edition*, ISBN-10: 0471976830; and Weising et al. (1988) *Ann. Rev. Genet.* 22:421-477.

The constructs of the invention, e.g., BKI1-type polypeptide coding nucleic acids, nucleic acid that encode modulators of BKI1, or the like, can be provided as components of, e.g., plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of a plant or plant cell using available techniques, such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones (ed) (1995) *Plant Gene Transfer and Expression Protocols—Methods in Molecular Biology, Volume* 49 Humana Press, Towata, N.J., as well as in the other references noted herein and available in the literature.

For example, the introduction of DNA constructs using polyethylene glycol precipitation is described in Paszkowski, et al., *EMBO J.* 3:2717 (1984). Electroporation techniques are described in Fromm, et al., *Proc. Natl. Acad. Sci. USA* 82:5824 (1985). Ballistic transformation techniques are described in Klein, et al., *Nature* 327:70-73 (1987). Additional details are found in Jones (1995) and Gamborg and Phillips (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example, Horsch, et al. (1984) *Science* 233:496; and Fraley et al. (1984) *Proc. Nat'l. Acad. Sci. USA* 80:4803; reviewed in Hansen and Chilton (1998) *Current Topics in Microbiology* 240:22 and Das (1998) *Subcellular Biochemistry* 29: *Plant Microbe Interactions*, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: *Genetic Engineering*, vol. 6, PWJ Rigby, Ed., London, Academic Press; and Lichtenstein; C. P., and Draper (1985) In: DNA Cloning, Vol. II, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci.*, (*USA*) 87:1228.

DNA can also be introduced into plants by direct DNA transfer into pollen as described by Zhou et al. (1983) *Methods in Enzymology*, 101:433; D. Hess (1987) *Intern Rev. Cytol.* 107:367; Luo et al. (1988) *Plant Mol. Biol. Reporter* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al. (1987) *Theor. Appl. Genet.* 75:30; and Benbrook et al. (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Generation/Regeneration of Transgenic Plants

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Loyola-Vargas (Editor), Vázquez-Flota (Editor) (2005) *Plant Cell Culture Protocols second edition* (Methods in Molecular Biology) Humana Press, ISBN-10: 1588295478; Lea and Leegood (1999) *Plant Biochemistry and Molecular Biology, 2nd Edition*, ISBN-10: 0471976830; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Evans et al. (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton.

Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. (1987) *Ann. Rev. of Plant Phys.* 38:467-486. Additional details are found in Payne (1992) and Jones (1995), both supra, and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants expressing BKI1-type polypeptides or modulators thereof.

In addition, the regeneration of plants containing the polynucleotide of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci.* (*U.S.A.*) 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

It is not intended that plant transformation and expression of polypeptides that provide for various brassinosteroid pathway regulators, as provided by the present invention, be limited to any particular plant species. Indeed, it is contemplated that BKI1-type polypeptides and modulators can provide for brassinosteroid pathway engineering when transformed into and expressed in any agronomically and horticulturally important species. Such species include dicots, e.g., of the families: Leguminosae (including pea, beans, lentil, peanut, yam bean, cowpeas, velvet beans, soybean, clover, alfalfa, lupine, vetch, lotus, sweet clover, wisteria, and sweetpea); and, Compositae (the largest family of vascular plants, including at least 1,000 genera, including important commercial crops such as sunflower), as well as monocots, such as from the family Graminae. Plants of the Rosaciae are also preferred targets.

Plants that use BKI1-type polypeptides to modulate brassinosteroid signaling include the angiosperms, including the Orchidaceae, the Asteraceae or Compositae, the Fabaceae or Leguminosae, the Poaceae or Gramineae, the Rubiaceae, the Euphorbiaceae, the Malvaceae, the Cyperaceae or Araceae. Accordingly, preferred targets for BKI1-type polypeptide or modulator expression include angiosperms, including the plant families listed. Preferred targets for modification with the nucleic acids of the invention, as well as those specified above, include plants from the genera: *Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum,*

*Stenotaphrum, Theobroma, Trifolium, Trigonella, Triticum, Vicia, Vigna, Vitis, Zea*, the Olyreae, and the Pharoideae, and many others. Preferred species include *Antirrhinum majus, Citrus sinensis, Curcuma longa, Glycine max, Helianthus petiolaris, Ipomoea nil*, Lettuce *sativa, Mesembryanthemum crystallinum, Nicotiana benthamiana, Nicotiana tabacum, Phaseolus vulgaris, Populus deltoids, Populus trichocarpa, Prunus persica, Solanum tuberosum, Thellungiella salsuginea*, and *Trifolium pratense*.

Common crop plants which are targets of the present invention include: *Arabidopsis thalina, Brassica napus, Brassica juncea, barrel clover, turfgrass, Zea mays*, soybean, wheat, rice, barley, sunflower, safflower, rapeseed, tobacco, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, olive, pepper, potato, eggplant and tomato.

Many applications for expression of BKI1-type polypeptides or modulators to influence phenotype in the above plants will be apparent to persons of skill. These include: greater density and slower growth for turfgrasses such as those found in lawns and golf courses; increased yield for favorable architecture and dense plantings of rice, corn, sorghum, sugar cane, wheat, barley, millet, and other Gramineae, production of dwarf plants, production of dwarf varieties of fruit and nut trees that produce normal or large fruit or nuts, production of larger shade trees, production of larger seeds, fruits, nuts and other plant tissues or organs of commercial importance, and many others.

Expression Cassettes

In construction of a recombinant expression cassette of the invention, a plant promoter fragment is optionally employed which directs expression of a nucleic acid in any or all tissues of a regenerated plant. Indeed, in one application, bki1 genes are desirably constitutively expressed, thereby inhibiting brassinosteroid signaling (e.g., to produce dwarf plants). Examples of constitutive promoters are found herein and in the references cited herein. Alternatively, the plant promoter may direct expression of the polynucleotide of the invention in a specific tissue (tissue-preferred or specific promoters), such as leaves, fruit, seeds or other sites where regulation of the brassinosteroid signaling pathway is desired. Examples of tissue-preferred/specific promoters under developmental control include promoters that initiate transcription only in certain tissues, such as fruit, seeds or flowers. Extensive examples of such promoters are found herein. Inducible promoters can also be used, as discussed herein.

If expression of a polypeptide from a BKI1 gene or modulator thereof is desired, a polyadenylation region at the 3'-end of the coding region can be included in the recombinant construct. The polyadenylation region can be derived from the natural gene, from a variety of other plant genes, or from, e.g., T-DNA.

The expression vector comprising cassette sequences (e.g., promoters or coding regions) and genes encoding expression products and transgenes of the invention will typically also include a marker that confers an easily selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after a recombinant expression cassette from such a vector is stably incorporated in a transgenic plant and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected BKI1-type polypeptide or modulator producing phenotype. Parts obtained from the regenerated plant, such as flowers, seeds, leaves, branches, fruit, and the like are included in the invention. Progeny and variants, and mutants of the regenerated plants are also included within the scope of the invention, provided, e.g., that these plants comprise the introduced BKI1 type polypeptide or modulator genes.

Transgenic or introgressed plants expressing a polynucleotide of the present invention can be screened for transmission of the nucleic acid of the present invention by, for example, standard nucleic acid detection methods (marker assisted selection) or by immunoblot protocols. Expression at the RNA level can be monitored to identify and quantify expression-positive plants. Standard techniques for RNA analysis can be employed and include RT-PCR amplification assays using oligonucleotide primers designed to amplify only heterologous or introgressed RNA templates and solution hybridization assays using marker or linked QTL specific probes. Plants can also be analyzed for protein expression, e.g., by Western immunoblot analysis using antibodies that recognize BKI1-type polypeptides. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment of the invention is a transgenic plant that is homozygous for the added heterologous nucleic acid that encodes a BKI1 polypeptide or modulator; e.g., a diploid transgenic plant that contains two added nucleic acid sequence copies of the nucleic acids, e.g., a recombinant gene at the same locus on each chromosome of a homologous chromosome pair. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide of the present invention relative to a control plant (e.g., a native, non-transgenic plant). Back-crossing to a parental plant and out-crossing with a non-transgenic plant can be used to introgress the heterologous nucleic acid into a selected background (e.g., an elite or exotic plant line).

Modulating Brassinosteroid Responses

In the present invention, brassinosteroid responses are modulated by overexpressing BKI1-type polypeptides in whole plants, or in selected cells or tissues, or by expressing or applying modulators thereof to the plant. Brassinosteroids comprise a class of more than 40 plant polyhydroxylated sterol derivatives that regulate, e.g., the size and architecture of plants. The brassinosteroids regulate cell elongation, vascular development, stress tolerance, seed size, fertility, flowering time, senescence, etc. Without being limited to any particular mechanism(s), the overall brassinosteroid signaling pathway is described schematically in FIG. 1K. As shown, Arabidopsis biosynthetic mutants that do not produce brassinolide (BL) are dwarf (upper left photo) but can be rescued to full stature by exogenous application of BL (upper right photo).

Brassinosteroid synthesis pathways are also complex, and can include redundant synthetic elements. For example, loss of function of OsDWARF4, a cytochrome P450 gene responsible for C-22 hydroxylation (a rate limiting step in brassinosteroid synthesis) in rice, results in nominally shorter rice plants with increased leaf erectness. This provides for denser planting of crops and increased yield, without use of additional fertilizers. However, loss of function of a different P450 C-22 hydroxylase in rice, OsDWARF4L1, results in small seeds and overall dwarfism. See, e.g., Feldmann (2006) "Steroid Regulation Improves Crop Yeild" *Nature Biotechnology* 24(1): 46-47 and Sakamoto et al. (2006) "Erect Leaves Caused by Brassinosteroid Deficiency Increase Biomass Production and Grain Yeild in Rice." *Nature Biotechnology* 24(1): 105-109. The various effects of brassinosteroid synthesis mutations can be combined with BKI1 overexpression (e.g., caused by recombinant expression of BKI1) or under expression (e.g., caused by expression of BKI1 inhibitors such as RNAi). Further details on these applications are described below.

As schematically illustrated in FIG. 1K, BR signaling mutants (lower left photo) are not rescued by application of exogenous BL. In the absence of BRs such as BL, the kinase domains of the BRI1 homodimer are inhibited by both their own C-terminal domain and by an interaction with BKI1. This allows the GSK3 homolog, BIN2, to phosphorylate and inactivate the brassinosteroid response transcription factors (BRFs), including BES1 and BZR1. Under normal conditions, direct binding of BL to BRI1 homodimers results in conformational changes of the kinase domain, leading to phosphorylation of the C-terminal domain of BRI1 and phosphorylation of BKI1, which causes displacement of BKI1 from the plasma membrane and the release of autoinhibition of BRI1. In the present invention, this step in the BR signaling pathway can be influenced by over or under expressing BRI1; that is, where BKI1 is overexpressed, the effects of BRs on signaling will be reduced, because of excess BKI1. Contrawise, if BKI1 is underexpressed, BR signaling will be potentiated.

Phosphorylation of BKI1 and release of BRI1 autoinhibition leads to BRI1's association with BAK1 and consequent activation of the receptor. The resulting active signaling receptor complex inhibits the activity of BIN2, allowing dephosphorylation of the BRFs by BSU1 and activation or repression of their target genes and optimal plant growth (lower right photo). The horseshoe-shaped representations of BRI1 and BAK1 LRR domains, as well as the putative LRR (red domains) interactions, are inferred from structural models of LRR-containing proteins. The atypical LRR21 is represented by a yellow domain. The BL docking into the binding site is speculative. Phosphorylation events are indicated by a circled P. See also, Belkhadir and Chory (2006) "Brassinosteroid Signaling: A Paradigm for Steroid Hormone Signaling from the Cell Surface" *Science* 314 (5804): 1410-1411; and Wang and Chory. (2006) "Brassinosteroids regulate dissociation of BKI1, a negative regulator of BRI1 signaling, from the plasma membrane," *Science* 313:1118-1122.

Control of brassinosteroid signaling is used to influence yield and other traits of interest. These include: decreased sensitivity to brassinosteroids, increased sensitivity to brassinosteroids, improved yield under dense planting conditions, increased leaf erectness, stress tolerance, increased tolerance to biotic or abiotic stress, decreased tolerance to biotic or abiotic stress, enhanced dwarfism, increased stature, decreased stature, increased stem length, decreased stem length, altered vascular differentiation, increased seed size, decreased seed size, increased fertility, decreased fertility, increased time to senescence, decreased time to senescence, increased hypocotyl length, decreased hypocotyl length, accelerated flowering, delayed flowering, increased petiole length, decreased petiole length, increased cell elongation, decreased cell elongation, rounded leaves, and combinations thereof. The ability to fine-tune effects by expressing recombinant BKI1 (and/or recombinant modulators thereof) in selected plant tissues provides one of skill with the ability to fine tune desired phenotypic traits, e.g., by expressing BKI1 in one tissue (e.g., leaves) while not expressing it in others (e.g., seeds) leading, e.g., to increased yield.

Combinations of Brassinosteroid Regulators to Achieve Desired Phenotypes

BKI1-type polypeptides are described herein as brassinosteroid signaling pathway regulators. As already discussed in detail above, a proposed mechanism for this regulation is described in FIG. 1K. In the absence of BRs, the kinase domains of the BRI1 homodimer are inhibited by both their own C-terminal domain and by an interaction with BKI1. This allows BIN2 to phosphorylate and inactivate the brassinosteroid response transcription factors (BRFs). Direct binding of BL to BRI1 homodimers results in conformational changes of the kinase domain, leading to the phosphorylation of the C-terminal domain of BRI1 and phosphorylation of BKI1, which causes displacement of BKI1 from the plasma membrane and the release of autoinhibition of BRI1. These events lead to BRI1's association with BAK1 and consequent activation of the receptor. Thus, overexpression of BKI1 results in reduced BRI1 dependent signaling (see also, the examples below). Modulators of BKI1 expression levels can be used to increase (or decrease) BKI1-mediated BRI1 signal inhibition.

In one aspect, the invention provides for a combination of BKI1-type polypeptide BR response pathway modulation in a plant, in combination with one or more additional BR regulator(s), e.g., as set forth in FIG. 1K. A variety of BRI1 and other mutants are known and can also affect BR signaling. Furthermore, as noted above, other enzymes that influence brassinosteroid levels (and, thus, signaling) are also known, e.g., genes that encode enzymes that synthesize brassinosteroids; expression levels of these enzymes can also be regulated in concert with BKI1 to achieve phenotypic effects resulting from brassinosteroid pathway modifications. As already noted, loss of function of OsDWARF4, a cytochrome P450 gene responsible for C-22 hydroxylation (a rate limiting step in brassinosteroid synthesis) in rice, results in nominally shorter rice plants with increased leaf erectness. This provides for denser planting of crops and increased yield, without use of additional fertilizers. Loss of function of a different P450 C-22 hydroxylase in rice, OsDWARF4L1, results in small seeds and overall dwarfism. See, e.g., Feldmann (2006) and Sakamoto et al. (2006) (above). The quantitative phenotypic effects of these genes can be combined with BKI1 expression or repression in one or more tissues to achieve particular brassinosteroid pathway modification dependent phenotypic effects.

Additional examples of genes that can be modified in concert with BKI1 include dwarf (d2) and dwarf11 (Hong et al. (2003) "A rice brassinosteroid-deficient mutant, ebisu dwarf (d2), is caused by a loss of function of a new member of cytochrome P450." *Plant Cell* 15:2900-2910; Tanabe et al. (2005) "A novel cytochrome P450 is implicated in brassinosteroid biosynthesis via the characterization of a rice dwarf mutant, dwarf11, with reduced seed length. *Plant Cell* 17:776-790.

Details Regarding Sequence Comparison, Identity, and Homology

"Identity" or "similarity" in the context of two or more nucleic acid or polypeptide sequences, refers to the degree of sequence relatedness of the sequences. Typically, the sequences are aligned for maximum correspondence, and the percent identity or similarity is measured using a commonly available sequence comparison algorithm, e.g., as described below (other algorithms are available to persons of skill and can readily be substituted). Similarity can also be determined simply by visual inspection. Preferably, "identity" or "similarity" exists over a region of the sequences that is at least about 50 residues in length, more preferably over a region of at least about 100 residues, and most preferably the sequences are related over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described, e.g., in Altschul et al., *J. Mol. Biol.* 215:403-410 (1990) and by Gish et al. (1993) "Identification of protein coding regions by database similarity search" *Nature Genetics* 3:266-72. Software for performing BLAST analyses is publicly available through the National Center for Biotechnology Information (www(dot)ncbi(dot)nlm(dot)nih(dot)gov/) and from Washington University (Saint Louis) at www(dot)blast(dot)wustl(dot)edu/. WU-blast 2.0 (e.g., recent release date Mar. 22, 2006) provides one convenient implementation of BLAST.

In general, this algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Details Regarding Mutation of BKI1-Type Nucleic Acids and Encoded Polypeptides

The sequence of any available bki1-type nucleic acid and encoded polypeptide (including any of those specifically noted herein or publicly available) can be modified by standard methods to provide variants of such available sequences, including conservative or non-conservative variants. Any available mutagenesis procedure can be used to modify a given nucleic acid. Such mutagenesis procedures optionally include selection of mutant nucleic acids and polypeptides for one or more activity of interest (e.g., increased or decreased responsiveness to BRs, phenotypic effects, tissue-specificity, etc.). Procedures that can be used include, but are not limited to: site-directed point mutagenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, and many others known to persons of skill. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like. In another class of embodiments, modification is essentially random (e.g., as in classical DNA shuffling).

Additional information regarding mutation is found in the following publications and references cited within: Arnold, *Protein engineering for unusual environments, Current Opinion in Biotechnology* 4:450-455 (1993); Bass et al., *Mutant Trp repressors with new DNA-binding specificities, Science* 242:240-245 (1988); Botstein & Shortle, *Strategies and applications of in vitro mutagenesis, Science* 229:1193-1201 (1985); Carter et al., *Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA procedure without enzymatic reactions in vitro, Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Kunkel, *The efficiency of oligonucleotide directed mutagenesis*, in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA*, 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Sieber, et al., *Nature Biotechnology*, 19:456-460 (2001); Smith, *In vitro mutagenesis, Ann. Rev. Genet.* 19:423-462 (1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R. Soc. Lond. A* 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); and Zoller & Smith, *Oligonucleotide-directed mutagenesis: a simple method using two oligonucleotide primers and a single-stranded DNA template, Methods in Enzymol.* 154:329-350 (1987). Additional details on many of the above methods can be found in *Methods in Enzymology* Volume 154, which also describes useful controls for trouble-shooting problems with various mutagenesis methods.

Accordingly, any of a variety of BKI1-type polypeptides or nucleic acids can be made or used in the present invention. These include the various homologues noted above, as well as a variety of nucleic acids that encode any such homologous polypeptides. One of skill will appreciate that, due to the degeneracy of the genetic code, a variety of nucleic acids can encode any given polypeptide. In addition, such nucleic acids optionally include any of a variety of promoters, expression vector nucleic acids, linker sequences, tag sequences, labels, or the like. Examples of such sequences are provided in the Examples section herein and are further available in public databases.

BKI1 Polypeptides that Include Tags, Labels and Linkers

BKI1-type polypeptides can include tags, labels, linkers, and/or the like. These are useful as purification handles, e.g., to track expression of recombinant BKI1-type polypeptides, etc. Many such tags/labels/linkers are known in the art and can be adapted to the practice of the present invention by being incorporated into BKI1-type polypeptides. For examples of general strategies for protein tagging and labeling, see, e.g.: Nilsson et al. (1997) "Affinity fusion strategies for detection, purification, and immobilization of recombinant proteins" Protein Expression and Purification 11: 1-16, Terpe et al. (2003) "Overview of tag protein fusions: From molecular and biochemical fundamentals to commercial systems" Applied Microbiology and Biotechnology 60:523-533, and references therein). Tags that can be used to couple the polypeptides to a surface for screening applications (e.g., to identify BKI1-type polypeptide binders, or molecules that inhibit BKI1-BRI1 type interactions) can also be used. These include, but are not limited to, polyhistidine tags (e.g., a His-6, His-8, or His-10 tag) that binds immobilized divalent cations (e.g., $Ni^{2+}$), a biotin moiety (e.g., on an in vivo biotinylated polypeptide sequence) that binds immobilized avidin, a GST (glutathione S-transferase) sequence that binds immobilized glutathione, an S tag that binds immobilized S protein, an antigen that binds an immobilized antibody or domain or fragment thereof (including, e.g., T7, myc, FLAG, and B tags that bind corresponding antibodies), a FLASH Tag (a high affinity tag that couples to specific arsenic based moieties), a receptor or receptor domain that binds an immobilized ligand (or vice versa), protein A or a derivative thereof (e.g., Z) that binds immobilized IgG, maltose-binding protein (MBP) that binds immobilized amylose, an albumin-binding protein that binds immobilized albumin, a chitin binding domain that binds immobilized chitin, a calmodulin binding peptide that binds immobilized calmodulin, and a cellulose binding domain that binds immobilized cellulose.

One or more specific protease recognition sites are optionally included in a linker, for example, between tags and a BKI1 polypeptide domain. Examples of specific proteases include, but are not limited to, thrombin, enterokinase, factor Xa, TEV protease, and HRV 3C protease. Similarly, an intein sequence can be incorporated into a linker (e.g., an intein that undergoes specific self cleavage in the presence of free thiols). Such protease cleavage sites and/or inteins are optionally used to remove a tag used for purification of the BKI1-type polypeptide and/or for releasing the polypeptide from a surface or purification media.

Additional Details Regarding Sequence Variations

A number of particular BKI1 polypeptides and coding nucleic acids are described herein by sequence (See, e.g., the Examples below and the various Genebank accession numbers that are noted). These polypeptides and coding nucleic acids can be modified, e.g., by mutation as described herein, or simply by artificial synthesis of a desired variant. Several types of example variants are described below.

Silent Variations

Due to the degeneracy of the genetic code, any of a variety of nucleic acids sequences encoding polypeptides of the invention are optionally produced, some which can bear lower levels of sequence identity to the Arabadopsis thalinia bki1 gene than the various homologous species found at AJ796385.1 (SEQ ID NO:20), AJ796560.1 (SEQ ID NO:21), CX674446.1 (SEQ ID NO:22), DY389957.1 (SEQ ID NO:23), BU579318.1 (SEQ ID NO:24), BE609508.1 (SEQ ID NO:25), BE609498.1 (SEQ ID NO:26), AW620804.1 (SEQ ID NO:27), DY946533.1 (SEQ ID NO:28), BJ557111.1 (SEQ ID NO:29), BJ575601.1 (SEQ ID NO:30), DY971277.1 (SEQ ID NO:31), BQ867285.1 (SEQ ID NO:32), BE130683.1 (SEQ ID NO:33), CK287132.1 (SEQ ID NO:34), EB435640.1 (SEQ ID NO:35), BQ481779.1 (SEQ ID NO:36), CX170112.1 (SEQ ID NO:37), CX175441.1 (SEQ ID NO:38), CX175253.1 (SEQ ID NO:39), DT481968.1 (SEQ ID NO:40), DT487361.1 (SEQ ID NO:41), DY636517.1 (SEQ ID NO:42), CX162638.1 (SEQ ID NO:43), DN773886.1 (SEQ ID NO:44) and BB923413.1 (SEQ ID NO:45). The following provides a typical codon table specifying the genetic code, found in many biology and biochemistry texts.

TABLE 1PP

Codon Table

| Amino acids | | | Codon | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |

TABLE 1PP-continued

Codon Table

| Amino acids | | | Codon | |
|---|---|---|---|---|
| Tryptophan | Trp | W | UGG | |
| Tyrosine | Tyr | Y | UAC | UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations", discussed below. One of skill will recognize that each codon in a nucleic acid (except ATG, which is ordinarily the only codon for methionine) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1PP, or as is commonly available in the art) as applied to the nucleic acid sequence encoding a BKI1-type polypeptide of the invention. All such variations of every nucleic acid herein are specifically provided and described by consideration of the sequence in combination with the genetic code. One of skill is fully able to make these silent substitutions using the methods herein.

Conservative Variations

"Conservatively modified variations" or, simply, "conservative variations" of a particular nucleic acid sequence or polypeptide are those which encode identical or essentially identical amino acid sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2PP sets forth six groups which contain amino acids that are "conservative substitutions" for one another.

TABLE 2PP

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Thus, "conservatively substituted variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

Finally, the addition or deletion of sequences which do not alter the encoded activity of a nucleic acid molecule, such as the addition or deletion of a non-functional sequence, is a conservative variation of the basic nucleic acid or polypeptide.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

Isolating BKI1 Polypeptides from Natural or Recombinant Sources

Purification of BKI1-type polypeptides is useful, e.g., for obtaining crystal structure information for the polypeptides, e.g., to design mimetic molecules that can interact with BRI1. Purified BKI1-type polypeptides can also be used to make antibodies to the polypeptides, which are useful for purifying and labeling the polypeptide, e.g., for in situ analysis of tissue and cellular distribution of the polypeptides. Antibodies can also modulate BKI1-type polypeptide function, e.g., by binding to the polypeptide and either blocking its interaction with BRI1, or serving to anchor the BKI1-type polypeptide in the membrane, thereby increasing its activity.

Purification can be accomplished using known techniques. Generally, cells expressing the proteins (naturally or by recombinant methods) are lysed, crude purification occurs to remove debris and some contaminating proteins, followed by chromatography to further purify the protein to the desired level of purity. Cells can be lysed by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well known techniques for refolding proteins can be used to obtain the active conformation of the protein when the protein is denatured during recombinant or natural synthesis, isolation or purification.

In general, BKI1 proteins can be purified, either partially (e.g., achieving a 5×, 10×, 100×, 500×, or 1000× or greater purification), or even substantially to homogeneity (e.g., where the protein is the main component of a solution, typically excluding the solvent (e.g., water, crystallization buffer, DMSO, or the like) and buffer components (e.g., salts and stabilizers) that the polypeptide is suspended in, e.g., if the polypeptide is in a liquid phase), according to standard procedures known to and used by those of skill in the art. Accordingly, polypeptides of the invention can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against BKI1-type polypeptides are used as purification reagents, e.g., for affinity-based purification. Once purified, partially or to homogeneity, as desired, the polypeptides are optionally used e.g., as assay components, reagents, crystallization materials, or, e.g., as immunogens for antibody production.

In addition to other references noted herein, a variety of purification/protein purification methods are well known in the art, including, e.g., those set forth in R. Scopes, *Protein Purification*, Springer-Verlag, N.Y. (1982); Deutscher, *Methods in Enzymology Vol.* 182*: Guide to Protein Purification*, Academic Press, Inc. N.Y. (1990); Sandana (1997) *Bioseparation of Proteins*, Academic Press, Inc.; Bollag et al. (1996) *Protein Methods,* 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3*rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

Those of skill in the art will recognize that, after synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from, e.g., lysates derived from *E. coli*, the expressed protein is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

BKI1 nucleic acids optionally comprise a coding sequence fused in-frame to a sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the sequence of the invention is useful to facilitate purification.

Making Antibodies to BKI1-Type Polypeptides

Antibodies to BKI1-type polypeptides are useful for monitoring in cellular, subcellular and situ localization of the BKI1-type polypeptides. Antibodies are also useful for affinity purification, and, generally, as detection reagents for detecting BKI1-type polypeptides. Antibodies can also, in some cases, be used to block function of BKI1-type polypeptides, in vivo, in situ or in vitro (e.g., by binding to BKI1). Accordingly, antibodies can be modulators of BKI1-type polypeptides.

As used herein, the term "antibody" includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a polypeptide encoded by a BKI1-type polypeptide, or a conservative variant or fragment thereof, various host animals may be immunized by injection with the polypeptide, or a portion thereof. Such host animals may include, but are not limited to, rabbits, mice and rats, to name but a few. Various adjuvants may be used to enhance the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495-497, 1975; and U.S. Pat. No. 4,376,110), the human B-cell hybridoma technique (Kosbor et al., *Immunology Today* 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy*, Alan R. Liss, Inc., pp. 77-96, 1985). Such antibodies may be of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

Alternatively, techniques described for the production of single-chain antibodies (U.S. Pat. No. 4,946,778; Bird, *Science* 242:423-426, 1988; Huston et al., *Proc. Nat'l. Acad. Sci. USA* 85:5879-5883, 1988; and Ward et al., *Nature* 334:544-546, 1989) can be adapted to produce differentially expressed gene-single chain antibodies. Single chain antibodies are formed by linking the heavy and light chain fragments of the Fv region via an amino acid bridge, resulting in a single-chain polypeptide.

Antibody fragments which recognize specific epitopes may be generated by known techniques. For example, such fragments include, but are not limited to, the $F(ab')_2$ fragments, which can be produced by pepsin digestion of the antibody molecule, and the Fab fragments, which can be generated by reducing the disulfide bridges of the $F(ab')_2$ fragments. Alternatively, Fab expression libraries may be constructed (Huse et al., Science 246:1275-1281, 1989) to allow rapid and easy identification of monoclonal Fab fragments with the desired specificity.

The protocols for detecting and measuring the expression of the described polypeptides herein, using the above mentioned antibodies, are well known in the art. Such methods include, but are not limited to, in situ immunoflourescence, dot blotting, western blotting, competitive and noncompetitive protein binding assays, enzyme-linked immunosorbant assays (ELISA), immunohistochemistry, fluorescence-activated cell sorting (FACS), and others commonly used and widely described in scientific, commercial and patent literature.

Selecting Plants for BKI1 Polymorphisms

Marker assisted selection (MAS) is routinely performed to select crop varieties for one or more trait of interest. The development of molecular genetic markers has facilitated mapping and selection of agriculturally important traits in essentially every plant of commercial interest. Markers tightly linked to genes (in this case, bki1 genes) that influence phenotype are a substantial asset in the rapid identification of plant lines that comprise phenotype of interest, with the markers being used as an easily screenable proxy for the actual phenotype. Introgressing bki1 genes into a desired cultivar (e.g., an elite crop line) is also facilitated by using suitable markers. For example, with the knowledge that bki1 encodes a quantitative trait that influences leaf erectness, dwarfisim, and many other phenotypes as noted herein, polymorphic markers linked to specific alleles of bki1 can be used as proxies for selecting for particular allelic differences. A variety of allelic variants and linked markers for many different bki1 genes are available upon inspection of plant genomic database information. For many commercially relevant crops such as soybean, rice, corn, potato, and others, dense maps of allelic variation are available.

Molecular Markers and Marker Assisted Selection

A genetic map is a graphical representation of a genome (or a portion of a genome such as a single chromosome) where the distances between landmarks on the chromosome are measured by the recombination frequencies between the landmarks. A genetic landmark can be any of a variety of known polymorphic markers, for example but not limited to, molecular markers such as SSR markers, RFLP markers, or SNP markers. Furthermore, SSR markers can be derived from genomic or expressed nucleic acids (e.g., ESTs). The nature of these physical landmarks and the methods used to detect them vary, but all of these markers are physically distinguishable from each other (as well as from the plurality of alleles of any one particular marker) on the basis of polynucleotide length and/or sequence.

Although specific DNA sequences which encode proteins are generally well-conserved across a species, other regions of DNA (typically non-coding) tend to accumulate polymorphisms, and therefore, are likely to be variable between individuals of the same species. Such regions provide the basis for numerous molecular genetic markers. In general, any differentially inherited polymorphic trait (including a nucleic acid polymorphism) that segregates among progeny is a potential marker. The genomic variability can be of any origin, for example, insertions, deletions, duplications, repetitive elements, point mutations, recombination events, or the presence and sequence of transposable elements. Similarly, numerous methods for detecting molecular markers are also well-established.

The primary motivation for developing molecular marker technologies from the point of view of plant breeders has been the possibility to increase breeding efficiency through marker assisted selection (MAS). A molecular marker allele that demonstrates linkage disequilibrium with a desired phenotypic trait (e.g., a quantitative trait locus, or QTL, such as resistance to a particular disease) provides a useful tool for the selection of a desired trait in a plant population. The key components to the implementation of this approach are: (i) the creation of a dense genetic map of molecular markers, (ii) the detection of QTL based on statistical associations between marker and phenotypic variability, (iii) the definition of a set of desirable marker alleles based on the results of the QTL analysis, and (iv) the use and/or extrapolation of this information to the current set of breeding germplasm to enable marker-based selection decisions to be made.

Two types of markers are frequently used in marker assisted selection protocols, namely simple sequence repeat (SSR, also known as microsatellite) markers, and single nucleotide polymorphism (SNP) markers. The term SSR refers generally to any type of molecular heterogeneity that results in length variability, and most typically is a short (up to several hundred base pairs) segment of DNA that consists of multiple tandem repeats of a two or three base-pair sequence. These repeated sequences result in highly polymorphic DNA regions of variable length due to poor replication fidelity, e.g., caused by polymerase slippage. SSRs appear to be randomly dispersed through the genome and are generally flanked by conserved regions. SSR markers can also be derived from RNA sequences (in the form of a cDNA, a partial cDNA or an EST) as well as genomic material.

The characteristics of SSR heterogeneity make them well suited for use as molecular genetic markers; namely, SSR genomic variability is inherited, is multiallelic, codominant and is reproducibly detectable. The proliferation of increasingly sophisticated amplification-based detection techniques (e.g., PCR-based) provides a variety of sensitive methods for the detection of nucleotide sequence heterogeneity. Primers (or other types of probes) are designed to hybridize to conserved regions that flank the SSR domain, resulting in the amplification of the variable SSR region. The different sized amplicons generated from an SSR region have characteristic and reproducible sizes. The different sized SSR amplicons observed from two homologous chromosomes in an individual, or from different individuals in the plant population are generally termed "marker alleles." As long as there exists at least two SSR alleles that produce PCR products with at least two different sizes, the SSRs can be employed as a marker.

Various techniques have been developed for the detection of polymorphisms, including allele specific hybridization (ASH; see, e.g., Coryell et al., (1999) "Allele specific hybridization markers for soybean," *Theor. Appl. Genet.*, 98:690-696). Additional types of molecular markers are also widely used, including but not limited to expressed sequence tags (ESTs) and SSR markers derived from EST sequences, restriction fragment length polymorphism (RFLP), amplified fragment length polymorphism (AFLP), randomly amplified polymorphic DNA (RAPD) and isozyme markers. A wide range of protocols are known to one of skill in the art for detecting this variability, and these protocols are frequently specific for the type of polymorphism they are designed to detect. For example, PCR amplification, single-strand conformation polymorphisms (SSCP) and self-sustained sequence replication (3SR; see Chan and Fox, "NASBA and other transcription-based amplification methods for research and diagnostic microbiology," Reviews in Medical Microbiology 10:185-196 [1999]).

Linkage of one molecular marker to another molecular marker is measured as a recombination frequency. In general, the closer two loci (e.g., two SSR or SNP markers) are on the genetic map, the closer they lie to each other on the physical map. A relative genetic distance (determined by crossing over frequencies, measured in centimorgans; cM) is generally proportional to the physical distance (measured in base pairs, e.g., kilobase pairs [kb] or megabasepairs [Mbp]) that two linked loci are separated from each other on a chromosome. A lack of precise proportionality between cM and physical distance can result from variation in recombination frequencies for different chromosomal regions, e.g., some chromosomal regions are recombinational "hot spots," while others regions do not show any recombination, or only demonstrate rare recombination events. In general, the closer one marker is to another marker, whether measured in terms of recombination or physical distance, the more strongly they are linked. In some aspects, the closer a molecular marker is to a BKI1 gene that imparts a particular phenotype (e.g., leaf erectness, dwarfisim, etc.), whether measured in terms of recombination or physical distance, the better that marker serves to tag the desired phenotypic trait.

Techniques for Marker Detection

Markers corresponding to genetic polymorphisms (e.g., a BKI1 gene or regulator or variation thereof) between members of a population can be detected by methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic plant DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York, as well as in Sambrook, Berger and Ausubel (herein).

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected (e.g., a BKI1 gene or regulator or fragment thereof) to restriction digested genomic DNA. The restriction enzyme is selected to provide restriction fragments of at least two alternative (or polymorphic) lengths in different individuals or populations. Determining one or more restriction enzyme that produces informative fragments for each cross is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.) (Available on CD ROM).

Detection of Markers for Positional Cloning

In some embodiments, a nucleic acid probe is used to detect a nucleic acid that comprises a marker sequence. Such probes can be used, for example, in positional cloning to isolate nucleotide sequences (e.g., BKI1 coding nucleic acid) linked to the marker nucleotide sequence. It is not intended that the nucleic acid probes of the invention be limited to any particular size. In some embodiments, nucleic acid probe is at least 20 nucleotides in length, or alternatively, at least 50 nucleotides in length, or alternatively, at least 100 nucleotides in length, or alternatively, at least 200 nucleotides in length.

A hybridized probe is detected using, autoradiography, fluorography or other similar detection techniques depending on the label to be detected. Examples of specific hybridization protocols are widely available in the art, see, e.g., Berger, Sambrook, and Ausubel, all herein.

EXAMPLES

The following example serves to illustrate, but not to limit the claimed invention. One of skill will recognize a variety of non-critical parameters that can be altered to achieve essentially similar results.

Example 1

Brassinosteroids Regulate Dissociation of BKI1, a Negative Regulator of BRI1 Signaling, from the Plasma Membrane Brassinosteroids, the steroid hormones of plants, are perceived at the plasma membrane by a leucine-rich repeat receptor serine/threonine kinase, called BRI1. We show in this example that a BRI1-interacting protein, BKI1, is a negative regulator of brassinosteroid signaling. Brassinosteroids cause the rapid dissociation of BKI1-yellow fluorescent protein (YFP) from the plasma membrane in a process that is dependent on BRI1-kinase. BKI1 is a substrate of BRI1 kinase and limits the interaction of BRI1 with its proposed co-receptor, BAK1, indicating that BKI1 prevents the activation of BRI1.

To investigate the signaling events between the plasma membrane and transcriptional responses, we searched for proteins that interact with BRI1 using yeast two-hybrid screens of a cDNA library from *Arabidopsis* shoot apical meristems. We repeatedly identified two proteins that interacted with the intracellular domains of wild-type or kinase inactive BRI1: a transthyretin-like protein (TTL), which is a negative regulator of brassinosteroid-related plant growth (18), and an expressed protein of unknown function, At5g42750. We designated At5g42750 as BKI1 for BRI1 Kinase Inhibitor 1. BKI1 is predicted to encode a protein of 337 amino acids with two separate Serine-rich domains and an Asn-rich region (SMART, Simple Modular Architecture Research Tool, http://smart.emblheidelberg.de) (FIG. 1A). BLAST searches of the predicted BKI1 amino acid sequence identified a similar gene in rice, as well as multiple ESTs from other angiosperms, which in several cases appear to contain the entire predicted coding region (FIG. 1B and Table 1). The rice protein has been reported to interact with the kinase domain of rice BRI1, although its function is unknown (19). No other significant similarities were identified in other species, suggesting that BKI1 may be angiosperm-specific.

Sequence alignments indicated that the C-terminal domain of BKI1 is the most conserved region (about 32% identity in the C-terminal region (residues 253-337)). The C-terminus was both necessary and sufficient to bind BRI1-KD (FIG. 1C). BKI1 associated specifically with the kinase domain of BRI1, and not with TTL, BIN2, or kinase domains of other receptor-like kinases tested, including BAK1 and NIK1, another member of the BAK1 subfamily (FIG. 1D). BKI1 did not interact with CLV1, an LRR-RLK involved in shoot apical meristem development (1), nor did it interact with BRI1's closest relatives, BRL1 and BRL3 (20) (FIG. 6), indicating that the interaction of BKI1 with BRI1 is highly specific. GST pull-down experiments using GST-BRI1-KD and S-35 Met labeled BKI1-6×HIS further indicated that BKI1 interacts with the kinase domain of BRI1 (FIG. 1E). Immunoprecipitation experiments confirmed that endogenous BRI1 interacted with a BKI1-FLAG fusion protein in vivo (FIG. 1F).

Figure 2A:
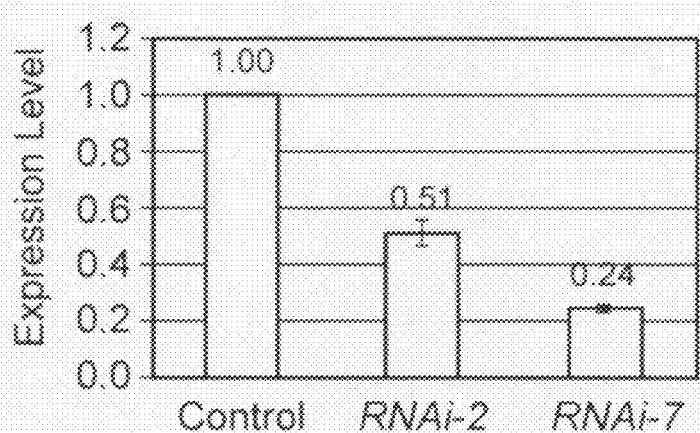
FIG. 2A is a histogram showing expression level of BKI1 in RNAi knockdown plants and a control line determined by qRT-PCR.
Figure 2B:
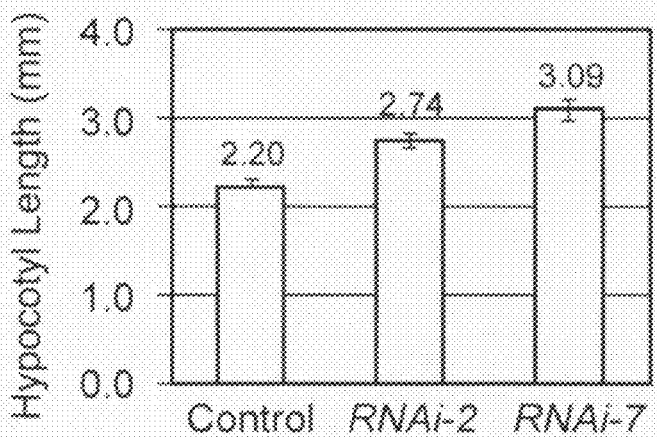
FIG. 2B is a histogram showing that suppression of BKI1 expression leads to longer hypocotyls.
Figure 2C:
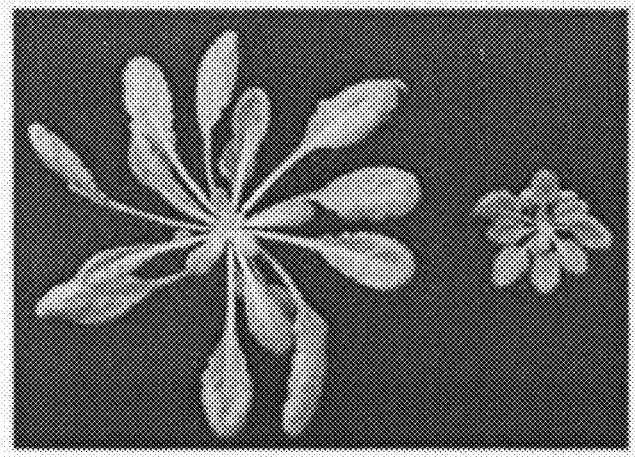
FIG. 2C shows Short-day grown seedlings.
Figure 2D:
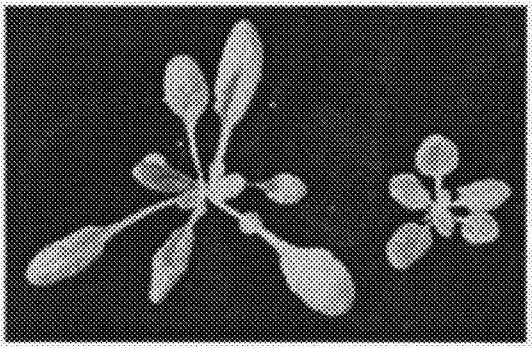
FIG. 2D. shows long-day grown seedlings.
Figure 2E:
FIG. 2E shows long-day grown adult plants.

BKI1's function in brassinosteroid signaling was explored in several ways. First, we made transgenic plants harboring a β-glucuronidase (GUS) reporter gene expressed from the promoter of BKI1 to observe the expression pattern of BKI1 (FIG. 1G-J) during development. BKI1 was expressed in leaves, petioles, shoot apices, hypocotyls, roots, and flowers, indicating that BKI1 and BRI1 are co-expressed in a number of tissues (21). To explore the function of BKI1 in BRI1 signaling, we created RNAi (RNA interference) lines to knockdown BKI1 RNA levels. Real-time quantitative RT-PCR (qRT-PCR) analysis indicated that the transcript level of BKI1 was significantly reduced (50% to 76%) in many RNAi lines, compared to a control line, (FIG. 2A). The RNAi lines had longer hypocotyls than the control line grown in short days (Control: 2.20±0.09 mm; RNAi-2: 2.74±0.08 mm; and RNAi-7: 3.09±0.12 mm), and the levels of BKI1 transcripts were negatively correlated with hypocotyl length, suggesting that BKI1 represses brassinosteroid-related growth (FIG. 2B). In contrast, over-expression of BKI1 with either a FLAG or YFP tag resulted in dwarf plants resembling plants harboring weak alleles of bri1. These plants had a smaller rosette (under both short-day and long-day conditions), reduced stature and petiole length, rounder rosette leaves, and delayed flowering compared with wild type (FIG. 2C-F).

Figure 2F:
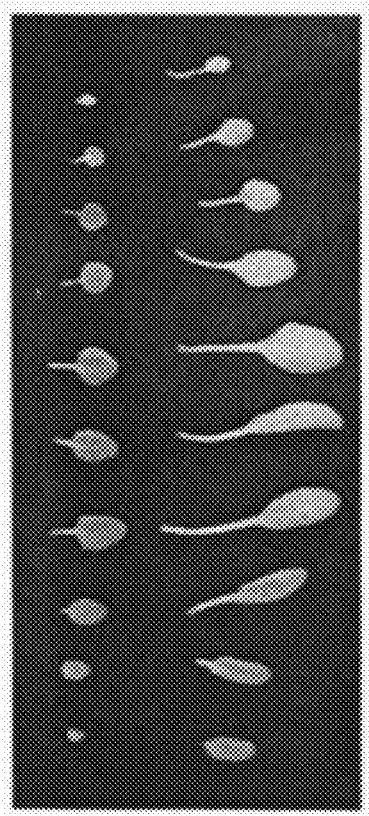
FIG. 2F shows leaf morphology of seedlings grown in short days. Col-0 (right) and a BKI1-FLAG line (left) are shown.
Figure 2G:
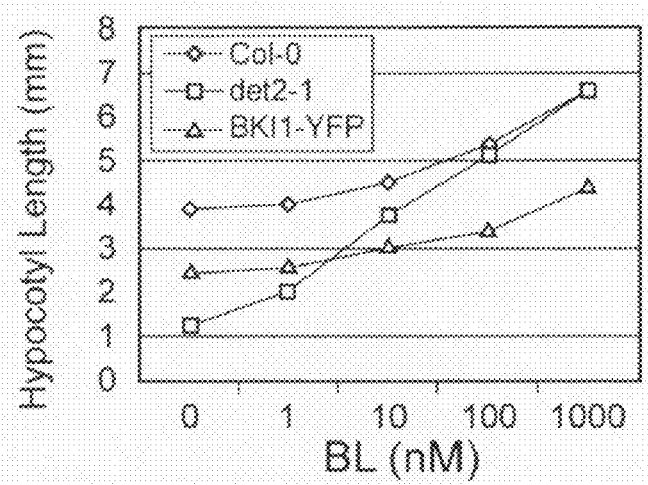
FIG. 2G is a histogram showing that over-expression of BKI1-YFP leads to a reduced response (hypocotyl length) to BL.
Figure 2H:
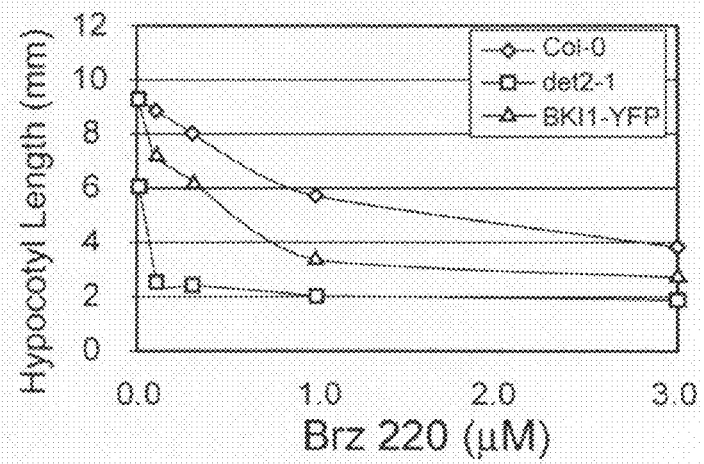
FIG. 2H is a histogram showing that over-expression of BKI1-YFP leads to an enhanced response to BRZ220.

To test whether the dwarf phenotype was the result of altered brassinosteroid sensitivity, we measured the response of a line overexpressing a BKI1-YFP fusion protein to brassinolide (BL). In the absence of applied BL, over-expression of BKI1-YFP led to about a 40% reduction of hypocotyl length in the light (FIG. 2E), and plants were at least 100-fold less sensitive to BL applications compared to wild type, but det2-1, a brassinosteroid biosynthetic mutant, is highly responsive to BL treatment (FIG. 2G). Conversely, the BKI1-YFP line was more sensitive to a brassinosteroid biosynthesis inhibitor, BRZ220 (22), as indicated by the lower concentration of BRZ 220 needed for the BKI1-YFP line ($\approx$0.5 μM) to achieve 50% inhibition of hypocotyl length than for Col-0 ($\approx$2.0 μM), and det2-1 is also highly sensitive to BRZ 220 (FIG. 2H).

To determine whether the growth inhibitory effect caused by the over-expression of BKI1-YFP was due to an inhibition of BRI1 signaling, we tested the phosphorylation status of a downstream biochemical marker, BES1 (10), by immunoblot analysis. Without applied exogenous BL, a significant amount of dephosphorylated BES1 was present in the wild type, while the amount of dephosphorylated BES1 in a BKI1 over-expression line was almost undetectable, which was similar to det2-1. Treatment with 0.1 μM BL for one hour strongly stimulated the accumulation of dephosphorylated BES1 in wild type and det2-1, but to a lesser extent in the BKI1-YFP line (FIG. 2I), suggesting that BRI1 signaling was suppressed by BKI1 over-expression.

Figure 2I:
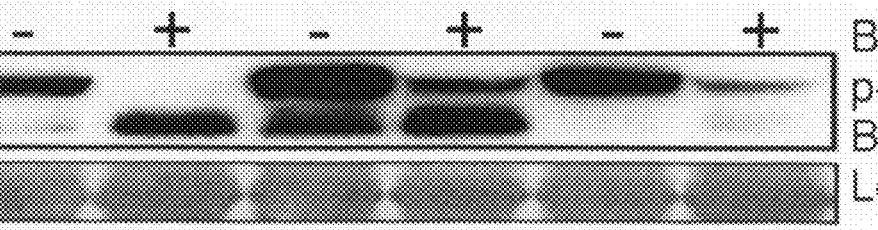
FIG. 2I is an autoradiogram showing that over-expression of BKI1-YFP results in reduced accumulation of dephosphorylated BES1. Immunoblots with anti-BES1 show levels of phosphorylated BES1 (pBES1) and dephosphorylated BES1. Bottom band: loading control.
Figure 2J:
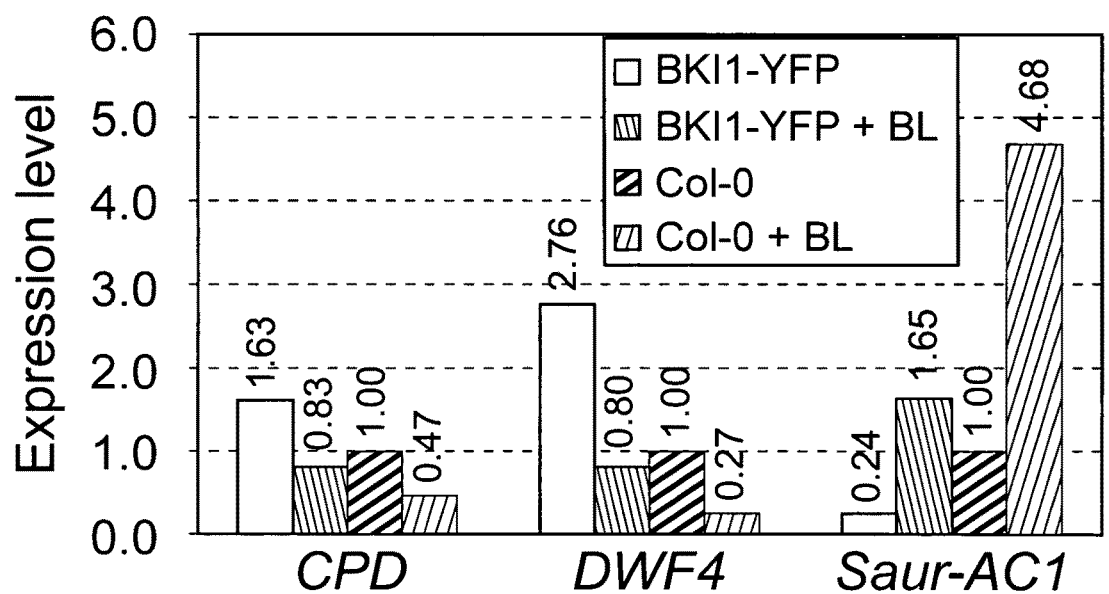
FIG. 2J is a histogram showing that over-expression of BKI1-YFP alters the expression of BR-regulated genes. CPD and DWF4 are BR down-regulated genes, and Saur-AC1 is a BR up-regulated gene. In A, B, G, H, and J, error bars indicate standard error.

To test whether over-expression of BKI1 alters the expression of brassinosteroid responsive genes, we measured the RNA levels of three brassinosteroid-regulated genes by qRT-PCR, including two down-regulated genes, CPD and DWF4, and an up-regulated gene, Saur-AC1. As shown in FIG. 2J, compared with WT, over-expression of BKI1-YFP led to a significant increase of the expression of CPD and DWF4 either without exogenous BL (CPD: 1.63±0.07 vs 1.00; DWF4: 2.76±0.08 vs 1.00) or with a treatment of 100 nM of BL for 2.5 hrs (CPD: 0.83±0.05 vs 0.47±0.03; DWF: 0.80±0.06 vs 0.27±0.01). In contrast, the expression of Saur-AC1 was significantly lower in the BKI1-YFP line than WT in both conditions (No BL: 0.24±0.03 vs 1.00; Plus BL: 1.65±0.11 vs 4.68±0.31). Taken together, these results support the interpretation that BKI1 is a negative regulator of brassinosteroid signaling.

To investigate where in the pathway BKI1 acts, we examined the subcellular localization of the BKI1-YFP fusion protein in plants. BKI1-YFP was localized to both the plasma membrane and the cytosol in root tip cells (FIG. 3A). When the BKI1-YFP line was grown on medium containing 1 μM BRZ220, which reduces the levels of endogenous brassinosteroids (22), the fluorescent signal on the cell surface was enhanced (FIG. 3B). In contrast, when grown on medium containing 1 μM BL, the plasma membrane-association of BKI1-YFP was reduced, as indicated by the diminished discrete fluorescent signal on the cell surface (FIG. 3C), suggesting that brassinosteroids might alter the subcellular localization of BKI1-YFP. Following BL treatment, we observed that the plasma membrane-association of BKI1-YFP was almost completely gone after 5 minutes and undetectable 10 minutes later (FIG. 3G-I); in contrast, the BKI1-YFP signal was unchanged in the control (FIG. 3D-F).

To assess whether the plasma membrane-association of BKI1-YFP was dependent on BRI1, we introduced the BKI1-YFP construct into a bri1-116 background, a null allele of bri1 that generates a stop codon within the BL binding domain (21). In bri1-116 homozygous seedlings, we observed that a significant amount of BKI1-YFP was localized to the cell surface. Unlike wild-type plants, BL treatment failed to induce the dissociation of BRI1 (FIG. 3J-O), indicating that BRI1 is not required for the plasma membrane-association of BKI1-YFP, but is crucial for the release of BKI1 from the plasma membrane. Likewise, in bri1-104, a kinase inactive allele of bri1 (21) that accumulates normal levels of protein, no BL-induced dissociation of BKI1-YFP from the plasma membrane was observed, suggesting that the kinase activity of BRI1 is required for the dissociation of BKI1-YFP from the plasma membrane (FIG. 3P-R). These results imply that BL-induced phosphorylation of BKI1 by activated BRI1 is essential for regulating the subcellular localization and association of BKI1 with BRI1. In corroboration, we found that the yeast two-hybrid interaction of BKI1 with a kinase-inactive BRI1 was stronger than with the kinase active BRI1, although the kinase-active version could still interact with BKI1 (FIG. 7). In addition, BKI1 is a substrate of BRI1 kinase in vitro with a Km of about 1.55 μM (FIG. 7A) and is a phosphoprotein in vivo as indicated by a shift following λ-phosphatase treatment (FIG. 7B).

To confirm whether the plasma membrane-association of BKI1 is required for it to inhibit BRI1 signaling, we made transgenic plants harboring a BKI1-YFP fusion protein that was tethered to the plasma membrane by adding an N-terminal myristoylation site (myriBKI1-YFP). As shown in FIG. 4A, the myriBKI1-YFP was constitutively associated with the plasma membrane even after BL treatment. As expected for a regulator whose inhibitory function is predicted to require an interaction with BRI1 at the plasma membrane, the myriBKI1-YFP line had an enhanced dwarf phenotype, when compared with plants expressing BKI1-YFP to a similar level (FIG. 4B).

Our results suggest that BKI1 may function early in the brassinosteroid signaling pathway, either as an early signaling component or as a regulator that inactivates or desensitizes the receptor. We looked at the interaction of BKI1 with BIN2, the earliest known signaling component downstream of the brassinosteroid receptor complex, but were unable to detect any interaction using genetic assays in yeast (FIG. 1D). Because BAK1 interactions with BRI1 are more stable after application of brassinosteroids (11), we speculated that BKI1 may inhibit the association of BRI1 with positive regulators, e.g., BAK1. To test this prediction, we conducted GST pull-down experiments in vitro and observed that the addition of a BKI1-maltose binding protein fusion (MBP-BKI1) significantly inhibited (by approximately 62%, p=0.000013) the interaction between the kinase domains of BRI1 and BAK1, while the addition of MBP alone did not significantly affect their interaction (p=0.219) (FIG. 4C).

The simplest interpretation of our observations is that plasma membrane-associated BKI1 interacts directly with BRI1 and represses its signaling (FIG. 4D). This model predicts that, in the absence of steroid, BKI1 is localized to the plasma membrane, where it binds to the intracellular domain of a BRI1 homodimer, thus keeping BRI1 from associating with BAK1. Brassinosteroid binding to the extracellular domain of BRI1 induces receptor phosphorylation and activation, as well as its dissociation from BKI1, leaving open binding sites for BAK1 and other unknown positive regulators. BKI1 binding to BRI1 maintains a low basal activity of BRI1. This low activity allows expression of brassinosteroid biosynthetic genes, which are repressed by BRI1 signaling (16, 23, FIG. 2J). BKI1's role in BRI1 signaling appears to be distinct from that of TTL, a negative regulator of the brassinosteroid signal transduction pathway, which associates with a kinase active rather than an inactive BRI1 kinase (18).

BKI1 does not contain a known enzymatic domain, we thought BKI1 may serve as one of adaptor proteins, which associates with receptor tyrosine kinases and recruit signaling components to activated receptors in mammalian systems (24-26). However, BKI1 does not appear to be a typical adaptor, since it must dissociate from the plasma membrane for BRI1 to signal. Rather, BKI1 prevents BRI1 from becoming fully activated and ensures the specificity of BRI1 signaling by preventing its leaky activity. In addition, although the interaction of BKI1 with BRI1 is highly specific, whether it is also involved in other pathways is unknown.

FIG. 1. In Vivo and In Vitro Interaction of BKI1 with BRI1's Intracellular Domain.

FIG. 1A provides a predicted domain structure of AtBKI1. The sequences underlined indicate the region that interacts with BRI1's kinase domain. FIG. 1B provides an alignment of the deduced amino acid sequence of AtBKI1 (SEQ ID NO:1) with BKI1-like proteins from *Oryza sativa* (OsBKI1; AP005891.3; SEQ ID NO:2), *Medicago truncatula*, (MtBKI1; AC157645_3.1 identified in the database of the Institute for Genome Research; SEQ ID NO:3), *Gossypium raimondii* (GrBKI1, a putative full length gene assembled from ESTs: CO071302.1, CO081346.1, 00074191.1, and CO081345.1-; SEQ ID NO:4), and *Euphorbia esula* (EeBKI1, a putative full length gene assembled from ESTs: DV136456.1, DV156616.1, DV139943.1, DV131013.1, and DV131013.1; SEQ ID NO:5). FIG. 1C shows that the carboxyl domain of BKI1 is necessary and sufficient to interact with BRI1's kinase domain in yeast. Residues of BKI1 present in the constructs were 1-252 (BKI1-ΔCT1), 1-299 (BKI1-ΔCT2), and 253-337 (BKI1-CT). FIG. 1D shows that BKI1 specifically interacts with BRI1. BKI1 fused with GAL4-AD (BKI1-pEXAD502) specifically interacts with the intracellular domain of BRI1 (BRI1-KD) fused with GAL4-DB in yeast. FIG. 1E shows that BKI1-6XHIS interacts with GST-BRI1-KD in vitro. In the pull-down product, the GST (Left) or GST-BRI1-KD (Right) was detected by anti-GST, and the S-35 Met labeled BKI1-6XHIS was detected by autoradiography. FIG. 1F shows that BKI1-FLAG interacts with endogenous BRI1 in planta. 1, Col-0; and 2, BKI1-FLAG over-expression line. BRI1 and BKI1-FLAG were detected by immunoblot with anti-BRI1 and anti-FLAG, respectively. FIG. 1 G-J shows that pBKI1::GUS is ubiquitously expressed. GUS reporter gene expression was monitored in two-week-old seedlings leaves and shoot apices (G), hypocotyls (H), and roots (I), and flowers of adult plants (J).

FIG. 2: BKI1 is a Negative Regulator of Brassinosteroid Signaling.

FIG. 2A shows expression level of BKI1 in RNAi knockdown plants and a control line determined by qRT-PCR. FIG. 2B shows that suppression of BKI1 expression leads to longer hypocotyls. Seedlings were grown in short day photoperiods for seven days. At least ten short-day grown seedlings were measured. In FIGS. 2A-B the pBKI1::GUS line was used as a control (control). RNAi-2 and RNAi-7 were two independent RNAi knockdown lines for BKI1. In FIG. 2 C-E, phenotype of plants overexpressing BKI1-FLAG, with Col-0 (left) and a BKI1-FLAG line (right) are shown. 2C. Short-day grown seedlings. 2D. Long-day grown seedlings. 2E. Long-day grown adult plants. In FIG. 2F, leaf morphology of seedlings grown in short days. Col-0 (right) and a BKI1-FLAG line (left) are shown. In FIG. 2G, over-expression of BKI1-YFP leads to a reduced response (hypocotyl length) to BL. At least twenty short-day grown seedlings were measured. In FIG. 2H, over-expression of BKI1-YFP leads to an enhanced response to BRZ220. At least twenty dark-grown seedlings were measured. In FIG. 2I, over-expression of BKI1-YFP results in reduced accumulation of dephosphorylated BES1. Immunoblots with anti-BES1 show levels of phosphorylated BES1 (pBES1) and dephosphorylated BES1. Bottom band: loading control. In FIG. 2J, Over-expression of BKI1-YFP alters the expression of BR-regulated genes. CPD and DWF4 are BR down-regulated genes, and Saur-AC1 is a BR up-regulated gene. In A, B, G, H, and J, error bars indicate standard error.

Figure 3:
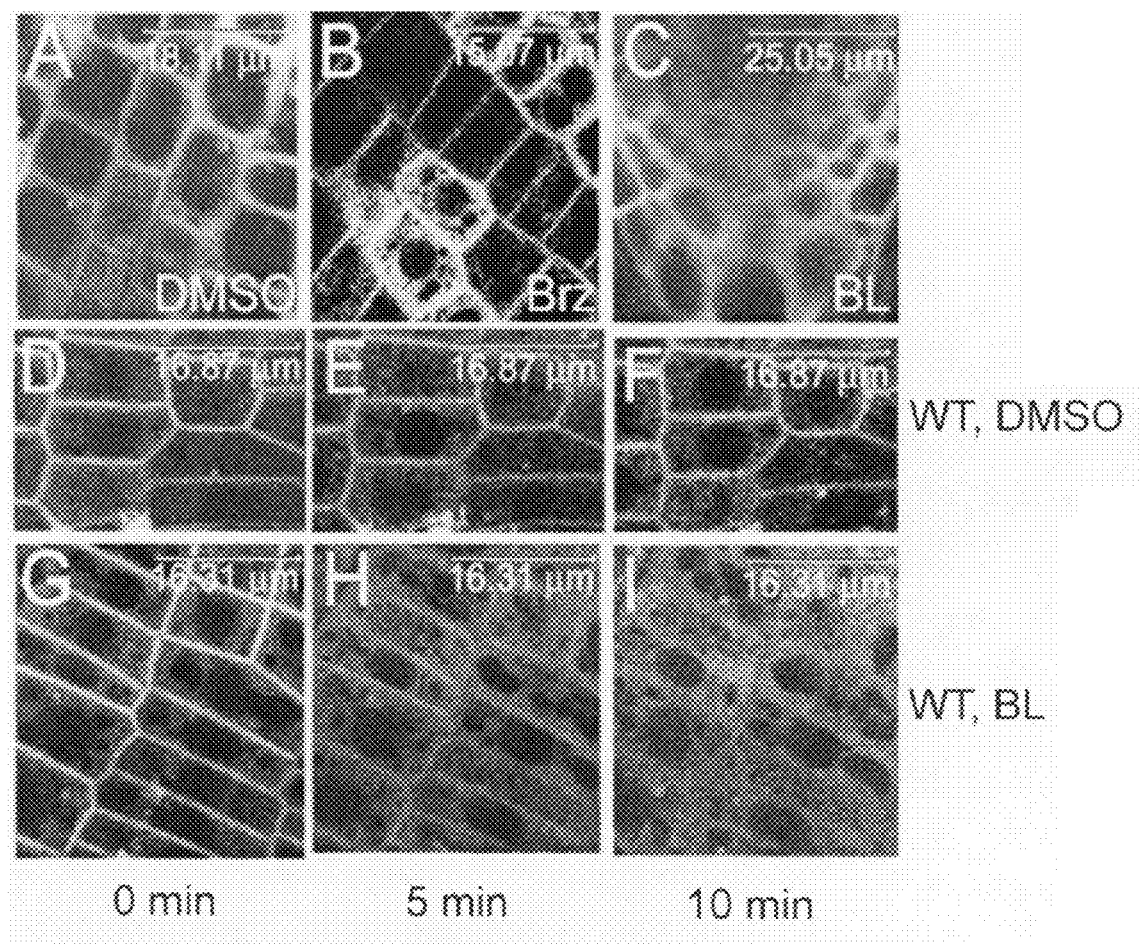
FIG. 3 includes panels A-R.
Figure 3:
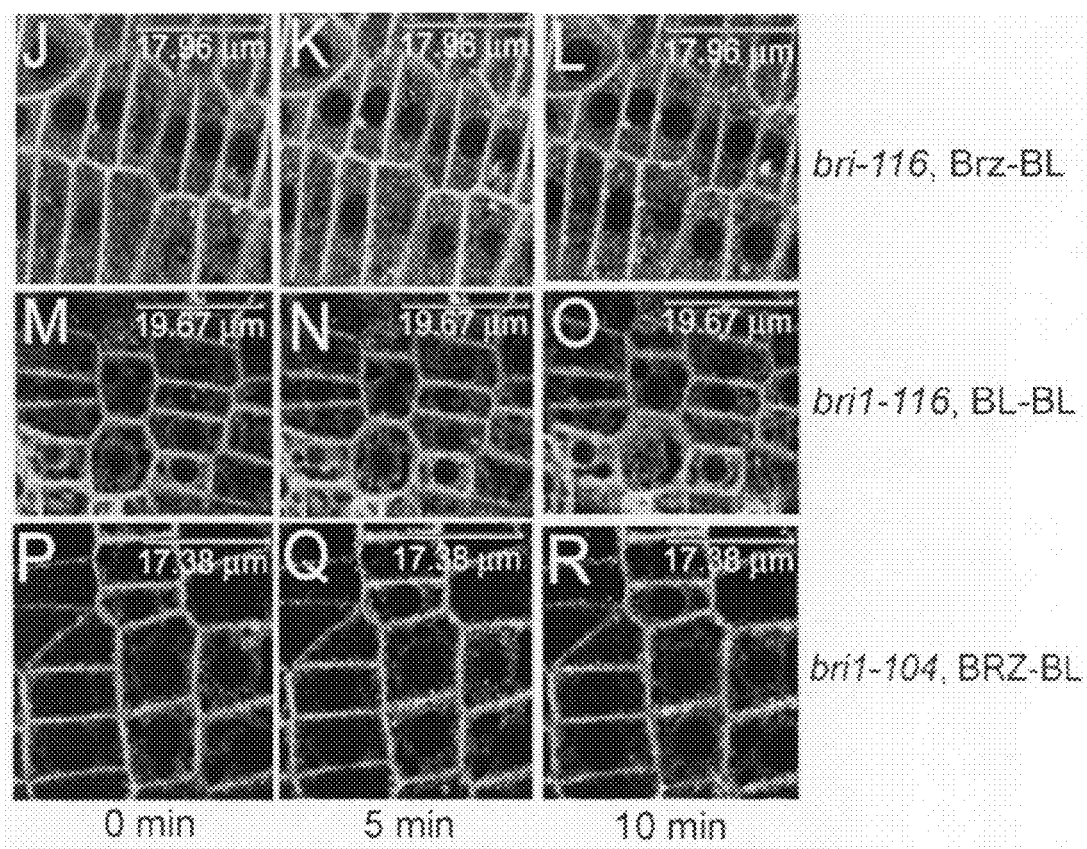

FIG. 3: Brassinosteroid Treatment Triggers the Dissociation of BKI1-YFP from the Plasma Membrane in a BRI1-Dependent Manner.

In FIG. 3A, BKI1-YFP is localized to the plasma membrane and cytosol on MS medium. In FIG. 3B, BRZ220 enhances the association of BKI1-YFP to the plasma membrane. Seedlings were grown on MS medium containing 1 μM BRZ220. In FIG. 3C, BL enhances BKI1-YFP dissociation from the plasma membrane. Seedlings were grown on MS medium containing 1 μM BL. As shown in FIG. 3D-F, DMSO (0.001% (v/v)) does not alter the plasma membrane localization of BKI1-YFP. FIG. 3 G-I shows BL-induced dissociation of BKI1-YFP from the plasma membrane. Seedlings were grown on MS medium containing 1 μM of BRZ220 and treated with 1 μM BL. J-L. BKI1-YFP is associated with the plasma membrane in bri1-116. Seedlings were grown on MS medium containing 1 μM of BRZ220. bri1-116 is a null allele of BRI1 (19). As shown in FIG. 3 M-O, BL does not cause dissociation of BKI1-YFP from the plasma membrane in bri1-116. Seedlings were grown on MS medium containing 1 μM BL. FIG. 3 P-R show that an active kinase is required for BL-induced dissociation of BKI1 from the plasma membrane. bri1-104 is a loss-of-function mutation in the kinase domain of BRI1 (19). Seedlings were grown on MS medium containing 1 μM BRZ220. 3D, G, J, M, and P are untreated; E, H, K, N, and Q are treated with BL for 5 min, and F, I, L, O, and R are treated with BL for 10 min.

FIG. 4: A Model for BKI1 in BRI1 Activation.

FIG. 4A shows that a myristoylated BKI1-YFP is constitutively associated with the plasma membrane following BL treatment. Seedlings were grown on MS medium containing 1 μM of BRZ220. The time of BL treatment is indicated. Top panels: BKI1-YFP; Lower panels: myriBKI1-YFP. FIG. 4B shows that over-expression of a myristoylated BKI1-YFP (myriBKI1-YFP) leads to an enhanced dwarf phenotype. Immunoblots with anti-GFP show levels of myriBKI1-YFP and BKI1-YFP. Bottom band: loading control. FIG. 4 C shows that BKI1 inhibits the interaction between the kinase domains of BRI1 and BAK1 in vitro. The total $^{35}$S-Met labeled BRI1-KD-HIS co-precipitated by GST-BAK1-KD was defined as "1". Five replicates were conducted. Error bars indicate standard error. 1, GST-BAK1-KD±35S-BRI1-KD-HIS; 2, GST-BAK1-KD+35S-BRI1-KD-HIS+10 μM of MBP; 3, GST-BAK1-KD+35S-BRI1-KD-HIS+10 μM of MBP-BKI1. The bottom panel shows a representative gel by autoradiography, indicating the pull-down $^{35}$S-Met labeled BRI1-KD-HIS. FIG. 4D shows a model to illustrate the role of BKI1 in BRI1 signaling. Without BL, BRI1 kinase is kept in a basal state by both its own carboxyl terminal domain and by an interaction with BKI1. Brassinosteroid binding to the extracellular domain of BRI1 induces a conformational change of the kinase domain, leading to the phosphorylation of the C-terminal domain of BRI1 and BKI1, the dissociation of BKI1 from the plasma membrane, and the release of auto-inhibition of BRI1. These events lead to the full activation of BRI1 and its association with BAK1 or other substrates. Plasma membrane-dissociated BKI1 may also regulate other unknown components in the brassinosteroid signaling cascade. BSU1 is a nuclear serine/threonine phosphatase involved in the dephosphorylation of BES1 (27).

FIG. 5: BKI1 Does not Interact with the Kinase Domains of CLV1, BRL1, or BRL3

FIG. 5 shows that BKI1 does not interact with the kinase domains of CLV1, BRL1, or BRL3. BKI1 fused with GAL4-AD (BKI1-pEXAD502) interacts with the intracellular domain of BRI1 (BRI1-KD), but not CLV1 (CLV1-KD), BRL1 (BRL1-KD), and BRL3 (BRL3-KD), fused with GAL4-DB (in pDBLeu) in yeast. pDBLeu was used as a negative control. Each spot from left to right contains 10 µl yeast cell culture with $OD_{600}$=0.2, 0.04, 0.008, and 0.0016.

FIG. 6. The Interaction of BKI1 with Kinase-Inactive BRI1 is Stronger than that with Wild-Type BRI1

FIG. 6 shows the interaction of BKI1 with pDBLeu (CK), the intracellular domain of wild type BRI1 (BRI1-KD), and kinase-inactive BRI1 (mBRI1-KD) was measured with a liquid culture assay using o-Nitrophenyl-β-D-Galactopyranoside (ONPG) as substrate following the manufacture's manual of ProQuest™ Two-Hybrid System with Gateway® Technology (Invitrogen).

FIG. 7. BKI1 is a Substrate of BRI1's Kinase.

FIG. 7A shows that MBP-BKI1 can be phosphorylated by BRI1 kinase in vitro. The intracellular domain of BRI1 (BRI1-KD) was cloned into pETBlue2 (Novagen) with a C-terminal His tag. BKI1 was cloned into the pMAL-2cX vector (New England Biolabs) resulting in an Nterminal maltose-binding protein (MBP) fusion. BRI1-KD-HIS and MBP-BKI1 fusion proteins were expressed in BL21 (DE3) Codon plus RIL (Stratagene) and purified with Ni-NTA agarose (Qiagen) and amylase resin (New England Biolabs), respectively. For the phosphorylation assays, each reaction contained 50 mM HEPES [pH7.4], 10 mM $MgCl_2$, 10 mM $MnCl_2$, 1 mM DTT, 200 µM ATP, 1 µl (10 µCi) [$\gamma$-$_{32}$P] ATP, 0.5 µl of BRI1-His, different amounts of MBP-BKI1, and double deionized $H_2O$ in a final volume of 24 µl. Reactions were terminated by addition of 8 µl of 4×SDS loading buffer. Samples were separated on a 4-20% Tris-Glycine SDS-PAGE gel (Invitrogen), which was then stained, destained, dried, and visualized and quantified using a PhosphorImager. The kinetic analysis of the phosphorylation of MBP-BKI1 by BRI1 kinase was conducted with a GraphPad Prism 4 (http://www.graphpad.com/prism/Prism.htm). FIG. 7B shows that BKI1-FLAG is a phosphoprotein in planta. Seedlings of a BKI1-FLAG over-expression line were grown on ½ MS medium containing 1 µM BL for 1 week, and then total proteins were extracted with 1:2 (w/v) lysis buffer containing 1× ZOOM 2D protein solubilizer 1 (Invitrogen), 3 mM Tris base, 20 mM DTT, and 1:50 protein inhibitor cocktail (Sigma). Half of the extract was treated with γ phosphatase (+γPPase) for 30 min at room temperature. Samples were separated on 11 cm, 3-10 nonlinear immobilized pH gradient (IPG) strips (Bio-Rad) with a PROTEAN IEF Cell (Bio-Rad) at the first dimension, then onto 4-20% Criterion Precast Tris-HCl gels (Bio-Rad) at the second dimension. The BKI1-FLAG protein was detected by immunoblot analysis with anti-FLAG antibody.

Table 1. Identification of Plant ESTs with High Similarity to AtBKI1

The entire predicted amino acid sequence of AtBKI1 was used to blast the public EST database. Table 1 Lists plant ESTs highly similar to AtBKI1.

TABLE 1

| Plants | Genebank accession number |
| --- | --- |
| *Antirrhinum majus* | AJ796385.1, AJ796560.1 (SEQ ID NOs: 20-21) |

TABLE 1-continued

| Plants | Genebank accession number |
| --- | --- |
| *Citrus sinensis* | CX674446.1 (SEQ ID NO: 22) |
| *Curcuma longa* | DY389957.1 (SEQ ID NO: 23) |
| *Glycine max* | BU579318.1, BE609508.1, BE609498.1, AW620804.1 (SEQ ID NOs: 24-27) |
| *Helianthus petiolaris* | DY946533.1 (SEQ ID NO: 28) |
| *Ipomoea nil* | BJ557111.1, BJ575601.1 (SEQ ID NOs: 29-30) |
| *Lettuce sativa* | DY971277.1, BQ867285.1 (SEQ ID NOs: 31-32) |
| *Mesembryanthemum crystallinum* | BE130683.1 (SEQ ID NO: 33) |
| *Nicotiana benthamiana* | CK287132.1 (SEQ ID NO: 34) |
| *Nicotiana tabacum* | EB435640.1 (SEQ ID NO: 35) |
| *Phaseolus vulgaris* | BQ481779.1 (SEQ ID NO: 36) |
| *Populus deltoides* | CX170112.1, CX175441.1, CX175253.1 (SEQ ID NOs: 37-39) |
| *Populus trichocarpa* | DT481968.1, DT487361.1 (SEQ ID NOs: 40-41) |
| *Prunus persica* | DY636517.1 (SEQ ID NO: 42) |
| *Solanum tuberosum* | CX162638.1 (SEQ ID NO: 43) |
| *Thellungiella salsuginea* | DN773886.1 (SEQ ID NO: 44) |
| *Trifolium pratense* | BB923413.1 (SEQ ID NO: 45) |

Additional Example Details

Plant Materials and Growth Conditions

The Columbia (Col-0) ecotype was used. In over-expression studies, phenotypic analysis of all transgenic lines and controls were conducted on plates with ½ MS (Gibco) and 0.8% phytagar (Gibco), with addition of 40 µg/ml Kanamycin for selecting transgenic plants. Plants were grown at 22° C. under white light (16 hr light/8 hr dark cycles for long-day treatment or 8 hr light/16 hr dark for short-day treatment) or continuous dark.

Yeast Two-Hybrid Screens and Assays

A ProQuest Two-Hybrid system with Gateway technology (Invitrogen) was used. The kinase domains (828-1196) of wild-type and kinase-inactive BRI1 (K911E) were cloned into the pDBLeu vector and used as baits to identify interacting proteins with a cDNA library, which was prepared with RNA from micro-dissected apices from Col-0 plants once they had bolted. The cDNA synthesized from this material was cloned into the bait vector pEXP-AD502 with SalI NotI linkers. The full-length (BKI1-FL), and various truncated proteins, 1-252 (BKI1-ΔCT1), 1-299 (BKI1-ΔCT2), and 253-337 (BKI1-CT) of BKI1 were cloned into the pEX-PAD502 vector. The kinase domain of NIK1 (NIK1-KD) (Fontes et al. (2004) *Genes Dev.* 18:2545), BAK1 (BAK1-KD), CLV1 (CLV1-KD), BRL1 (BRL1-KD), BRL3 (BRL3-KD), full length TTL, and full-length BIN2 were cloned into the pDBLeu vector. Interactions were tested on SD medium minus Leu, Trp, and His, and containing 25 mM 3-Amino-1, 2,4-Triazole (3AT), using the yeast strain MaV203 according to the manufacturer's manual.

In Vitro Binding Assays

BKI1 was cloned into pETBlue2 vector (Novagen), and recombinant protein BKI1-6×HIS was in vitro translated and labeled with $_{35}$S-methionine by the TNT T7 coupled reticulocyte lysate system (Promega). Glutathione agarose beads containing 4 µl each of GST, GST-BRI1-KD (10) were incubated with 25 µl BKI1 TNT reactions in Tris Buffered Saline (TBS) buffer (50 mM Tris-HCl [pH 7.5], 0.9% NaCl) to a final volume of 100 µl for 2 hr at 4° C. The beads were washed five times with TBS buffer. The proteins were eluted with 20 µl 1×SDS buffer by boiling for 5 min. Half of the eluted sample was separated onto a SDS-PAGE gel. The gel was fixed, dried, and exposed to a PhosphorImager (Molecular Dynamics). The other half was used to determine the content of GST and GST fusion proteins by immunoblot analysis with anti-GST antibody. To test whether BKI1 regulates the interaction between the kinase domains of BRI1 and BAK1, the BRI1-KD-HIS fusion protein was in vitro translated and labeled with $_{35}$S-methionine as described above. The kinase domain of BAK1 (GST-BAK1-KD) was expressed and purified as an N-terminal GST fusion (9). Glutathione agarose beads (30 µl) with 5 µg GST-BAK1-KD protein were incubated with 20 µl of TNT reactions in pull-down buffer (50 mM Tris [pH 7.5], 150 mM NaCl, and 0.1% NP-40) with different combinations of other proteins as indicated to a final volume of 60 µl for overnight at 4° C. The beads were washed three times with Phosphate Buffered Saline (PBS) buffer. The bound proteins were eluted with 1×SDS buffer and separated on a SDS-PAGE gel, and the gel was fixed, dried, and exposed to a PhosphorImager (Molecular Dynamics) to determine the amount of $_{35}$S-labelled BRI1-KD-HIS.

Immunoprecipitation

Short-day grown seedlings of Col-0 and transgenic plants containing BKI1-FLAG were ground to a fine powder in liquid nitrogen, and solubilized with 2× extraction buffer (100 mM Tris-HCl pH 7.5, 300 mM NaCl, 2 mM EDTA, 1% Triton, 10% glycerol, and protease inhibitor). The extracts were centrifuged at 5,000×g for 10 min, and the resultant supernatant was then spun at 100,000×g for 90 min at 4° C. to remove membrane fractions. The supernatant was incubated with pre-washed anti-FLAG M2 agarose gel (Sigma) for three hours at 4° C., and the agarose gel was washed five times with TBS Buffer containing 0.02% Tween 20. The immunoprecipitates were eluted with 1×SDS sample buffer by boiling for 5 min, separated on a 4-20% Novex Tris-Glycine SDS-PAGE gel (Invitrogen), transferred to PVDF membrane (Millipore), and detected with either anti-BRI1 antibody for endogenous BRI1 or monoclonal anti-FLAG M2 (Sigma) for BKI1-FLAG. Signals were visualized using the Odyssey Infrared Imaging system (LI-COR Biosciences Inc.).

BKI1 Expression Analysis

A 1970 bp genomic fragment from the BKI1 promoter region was amplified from Col-0 genomic DNA and cloned into a modified pHJA212K binary vector (Yoo et al. (2005) *Planta* 221:523) containing the *E. coli* GUS coding sequence and a TUB4 terminator. The GUS-reporter construct was then transformed into Col-0. Histochemical staining of plants expressing the pBKI1::GUS reporter gene was performed as described (Blázquez et al. (1997) *Development* 124:3835). After staining, the seedlings were rinsed sequentially with 20%, 50%, and 70% (v/v) ethanol. Digital images were taken with a Leica MZ FLIII stereomicroscope (Leica Microsystems, Germany).

Creation of RNAi Lines

To knock down BKI1, a 661 bp fragment was amplified from BKI1 with primers 5'-CACCGACATCGTCTTAT-CAACAAACCGAT-3' (SEQ ID NO:6) and 5'-ACACAC-GAAGATGGCCACTATT-3' (SEQ ID NO:7), and cloned into pENTRTOPO (Invitrogen). A RNAi construct was made with a binary vector pK7GWIW2(I) (Karimi et al. (2005) *Trends in Plant Sci.* 10: 103) using the methods described for Gateway vectors and transformed into Col-0 plants.

Generation of Transgenic Plants and Visualization of Protein Localization

The predicted full-length BKI1 was amplified by RT-PCR from total RNA of Col-0 using Pfu DNA polymerase (Stratagene), and cloned into the binary vector pCHF3 that contains a 35S promoter (10), three copies of FLAG (DYKD-DDDKVKL, SEQ ID NO:8) fused at the Cterminal end, and the RubisCo small subunit (rbcS) terminator. For the YFP fusion construct, full length BKI1 was cloned into a modified pCHF3 containing a 35S promoter and a C-terminal YFP tag. For the myriBKI1-YFP construct, a myristoylation site (MGICMSR, SEQ ID NO:9) was added to the N-terminus of BKI1-YFP via PCR. All constructs were confirmed by sequencing and transformed into Col-0 plants. The subcellular localization of BKI1-YFP and myriBKI1-YFP was visualized and photographed using a Leica TCS SP2 confocal microscope (Leica Microsystems, Germany).

Gene Expression Analysis by Quantitative PCR

Plants were treated with 100 nM BL, or a mock treatment for 2.5 hrs. Total RNA was extracted using a Qiagen RNAeasy kit (Valencia, Calif.), and the first strand cDNA was synthesized using Invitrogen Superscript III First-Strand cDNA Synthesis kit. cDNAs were combined with SYBR master mix for PCR. Primers for each gene are shown as follows. CPD (At5g05690): 5'-TTACCGCAAAGCCATC-CAA-3' (SEQ ID NO:10) and 5'-TCATCACCACCACCGT-CAAC-3' (SEQ ID NO:11); DWF4 (At3g50660): 5'-GTTG-GCCATTICTTGGTGAAA-3' (SEQ ID NO:12) and 5'-TGGCGGTGTACGGTTTAAGAT-3' (SEQ ID NO:13); Saur-AC1 (At4g38850): 5'-TTGGGTGCTAAGCAAAT-TATTCG-3' (SEQ ID NO:14) and 5'-TCTCCTACATAGAC-CGCCATGA-3' (SEQ ID NO:15); and BKI1: 5'-GCTCCG-GCGTCGATGA-3' (SEQ ID NO:16) and 5'-GACGATAGTCCGGCCGTAGA-3' (SEQ ID NO:17). A U-box gene (At5g15400) was used to normalize the data (5'-TGCGCTGCCAGATAATACACTATT-3' (SEQ ID NO:18) and 5'-TGCTGCCCAACATCAGGTT-3' (SEQ ID NO:19)). PCR reactions were performed in triplicate or quadruplicate with a Bio-Rad iCycler, and the data were collected and analyzed with Bio-Rad MyiQ Single-Color Real-Time PCR Detection System.

CITED REFERENCES

1. S. H. Shiu, A. B. Bleecker, *Proc. Natl. Acad. Sci. U.S.A.* 98, 10763 (2001).
2. J. Li, J. Chory, *Cell* 90, 929 (1997).
3. Z. Y. Wang, H. Seto, S. Fujioka, S. Yoshida, J. Chory, *Nature* 410, 380 (2001).
4. T. Kinoshita et al., *Nature* 433, 167 (2005).
5. G. Vert, J. L. Nemhauser, N. Geldner, F. Hong, J. Chory, *Annu. Rev. Cell Dev. Biol.* 21, 177 (2005).
6. S. D. Clouse, M. Langford, T. C. McMorris, *Plant Physiol.* 111, 671 (1996).
7. T. Altmann, *Curr. Opin. Plant Biol.* 1, 378 (1998).
8. K. H. Nam, J. Li, *Cell* 110, 203 (2002).
9. J. Li et al., *Cell* 110, 213 (2002).
10. X. L. Wang et al., *Dev. Cell* 8, 855 (2005).
11. X. Wang et al., *Plant Cell* 17, 1685 (2005).
12. J. Li, K. H. Nam, *Science* 295, 1299 (2002).
13. Z. Y. Wang et al., *Dev. Cell* 2, 505 (2002).
14. Y. Yin et al., *Cell* 109, 181 (2002).
15. Y. Yin et al., *Cell* 120, 249 (2005).
16. J. He et al., *Science* 307, 1634 (2005).
17. G. Vert, J. Chory, *Nature* 441, 96 (2006).
18. K. H. Nam, J. Li, *Plant Cell* 16, 2406 (2004).
19. S. Hirabayashi et al., *Plant Biotech.* 21, 35 (2004).
20. A. Caño-Delgado et al., *Development* 131, 5341 (2004).
21. D. M. Friedrichsen, C. A. Joazeiro, J. Li, T. Hunter, J. Chory, *Plant Physiol.* 123, 1247 (2000).
22. K. Sekimata et al., *Tetrahedron Asymmetry* 13, 1875 (2002)
23. K. Tanaka et al., *Plant Physiol.* 138, 1117 (2005).

24. H. Kouhara et al., *Cell* 89, 693 (1997).
25. G. R. Guy, P. Yusoff, D. Bangarusamy, C. W. Fong, E. S. Wong, *Cell Signal.* 14, 11 (2002).
26. L. J. Holt, K. Siddle, *Biochem. J.* 388, 393 (2005).
27. S. Mora-Garcia et al., *Genes Dev.* 18, 448 (2004).

While the foregoing invention has been described in some detail for purposes of clarity and understanding, it will be clear to one skilled in the art from a reading of this disclosure that various changes in form and detail can be made without departing from the true scope of the invention. For example, all the methods, compositions and systems described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A transgenic plant that comprises a recombinant modulator that modulates expression of a bki 1-type gene, wherein the modulator inhibits expression of a BKI 1-type polypeptide.

2. The transgenic plant of claim 1, wherein the transgenic plant additionally expresses a recombinant BKI 1-type polypeptide.

3. The transgenic plant of claim 2, wherein the modulator and the recombinant BKI 1-type polypeptide display tissue-specific expression.

4. The transgenic plant of claim 3, wherein the modulator and the recombinant BKI I-type polypeptide display non-identical patterns of tissue-specific expression.

5. The transgenic plant of claim 3, wherein tissue-specific expression of the polypeptide or modulator includes a higher level of expression of the recombinant BKI 1 type polypeptide in leaves of the plant than in seeds of the plant.

6. The transgenic plant of claim 3, wherein the plant displays a decreased response to brassinolide in at least one tissue of the plant.

7. The transgenic plant of claim 6, wherein the decreased response comprises:
   reduced expression of one or more genes in the tissue that are expressed in response to brassinolide; and,
   increased expression of brassinosteroid synthetic genes in the tissue that are repressed by brassinolide.

8. The transgenic plant of claim 2, wherein expression of the BKI 1-type polypeptide or modulator induces a phenotype in the transgenic plant selected from the group consisting of: decreased sensitivity to brassinosteroids, increased sensitivity to brassinosteroids, improved yield under dense planting conditions, increased leaf erectness, stress tolerance, increased tolerance to biotic or abiotic stress, decreased tolerance to biotic or abiotic stress, enhanced dwarfism, increased stature, decreased stature, increased stem length, decreased stem length, altered vascular differentiation, increased seed size, decreased seed size, increased fertility, decreased fertility, increased time to senescence, decreased time to senescence, increased hypocotyl length, decreased hypocotyl length, accelerated flowering, delayed flowering, increased petiole length, decreased petiole length, increased cell elongation, decreased cell elongation, rounded leaves, and combinations thereof.

9. The transgenic plant of claim 1, wherein the modulator is an RNAi or antisense molecule that inhibits translation of an mRNA that encodes the BKI 1-type polypeptide.

10. The transgenic plant of claim 1, wherein the modulator reduces expression of a BKI 1-type polypeptide encoded by the gene by at least 50% in the plant.

11. The transgenic plant of claim 1, wherein the modulator inhibits expression of a BKI 1-type polypeptide in the transgenic plant, thereby derepressing brassinosteroid signalling in the transgenic plant.

12. The transgenic plant of claim 1, wherein the modulator is expressed tissue specifically.

13. The transgenic plant of claim 1, wherein the transgenic plant displays increased expression of at least one brassinosteroid responsive gene as compared to a control plant.

14. The transgenic plant of claim 1, wherein the plant is an angiosperm.

15. The transgenic plant of claim 1, wherein the plant is a monocot.

16. The transgenic plant of claim 1, wherein the plant is a dicot.

17. The transgenic plant of claim 1, wherein the plant is a member of a plant family selected from: the Orchidaceae, the Asteraceae or Compositae, the Fabaceae or Leguminosae, the Poaceae or Gramineae, the Rubiaceae, the Euphorbiaceae, the Malvaceae, the Cyperaceae or Araceae.

18. The transgenic plant of claim 1, wherein the plant is a member of a species selected from the group of genera consisting of: *Agrostis, Allium, Antirrhinum, Apium, Arabidopsis, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis,*

*Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pela~gonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setria, Sinapis, Soanum, Sorghum, Stenotaphrum, Theobroma, Trifolium, Trigonella, Triticum, Vicia, Vigna, Vilis, Zea,* the Olyreae, and the Pharoideae.

19. The transgenic plant of claim 1, wherein the plant is a member of a species selected from the group consisting of: *Antirrhinum majus, Citrus sinensis, Curcuma longa, Glycine max, Helianthus petiolaris, Ipomoea nil, Lettuce sativa, Mesembryanthemum crystallinum, Nicotiana benthamiana, Nicotiana tabacum, Phaseolus vulgaris, Populus deltoids, Populus trichocarpa, Prunus persica, Solanum tuberosum, Thellungiella salsuginea,* and *Trifolium pratense.*

20. The transgenic plant of claim 1, wherein the plant is a barrelclover, a turfgrass, a forage plant, a cotton, a *Glycine max,* a *Zea mays,* a Sunflower, a Sorghum, a Wheat, a Rice, a barley, a tomato, an oil rape, or a Canola plant.

21. A recombinant cell comprising an expression vector that encodes a modulator of a bki 1-type gene, wherein the modulator inhibits expression of a BKI 1 type polypeptide.

22. The recombinant cell of claim 21, wherein the cell is a recombinant plant cell.

23. The recombinant cell of claim 21, wherein the cell is a cell of a recombinant plant.

24. The recombinant cell of claim 21, wherein the BKI 1 type polypeptide, or an encoding nucleic acid thereof, comprises a sequence of SEQ ID NO:1.

25. The recombinant cell of claim 21, wherein the polypeptide is a full-length protein.

26. A method of modulating a brassinosteroid response in a cell, the method comprising:
  expressing a modulator in the cell, which modulator inhibits expression or activity of a BKI 1-type polypeptide in the cell, and
  wherein said modulator of the BKI 1-type polypeptide or gene derepresses the brassinosteroid response in the cell,
  thereby modulating the brassinosteroid response in the cell.

27. The method of claim 26, wherein the cell is a recombinant plant cell.

28. The method of claim 26, wherein the cell is a cell of a recombinant plant.

* * * * *